United States Patent
Adams et al.

(10) Patent No.: US 7,098,337 B2
(45) Date of Patent: Aug. 29, 2006

(54) 1,2,3,4,9,9A-HEXAHYDRO-2,4A,5-TRIAZA-FLUORENE AND 1,2,3,4-TETRAHYDRO-2,4A,5- TRIAZA-FLUORENE DERIVATIVES

(75) Inventors: David Reginald Adams, Wokingham (GB); Jonathan Mark Bentley, Wokingham (GB); Toby Jonathan Blench, Wokingham (GB); Paul Hebeisen, Basel (CH); Nathaniel Julius Thomas Monck, Wokingham (GB); Hans Richter, Grenzach-Wyhlen (DE); Stephan Roever, Inzlingen (DE); Jonathan Richard Anthony Roffey, Wokingham (GB); Sven Taylor, Riedisheim (FR)

(73) Assignees: Hoffmann-La Roche Inc., Nutley, NJ (US); Vernalis Research Limited, Winnersh (GB)

( * ) Notice: Subject to any disclaimer, the term of this patent is extended or adjusted under 35 U.S.C. 154(b) by 147 days.

(21) Appl. No.: 10/350,616

(22) Filed: Jan. 24, 2003

(65) Prior Publication Data
US 2003/0207888 A1 Nov. 6, 2003

(30) Foreign Application Priority Data
Jan. 29, 2002 (GB) ................................ 0202015.4

(51) Int. Cl.
C07D 471/14 (2006.01)
A61K 31/4985 (2006.01)
A61P 3/04 (2006.01)
(52) U.S. Cl. ...................... 544/346; 514/250
(58) Field of Classification Search ............... 514/250; 544/346
See application file for complete search history.

(56) References Cited

U.S. PATENT DOCUMENTS

| | | | |
|---|---|---|---|
| 4,598,089 A | 7/1986 | Hadvary et al. | |
| 4,931,463 A | 6/1990 | Barbier et al. | |
| 4,983,746 A | 1/1991 | Barbier et al. | |
| 5,245,056 A | 9/1993 | Karpf et al. | |
| 6,004,996 A | 12/1999 | Shah et al. | |
| 6,495,543 B1 | 12/2002 | Guillamet et al. | |

FOREIGN PATENT DOCUMENTS

| | | |
|---|---|---|
| EP | 185359 | 6/1986 |
| EP | 189577 | 8/1986 |
| EP | 443449 | 8/1991 |
| EP | 524495 | 1/1993 |
| WO | WO 99/34786 | 7/1999 |
| WO | WO 00/09122 | 2/2000 |
| WO | WO 00/09123 | 2/2000 |
| WO | WO 00/44753 | 8/2000 |

OTHER PUBLICATIONS

West, Anthony R., Solid State Chemistry and its Applications, Wiley, New York, 1988, pp. 358 & 365.*
Bickerdike MJ., Curr Top Med Chem. 2003;3(8):885-97, Abstract only, PMID: 12678838.*
Jones BJ, Blackburn TP., Pharmacol Biochem Behav. Apr. 2002; 71(4):555-68.*
Serretti A, Artioli P, De Ronchi D., Expert Opin Ther Targets. Feb. 2004;8(1):15-23.*
Kimura Y, Hatanaka K, Naitou Y, Maeno K, Shimada I, Koakutsu A, Wanibuchi, F. Yamaguchi T., Eur J Pharmacol. Jan. 1, 2004;483(1)37-43.*
Keller & Wahli, Trends Endocrin. Metab. 1993; vol. 4: pp. 291-296.
Macdonald & Lane, Current Biology vol. 5, pp. 618-621 (1995).
Eur. J. Pharmacol. Jul. 20, 2001, vol. 424(2), pp. 85-90.
Psychopharmacol. Bull. 1989. vol. 25(3) pp. 393-397.

* cited by examiner

*Primary Examiner*—Thomas C. McKenzie
(74) *Attorney, Agent, or Firm*—George W. Johnston; Dennis P. Tramaloni; Samuel H. Megerditchian

(57) ABSTRACT

The present invention relates to compounds of formula (I)

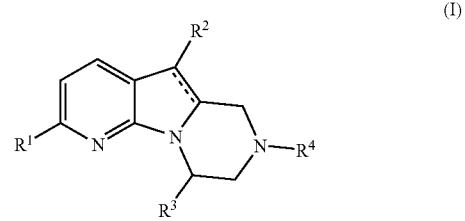

as well as pharmaceutically acceptable salts, solvates and esters thereof. These compounds can be used to prepare pharmaceutical compositions for the treatment or prevention of disorders of the central nervous system, damage to the central nervous system, cardiovascular disorders, gastrointestinal disorders, diabetes, obesity and sleep apnoea.

34 Claims, No Drawings

1,2,3,4,9,9A-HEXAHYDRO-2,4A,5-TRIAZA-FLUORENE AND 1,2,3,4-TETRAHYDRO-2,4A,5-TRIAZA-FLUORENE DERIVATIVES

FIELD OF THE INVENTION

The present invention relates to new piperazine derivatives, to processes and intermediates for their preparation, and to pharmaceutical compositions containing them. These compounds are useful in treating obesity and other disorders mediated by $5HT_2$ receptors.

BACKGROUND OF THE INVENTION

It has been recognised that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI) which is calculated by dividing body weight (kg) by height squared (m²). Thus, the units of BMI are $kg/m^2$ and it is possible to calculate the BMI range associated with minimum mortality in each decade of life. Overweight is defined as a BMI in the range 25–30 $kg/m^2$, and obesity as a BMI greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80–90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to pancreas exhaustion.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycaemia, particularly NIDDM are urgently needed. Recent studies provided evidence that coagonism of PPARα and PPARγ would result in compounds with enhanced therapeutic potential, i. e. with an improved lipid profile effect on top of the normalization of glucose- and insulin-levels (Keller and Wahli: Trends Endocrin. Metab. 1993; 4: 291–296, Macdonald and Lane: Current Biology Vol. 5 pp. 618–621 (1995)).

SUMMARY OF THE INVENTION

It is an object of this invention to provide selective, directly acting $5HT_2$ receptor ligands for use in therapy and particularly for use as anti-obesity agents. It is a further object of this invention to provide directly acting ligands selective for $5\text{-}HT_{2B}$ and/or $5\text{-}HT_{2C}$ receptors, for use in therapy and particularly for use as anti-obesity agents. It is a further object of this invention to provide selective, directly acting $5\text{-}HT_{2C}$ receptor ligands, preferably $5\text{-}HT_{2C}$ receptor agonists, for use in therapy and particularly for use as anti-obesity agents.

The compounds of this invention are either $5HT_2$ receptor agonists or antagonists. A skilled artisan can readily ascertain by conventional assays which compounds are antagonists and which are agonists (see e.g. Eur. J. Pharmacol. 2001 Jul. 20; 424(2):85–90; Psychopharmacol. Bull. 1989; 25(3):393–7). Preferably, these compounds are agonists.

In one embodiment, the invention relates to compounds of formula I and their pharmaceutically acceptable salts, solvates and esters

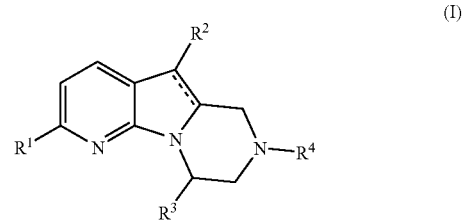

wherein
$R^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino, haloalkyl, hydroxyalkoxy, alkoxyalkoxy, hydroxyalkoxyalkyl, alkylcarbonyl, haloalkylcarbonyl, alkyl-S—, alkenyl-S—, $A^1$ or $A^2$;

$R^2$ is hydrogen, alkyl or alkoxy;

$R^3$ is alkyl, hydroxyalkyl or alkoxyalkyl;

$R^4$ is hydrogen or alkyl;

$A^1$ is

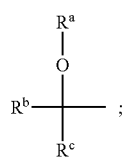

$R^a$ is hydrogen, alkyl, cycloalkyl or cycloalkylalkyl;

$R^b$ is hydrogen or alkyl; or $R^a$ and $R^b$ together with the oxygen atom and the carbon atom to which they are attached form tetrahydrofuranyl;

$R^C$ is haloalkyl, alkyl, alkoxyalkyl or thiazolyl;

$A^2$ is

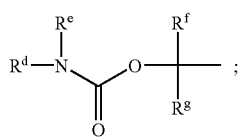

$R^d$ is alkyl, cycloalkyl, aryl, aralkyl or alkenyl;

$R^e$ is hydrogen or alkyl; or $R^d$ and $R^e$ together with the nitrogen atom to which they are attached form pyrrolidinyl or benzyloxycarbonylpiperazinyl;

$R^f$ is hydrogen or alkyl; and $R^g$ is hydrogen or alkyl.

The compounds of formula (I) are useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes may be diabetes secondary to pancreatic disease; or diabetes related to steroid use. The compounds of formula (I) are also useful in the treatment and/or prevention of the sequelae of hyperglycaemia; in the treatment and/or prevention of diabetic complications; and in the treatment of insulin dependence.

The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

In another embodiment, the present invention relates to a method of acute and/or chronic treatment and/or prevention of disorders involving elevated plasma blood glucose, particularly the acute and/or chronic treatment of disorders involving elevated plasma blood glucose, and especially acute treatment of disorders involving elevated plasma blood glucose.

DETAILED DESCRIPTION OF THE INVENTION

As used herein, the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and cyclopentyl and particularly cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

The term "haloalkyl", alone or in combination, signifies an alkyl group as previously defined, wherein one or several hydrogen atoms, preferably one to three hydrogen atoms have/has been replaced by halogen. Examples of haloalkyl groups are trifluoromethyl, trifluoroethyl, pentafluoroethyl and trichloromethyl. Preferred examples are monofluoromethyl, trifluoromethyl and difluoromethyl. Particularly preferred is trifluoromethyl.

The term "carbonyl" refers to a group of the formula —C(O)—.

The term "aryl", alone or in combination, signifies a phenyl or naphthyl group which optionally carries one to three substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert-butoxyphenyl, 4-fluorophenyl, 2-chlorophenyl, 3-chlorophenyl, 4-chlorophenyl, 4-hydroxyphenyl, 1-naphthyl and 2-naphthyl. Preferred are phenyl, 4-fluorophenyl, 1-naphthyl and 2-naphthyl and particularly phenyl.

The term "aralkyl", alone or in combination, signifies an alkyl or cycloalkyl group, preferably an alkyl group as previously defined in which one or several, preferably one hydrogen atom has been replaced by an aryl group as defined before. Preferred is benzyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, morpholin-1-yl, pyrrolidin-1-yl or piperidinyl etc., preferably amino, dimethylamino and diethylamino and particularly primary amino.

The term "halogen" signifies fluorine, chlorine, bromine or iodine and preferably fluorine, chlorine or bromine and particularly chlorine and bromine.

The term "carboxy", alone or in combination, signifies a —COOH group.

The term "alkenyl" alone or in combination signifies a straight-chain or branched-chain hydrocarbon group comprising a carbon carbon double bond and 1 to 10, preferably 1 to 8 carbon atoms, more preferably 1–4 carbon atoms. Preferred examples are ethenyl and allyl.

The term "cyano", alone or in combination, signifies a —CN group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

The invention expressly includes pharmaceutically usable solvates of compounds according to formula I. The compounds of formula I can be solvated, e.g. hydrated. The solvation can be effected in the course of the manufacturing process or can take place, e.g. as a consequence of hygroscopic properties of an initially anhydrous compound of formula I (hydration). The term pharmaceutically acceptable salts also includes physiologically usable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No.6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

In the nomenclature used in the present application the carbon atoms of the basic ring system of the compounds according to formula I are numbered as follows:

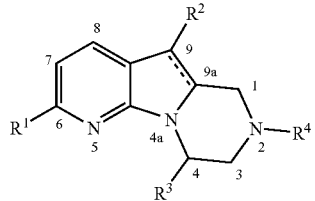
(I)

wherein $R^1$ is attached to the 6-position, $R^2$ is attached to the 9-position and $R^3$ is attached to the 4-position.

Preferred compounds of formula I, and their pharmaceutically acceptable salts, solvates and esters, are compounds

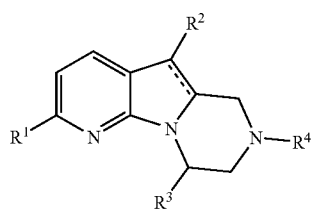
(I)

wherein $R^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino or haloalkyl;

$R^2$ is hydrogen, alkyl or alkoxy;

$R^3$ is alkyl, hydroxyalkyl or alkoxyalkyl; and $R^4$ is hydrogen or alkyl.

The dotted lines in formula I (marked as *) represent a single or a double bond

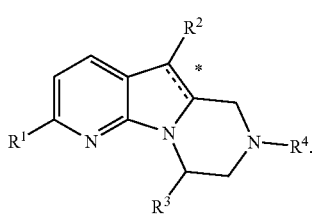
(I)

Accordingly, compounds of formula (I) are of one of the following formulae (Ia) and (Ib)

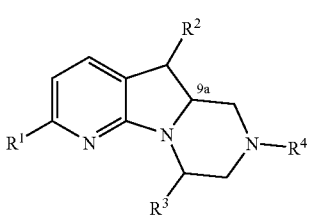
(Ia)

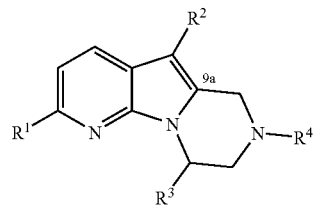
(Ib)

wherein $R^1$ to $R^4$ are defined as before.

Preferred compounds of formula I are those which are of formula Ib. Particularly preferred are compounds of formula I which are of formula Ia.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral absorbens or eluant).

The term "asymmetric carbon atom (C*)" means a carbon atom with four different substituents. According to the Cahn-Ingold-Prelog-Convention the asymmetric carbon atom can be of the "R" or "S" configuration.

Preferred are chiral compounds of formula (Ia), wherein the carbon atom number 9a has the R configuration.

Also preferred are chiral compounds of formula (Ic),

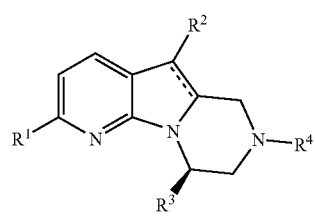
(Ic)

wherein $R^1$ to $R^4$ are defined as before. Formula (Ic) means that the asymmetric carbon atom C*

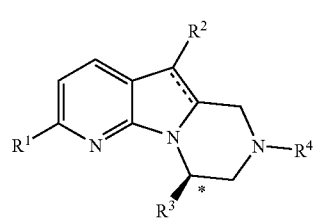
(Ic)

is of the R configuration and $R^1$ to $R^4$ are defined above, provided, however, that if $R^3$ is alkoxymethyl, preferably hydroxymethyl, then C* is of the S configuration. The $R^3$ substituent occupies an equivalent stereochemical position in the 3-dimensional space.

Further preferred compounds of formula (I) are those, wherein C* is of the R configuration and wherein R³ means alkyl.

Further preferred are those compounds according to formula (I), wherein C* is of the S configuration and R³ means alkoxymethyl, most preferably hydroxymethyl.

One preferred embodiment relates to the pharmaceutically acceptable salts of compounds of formula I. Preferred salts or compounds of formula I are the hydrochloride salts.

Additionally preferred compounds according to formula I are those, wherein R² is hydrogen or alkyl. Particularly preferred are compounds of formula I, wherein R² is hydrogen. Further particularly preferred are those compounds of formula I, wherein R² is methyl.

Further preferred are compounds of formula I, wherein R³ is alkyl, particularly methyl.

Moreover, preferred are compounds according to formula I, wherein R⁴ is hydrogen.

Preferred are compounds according to formula I, wherein R¹ is hydrogen, halogen, alkyl, cycloalkyl, alkoxycarbonylalkenyl, alkoxyalkyl, cyano, cycloalkylalkoxyalkyl, alkoxyalkoxyalkyl, amino or haloalkyl.

A further preferred aspect of the present invention are compounds of formula I, wherein R¹ is halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino or haloalkyl.

Preferred are compounds of formula I, wherein R¹ is hydrogen, chloro, bromo, methyl, ethyl, trifluoromethyl, cyclopropyl, ethoxycarbonylethenyl, methoxypropyl, cyano, cyclopropylmethoxymethyl, methoxyethoxymethyl, methoxymethyl or primary amino.

Further preferred are compounds of formula I, wherein R¹ is chloro, bromo, methyl, ethyl, trifluoromethyl, cyclopropyl, ethoxycarbonylethenyl, methoxypropyl, cyano, cyclopropylmethoxymethyl, methoxyethoxymethyl, methoxymethyl or primary amino.

Also preferred are compounds of formula I, wherein R¹ is hydroxyalkoxy, alkoxyalkoxy, hydroxyalkoxyalkyl, alkylcarbonyl, haloalkylcarbonyl, alkyl-S—, alkenyl-S—, A¹ or A².

Particularly preferred are those compounds of formula I, wherein R¹ is fluoromethyl, difluoromethyl, hydroxy-ethyl, methoxyethyl, ethoxyethyl, cyclopropylmethoxy-ethyl or allyl-S—.

Further preferred are compounds of formula I, wherein R¹ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino, haloalkyl, hydroxyalkoxy, alkoxyalkoxy, hydroxyalkoxyalkyl, alkylcarbonyl, haloalkylcarbonyl, alkyl-S— or alkenyl-S—.

Further preferred are compounds of formula I, wherein R¹ is A¹ and particularly, wherein $R^a$ is hydrogen, alkyl, cycloalkyl or cycloalkylalkyl; $R^b$ is hydrogen or alkyl; and $R^c$ is haloalkyl, alkyl, alkoxyalkyl or thiazolyl.

Also preferred are compounds of formula I, wherein $R^a$ is hydrogen or methyl.

Further preferred are compounds of formula I, wherein $R^b$ is hydrogen or alkyl.

Another preferred aspect of the invention are compounds of formula I, wherein $R^c$ is trifluoromethyl or methyl.

Also preferred are those compounds of formula I, wherein R¹ is A² and particularly, wherein $R^d$ is alkyl, cycloalkyl, aryl, aralkyl or alkenyl; $R^e$ is hydrogen or alkyl; $R^f$ is hydrogen or alkyl; and $R^g$ is hydrogen or alkyl.

Preferred are those compounds of formula I, wherein $R^f$ and $R^g$ are hydrogen.

Also preferred are the compounds of formula I, wherein $R^d$ is alkyl, cyclohexyl, phenyl, benzyl or allyl.

Further preferred are the compounds of formula I, wherein $R^e$ is hydrogen.

Examples of preferred compounds of formula I are:
1. (R)-6-Chloro-4-methyl-1,2,3,4-tetrahydro-2,4a,5-triaza-fluorene;
2. (4R,9aR)-6-Chloro-4-methyl-1,2,3,4,9,9a-hexahydro-2,4a,5-triaza-fluorene;
3. (4R,9aS)-6-Chloro-4-methyl-1,2,3,4,9,9a-hexahydro-2,4a,5-triaza-fluorene;
4. (R)-6-Bromo-4-methyl-1,2,3,4-tetrahydro-2,4a,5-triaza-fluorene;
5. (4R,9aR)-6-Bromo-4-methyl-1,2,3,4,9,9a-hexahydro-2,4a,5-triaza-fluorene;
6. (4R,9aS)-6-Bromo-4-methyl-1,2,3,4,9,9a-hexahydro-2,4a,5-triaza-fluorene;
7. (R)-4,6-Dimethyl-1,2,3,4-tetrahydro-2,4a,5-triaza-fluorene;
8. (4R,9aR)-4,6-Dimethyl-1,2,3,4,9,9a-hexahydro-2,4a,5-triaza-fluorene;
9. (4R,9aR)-6-Ethyl-4-methyl-1,2,3,4,9,9a-hexahydro-2,4a,5-triaza-fluorene;
10. (4R,9aR)-4-Methyl-6-trifluoromethyl-1,2,3,4,9,9a-hexahydro-2,4a,5-triaza-fluorene;
11. (4R,9aR)-6-Cyclopropyl-4-methyl-1,2,3,4,9,9a-hexahydro-2,4a,5-triaza-fluorene;
12. (4R,9aR)-3-(4-Methyl-1,2,3,4,9,9a-hexahydro-2,4a,5-triaza-fluoren-6-yl)-acrylic acid ethyl ester;
13. (4R,9aR)-6-(3-Methoxy-propyl)-4-methyl-1,2,3,4,9,9a-hexahydro-2,4a,5-triaza-fluorene;
14. (4R,9aR)-4-Methyl-1,2,3,4,9,9a-hexahydro-2,4a,5-triaza-fluorene-6-carbonitrile;
15. (4R,9aR)-6-Cyclopropylmethoxymethyl-4-methyl-1,2,3,4,9,9a-hexahydro-2,4a,5-triaza-fluorene;
16. (4R,9aR)-6-(2-Methoxy-ethoxymethyl)-4-methyl-1,2,3,4,9,9a-hexahydro-2,4a, 5-triaza-fluorene;
17. (4R,9aR)-6-Methoxymethyl-4-methyl-1,2,3,4,9,9a-hexahydro-2,4a,5-triaza-fluorene;
18. (R)-4-Methyl-1,2,3,4,9,9a-hexahydro-2,4a,5-triaza-fluorene;
19. (4R,9aR)-4-Methyl-1,2,3,4,9,9a-hexahydro-2,4a,5-triaza-fluoren-6-ylamine;
20. (R)-6-Chloro-4,9-dimethyl-1,2,3,4-tetrahydro-2,4a,5-triaza-fluorene;
21. (4R,9aR)-6-Benzyloxy-4-methyl-1,2,3,4,9,9a-hexahydro-2,4a,5-triaza-fluorene;
22. (4R,9aR)-6-Methoxy-4-methyl-1,2,3,4,9,9a-hexahydro-2,4a,5-triaza-fluorene;
23. (4R,9aR)-6-Ethoxy-4-methyl-1,2,3,4,9,9a-hexahydro-2,4a,5-triaza-fluorene;
24. (4R,9aR)-2-(4-Methyl-1,2,3,4,9,9a-hexahydro-2,4a,5-triaza-fluoren-6-yloxy)-ethanol;
25. (4R,9aR)-6-(2-Methoxy-ethoxy)-4-methyl-1,2,3,4,9,9a-hexahydro-2,4a,5-triaza-fluorene;
26. (4R,9aR)-6-Cyclobutylmethoxymethyl-4-methyl-1,2,3,4,9,9a-hexahydro-2,4a,5-triaza-fluorene;
27. (4R,9aR)-6-Ethoxymethyl-4-methyl-1,2,3,4,9,9a-hexahydro-2,4a,5-triaza-fluorene;
28. (4R,9aR)-6-Cyclohexylmethoxymethyl-4-methyl-1,2,3,4,9,9a-hexahydro-2,4a,5-triaza-fluorene;
29. (4R,9aR)-2-(4-Methyl-1,2,3,4,9,9a-hexahydro-2,4a,5-triaza-fluoren-6-ylmethoxy)-ethanol;
30. (4R,9aR)-(4-Methyl-1,2,3,4,9,9a-hexahydro-2,4a,5-triaza-fluoren-6-yl)-methanol;

31. (4R,9aR)-6-Isobutyl-4-methyl-1,2,3,4,9,9a-hexahydro-2,4a,5-triaza-fluorene;
32. (4R,9aR)-6-Difluoromethyl-4-methyl-1,2,3,4,9,9a-hexahydro-2,4a,5-triaza-fluorene;
33. (4R,9aR)-6-Fluoromethyl-4-methyl-1,2,3,4,9,9a-hexahydro-2,4a,5-triaza-fluorene;
34. (4R,9aR)-1-(4-Methyl-1,2,3,4,9,9a-hexahydro-2,4a,5-triaza-fluoren-6-yl)-ethanone;
35. (4R,9aR)-1-(4-Methyl-1,2,3,4,9,9a-hexahydro-2,4a,5-triaza-fluoren-6-yl)-propan-1-one;
36. (4R,9aR)-1-(4-Methyl-1,2,3,4,9,9a-hexahydro-2,4a,5-triaza-fluoren-6-yl)-butan-1-one;
37. (4R,9aR)-2,2,2-Trifluoro-1-(4-methyl-1,2,3,4,9,9a-hexahydro-2,4a,5-triaza-fluoren-6-yl)-ethanone;
38. (4R,9aR)-1-(RS)-(4-Methyl-1,2,3,4,9,9a-hexahydro-2,4a,5-triaza-fluoren-6-yl)-ethanol;
39. (4R,9aR)-6-(1-(R)-Hydroxy-ethyl)-4-methyl-3,4,9,9a-tetrahydro-1H-2,4a,5-triaza-fluorene;
40. (4R,9aR)-6-(1-(S)-Hydroxy-ethyl)-4-methyl-3,4,9,9a-tetrahydro-1H-2,4a,5-triaza-fluorene;
41. (4R,9aR)-6-(1-(R)-Methoxy-ethyl)-4-methyl-1,2,3,4,9,9a-hexahydro-2,4a,5-triaza-fluorene;
42. (4R,9aR)-6-(1-(S)-Methoxy-ethyl)-4-methyl-1,2,3,4,9,9a-hexahydro-2,4a,5-triaza-fluorene;
43. (4R,9aR)-6-(1-(R)-Ethoxy-ethyl)-4-methyl-1,2,3,4,9,9a-hexahydro-2,4a,5-triaza-fluorene;
44. (4R,9aR)-6-(1-(R)-Cyclopropylmethoxy-ethyl)-4-methyl-1,2,3,4,9,9a-hexahydro-2,4a,5-triaza-fluorene;
45. (4R,9aR)-6-(1-(S)-Ethoxy-ethyl)-4-methyl-1,2,3,4,9,9a-hexahydro-2,4a,5-triaza-fluorene;
46. (4R,9aR)-6-(1-(S)-Cyclopropylmethoxy-ethyl)-4-methyl-1,2,3,4,9,9a-hexahydro-2,4a,5-triaza-fluorene;
47. (4R,9aR)-3,3,3-Trifluoro-1-(4-methyl-1,2,3,4,9,9a-hexahydro-2,4a,5-triaza-fluoren-6-yl)-(R)-propan-1-ol;
48. (4R,9aR)-3,3,3-Trifluoro-1-(4-methyl-1,2,3,4,9,9a-hexahydro-2,4a,5-triaza-fluoren-6-yl)-(S)-propan-1-ol;
49. (4R,9aR)-(R)-(4-Methyl-1,2,3,4,9,9a-hexahydro-2,4a,5-triaza-fluoren-6-yl)-thiazol-2-yl-methanol;
50. (4R,9aR)-(S)-(4-Methyl-1,2,3,4,9,9a-hexahydro-2,4a,5-triaza-fluoren-6-yl)-thiazol-2-yl-methanol;
51. (4R,9aR)-2-(4-Methyl-1,2,3,4,9,9a-hexahydro-2,4a,5-triaza-fluoren-6-yl)-propan-2-ol;
52. (4R,9aR)-3-Methyl-2-(RS)-(4-methyl-1,2,3,4,9,9a-hexahydro-2,4a,5-triaza-fluoren-6-yl)-butan-2-ol;
53. (4R,9aR)-1-Methoxy-2-(RS)-(4-methyl-1,2,3,4,9,9a-hexahydro-2,4a,5-triaza-fluoren-6-yl)-propan-2-ol;
54. (4R,9aR)-5-Chloro-2-(RS)-(4-methyl-1,2,3,4,9,9a-hexahydro-2,4a,5-triaza-fluoren-6-yl)-pentan-2-ol;
55. (4R,9aR)4-Methyl-6-(2-(RS)-methyl-tetrahydro-furan-2-yl)-1,2,3,4,9,9a-hexahydro-2,4a,5-triaza-fluorene;
56. (4R,9aR)-6-((RS)-1-Fluoro-ethyl)-4-methyl-1,2,3,4,9,9a-hexahydro-2,4a,5-triaza-fluorene;
57. (4R,9aR)-6-((RS)-1-Fluoro-propyl)-4-methyl-1,2,3,4,9,9a-hexahydro-2,4a,5-triaza-fluorene;
58. (4R,9aR)-6-((RS)-1-Fluoro-butyl)-4-methyl-1,2,3,4,9,9a-hexahydro-2,4a,5-triaza-fluorene;
59. (4R,9aR)-6-Ethylsulfanyl-4-methyl-1,2,3,4,9,9a-hexahydro-2-4a,5-triaza-fluorene;
60. (4R,9aR)-6-Allylsulfanyl-4-methyl-1,2,3,4,9,9a-hexahydro-2-4a,5-triaza-fluorene;
61. (4R,9aR)-6-Propylsulfanyl-4-methyl-1,2,3,4,9,9a-hexahydro-2-4a,5-triaza-fluorene;
62. (4R,9aR)-6-Isopropylsulfanyl-4-methyl-1,2,3,4,9,9a-hexahydro-2-4a,5-triaza-fluorene;
63. (4R,9aR)-6-(1-(RS)-Methoxy-propyl)-4-methyl-1,2,3,4,9,9a-hexahydro-2,4a,5-triaza-fluorene;
64. (4R,9aR)-6-(1-(RS)-Cyclopropylmethoxy-propyl)-4-methyl-1,2,3,4,9,9a-hexahydro-2,4a,5-triaza-fluorene;
65. (4R,9aR)-6-(1-(RS)-Methoxy-butyl)-4-methyl-1,2,3,4,9,9a-hexahydro-2,4a,5-triaza-fluorene;
66. (4R,9aR)-6-(1-(RS)-Ethoxy-butyl)-4-methyl-1,2,3,4,9,9a-hexahydro-2,4a,5-triaza-fluorene;
67. (4R,9aR)-6-(1-(RS)-Cyclopropylmethoxy-butyl)-4-methyl-1,2,3,4,9,9a-hexahydro-2,4a,5-triaza-fluorene;
68. (4R,9aR)-Isopropyl-carbamic acid 4-methyl-1,2,3,4,9,9a-hexahydro-2-4a,5-triaza-fluorene-6-ylmethyl ester;
69. (4R,9aR)-tert-Butyl-carbamic acid 4-methyl-1,2,3,4,9,9a-hexahydro-2,4a,5-triaza-fluoren-6-ylmethyl ester;
70. Cyclohexyl-carbamic acid 4-methyl-1,2,3,4,9,9a-hexahydro-2,4a,5-triaza-fluoren-6-ylmethyl ester;
71. (4R,9aR)-Ethyl-carbamic acid 4-methyl-1,2,3,4,9,9a-hexahydro-2,4a,5-triaza-fluoren-6-ylmethyl ester;
72. (4R,9aR)-Phenyl-carbamic acid 4-methyl-1,2,3,4,9,9a-hexahydro-2,4a,5-triaza-fluoren-6-ylmethyl ester;
73. (4R,9aR)-Benzyl-carbamic acid 4-methyl-1,2,3,4,9,9a-hexahydro-2,4a,5-triaza-fluoren-6-ylmethyl ester;
74. (4R,9aR)-Allyl-carbamic acid 4-methyl-1,2,3,4,9,9a-hexahydro-2,4a,5-triaza-fluoren-6-ylmethyl ester;
75. (4R,9aR)-Ethyl-carbamic acid 1-(RS)-(4-methyl-1,2,3,4,9,9a-hexahydro-2,4a,5-triaza-fluoren-6-yl)-propyl ester;
76. (4R,9aR)-Ethyl-carbamic acid 1-(RS)-(4-methyl-1,2,3,4,9,9a-hexahydro-2,4a,5-triaza-fluoren-6-yl)-butyl ester;
77. (4R,9aR)-Ethyl-carbamic acid 1-(S)-(4-methyl-1,2,3,4,9,9a-hexahydro-2,4a,5-triaza-fluoren-6-yl)-ethyl ester;
78. (4R,9aR)-Propyl-carbamic acid 1-(S)-(4-methyl-1,2,3,4,9,9a-hexahydro-2,4a,5-triaza-fluoen-6-yl)-ethyl ester;
79. (4R,9aR)-Isopropyl-carbamic acid 1-(S)-(4-methyl-1,2,3,4,9,9a-hexahydro-2,4a,5-triaza-fluoren-6-yl)-ethyl ester;
80. (4R,9aR)-Pyrrolidine-1-carboxylic acid 4-methyl-1,2,3,4,9,9a-hexahydro-2,4a,5-triaza-fluoren-6-ylmethyl ester; and
81. (4R,9aR)-Piperazine-1,4-dicarboxylic acid benzyl ester 4-methyl-1,2,3,4,9,9a-hexahydro-2,4a,5-triaza-fluoren-6-ylmethyl ester.

Examples of particularly preferred compounds of formula I are:
(4R,9aR)-6-Chloro-4-methyl-1,2,3,4,9,9a-hexahydro-2,4a,5-triaza-fluorene;
(4R,9aR)-6-Bromo-4-methyl-1,2,3,4,9,9a-hexahydro-2,4a,5-triaza-fluorene;
(R)-4,6-Dimethyl-1,2,3,4-tetrahydro-2,4a,5-triaza-fluorene;
(4R,9aR)-4,6-Dimethyl-1,2,3,4,9,9a-hexahydro-2,4a,5-triaza-fluorene;
(4R,9aR)-6-Ethyl-4-methyl-1,2,3,4,9,9a-hexahydro-2,4a,5-triaza-fluorene;
(4R,9aR)-4-Methyl-6-trifluoromethyl-1,2,3,4,9,9a-hexahydro-2,4a,5-triaza-fluorene;
(4R,9aR)-6-Cyclopropyl-4-methyl-1,2,3,4,9,9a-hexahydro-2,4a,5-triaza-fluorene;
(4R,9aR)-6-Cyclopropylmethoxymethyl-4-methyl-1,2,3,4,9,9a-hexahydro-2,4a,5-triaza-fluorene;
(4R,9aR)-6-Methoxymethyl-4-methyl-1,2,3,4,9,9a-hexahydro-2,4a,5-triaza-fluorene;
(R)-6-Chloro-4,9-dimethyl-1,2,3,4-tetrahydro-2,4a,5-triaza-fluorene;
(4R,9aR)-6-Difluoromethyl-4-methyl-1,2,3,4,9,9a-hexahydro-2,4a,5-triaza-fluorene;
(4R,9aR)-6-Fluoromethyl-4-methyl-1,2,3,4,9,9a-hexahydro-2,4a,5-triaza-fluorene;
(4R,9aR)-6-(1-(S)-Hydroxy-ethyl)-4-methyl-3,4,9,9a-tetrahydro-1H-2,4a,5-triaza-fluorene;

(4R,9aR)-6-(1-(S)-Methoxy-ethyl)-4-methyl-1,2,3,4,9,9a-hexahydro-2,4a,5-triaza-fluorene;
(4R,9aR)-6-(1-(S)-Ethoxy-ethyl)-4-methyl-1,2,3,4,9,9a-hexahydro-2,4a,5-triaza-fluorene;
(4R,9aR)-6-(1-(S)-Cyclopropylmethoxy-ethyl)-4-methyl-1,2,3,4,9,9a-hexahydro-2,4a,5-triaza-fluorene; and
(4R,9aR)-6-Allylsulfanyl-4-methyl-1,2,3,4,9,9a-hexahydro-2-4a,5-triaza-fluorene.

Another embodiment of the current invention relates to processes for the manufacture of the compounds of formula I. The substituents and indices used in the following schemes have the significance given above unless otherwise indicated.

In case $R^3$ is hydroxyalkyl the hydroxy group can be protected in the following reactions by methods known to one skilled in the art, such as for example, with tert-butyl-dimethylsilyl.

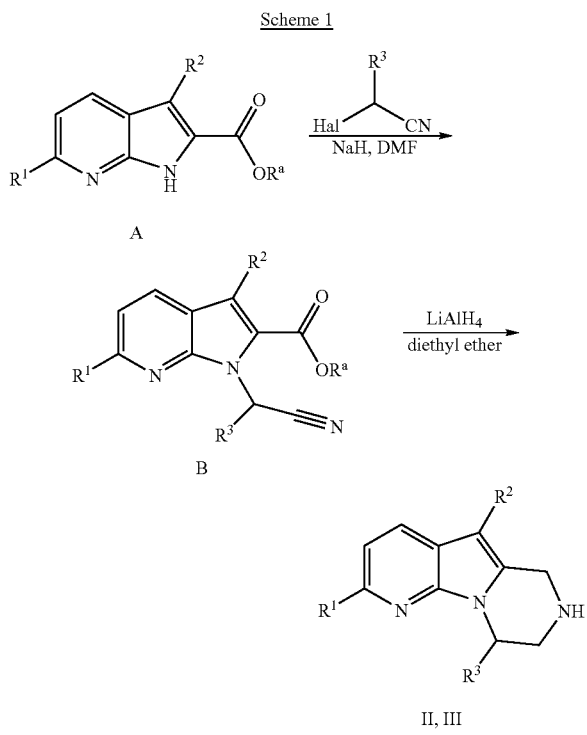

Scheme 1

1,2,3,4-Tetrahydro[2,4a,5]triaza-fluorenes of formula II and III can be prepared according to scheme 1 by a process where the 7-aza-indole-2-carboxylate of formula A is first reacted with an alpha halo alkanenitrile (e.g., 2-bromo propionitrile) in a suitable solvent (e.g., DMF) with a suitable base (e.g., sodium hydride). Compounds of formula II correspond to compounds of formula I, wherein $R^2$ and $R^4$ are hydrogen. Compounds of formula III correspond to compounds of formula I, wherein $R^2$ is alkyl or alkoxy and $R^4$ is hydrogen.

The intermediate B is reduced and cyclized to the tetrahydro[2,4a,5]triaza-fluorene II or III by reaction with a suitable reducing agent in a suitable solvent (e.g., LiAlH$_4$ in THF or diethyl ether). $R^a$ in scheme 1 is an alkyl group, preferably a lower alkyl group, preferably methyl or ethyl.

Preparation of Compounds According to Formula A:
Compound of formula A, wherein $R^1$ is hydrogen or halogen, particularly chlorine are described in WO 0044753.

Compounds of formula A, wherein $R^1$ is defined as before with the proviso that $R^1$ is not hydrogen can be obtained by an analogous process as described in WO 0044753 by, e.g. oxidation of the pyridine nitrogen to the N-oxide under appropriate oxidizing conditions, such as meta-chloroperoxybenzoic acid in dichloromethane and treatment of the N-oxide with a nucleophilic system, such as neat acetic acid anhydride or benzoic acid bromide in the presence of a suitable base, like e.g. hexamethyldisilazane in a suitable solvent such as, e.g. tetrahydrofuran. The indole nitrogen can be optionally protected in this process, preferably with a Boc group.

Compound of formula A, wherein $R^1$ is as defined above with the proviso that $R^1$ is not halogen, can also be obtained by analogous process as described in Synthesis 1996, 877 from N-protected (preferably Boc) 3-alkyl-2-aminopyridines, through double deprotonation with a base, such as n-butyllithium in a suitable solvent like, e.g. tetrahydrofuran and subsequent treatment of the intermediate with diethyloxalate and dehydration of the resulting adduct under acidic conditions, e.g. with hydrochloric acid in an appropriate alcohol, such as, e.g. ethanol.

Compounds according to formula A, particularly in case $R^2$ is alkoxy, can also be synthesized in a process where 2-(ethoxycarbonylmethyl-amino)-nicotinic acid ethyl esters, which can be obtained by, e.g. reaction of 2-amino-nicotinic acid ethyl ester with glyoxal and perchloric acid in ethanol, are cyclized to the corresponding 3-hydroxy-1H-pyrrolo[2,3-b]pyridine-2-carboxylic acid ethyl esters which in turn are alkylated with suitable alkylating agents in an appropriate solvent (e.g. ethyl iodide in tetrahydrofuran).

Alpha halo alkanenitriles can be either purchased from commercial sources or synthesized from, e.g. reaction of acrylonitrile with bromoalkanes under UV irradiation in the presence of, e.g. triphenylphosphine and a suitable catalyst such as copper(I)chloride in an appropriate solvent like, e.g. tetrahydrofuran (analogous to the process described in J. Am. Chem. Soc. 1983, 105(22), 6719). Alpha halo alkanenitriles can also be prepared in a process, where an alkoxy-acetonitrile derivative is irradiated in the presence of a suitable brominating agent like, e.g. N-bromosuccinimide in tetrahydrofuran (analogous to the process described in J. Org. Chem. 1976, 14 (17), 2846). In the case of $R^3$ is hydroxymethyl the free OH group is protected.

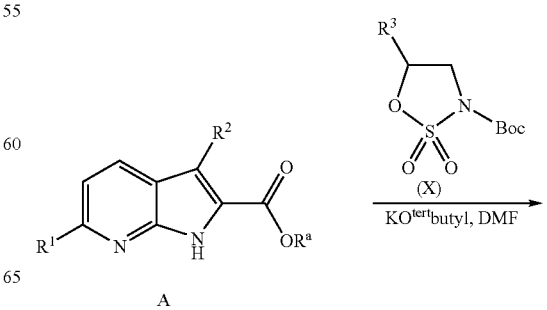

Scheme 2

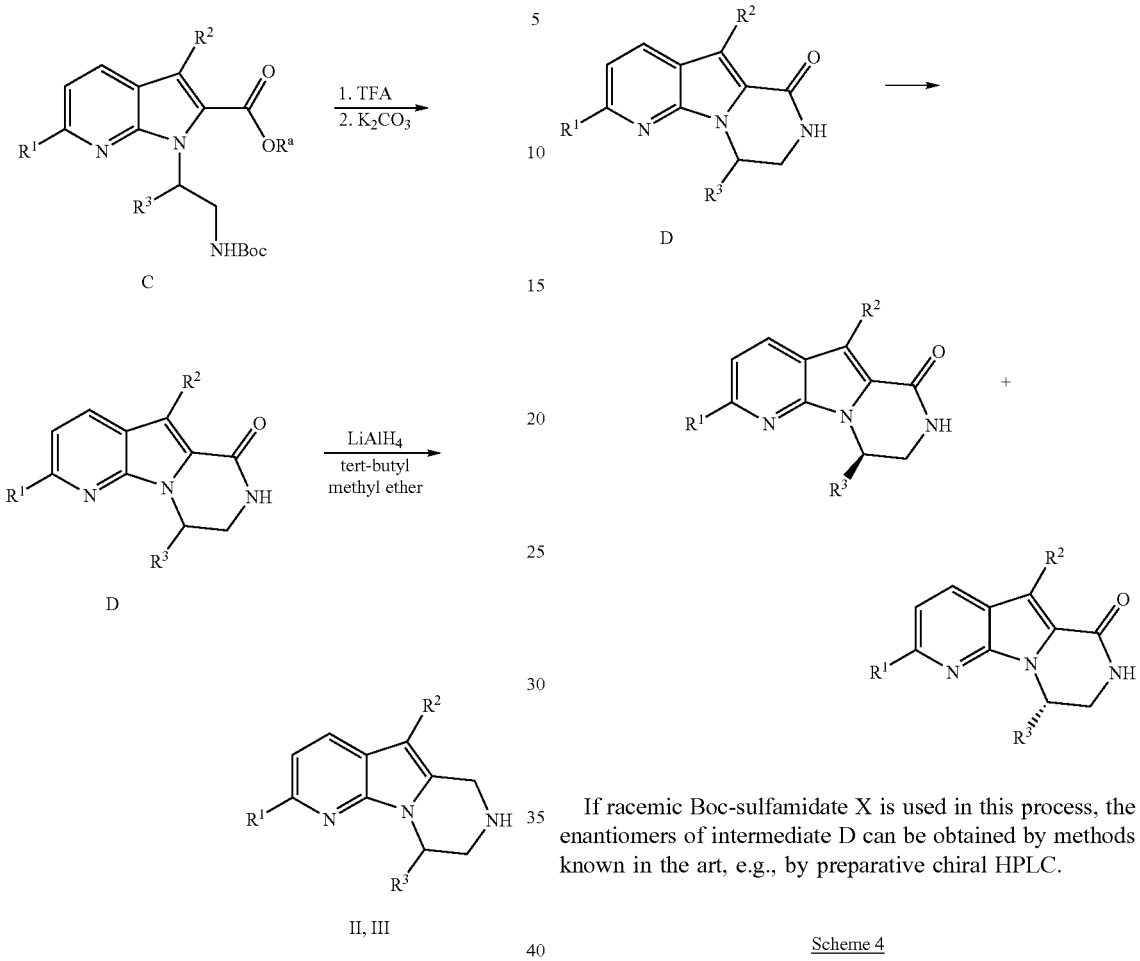

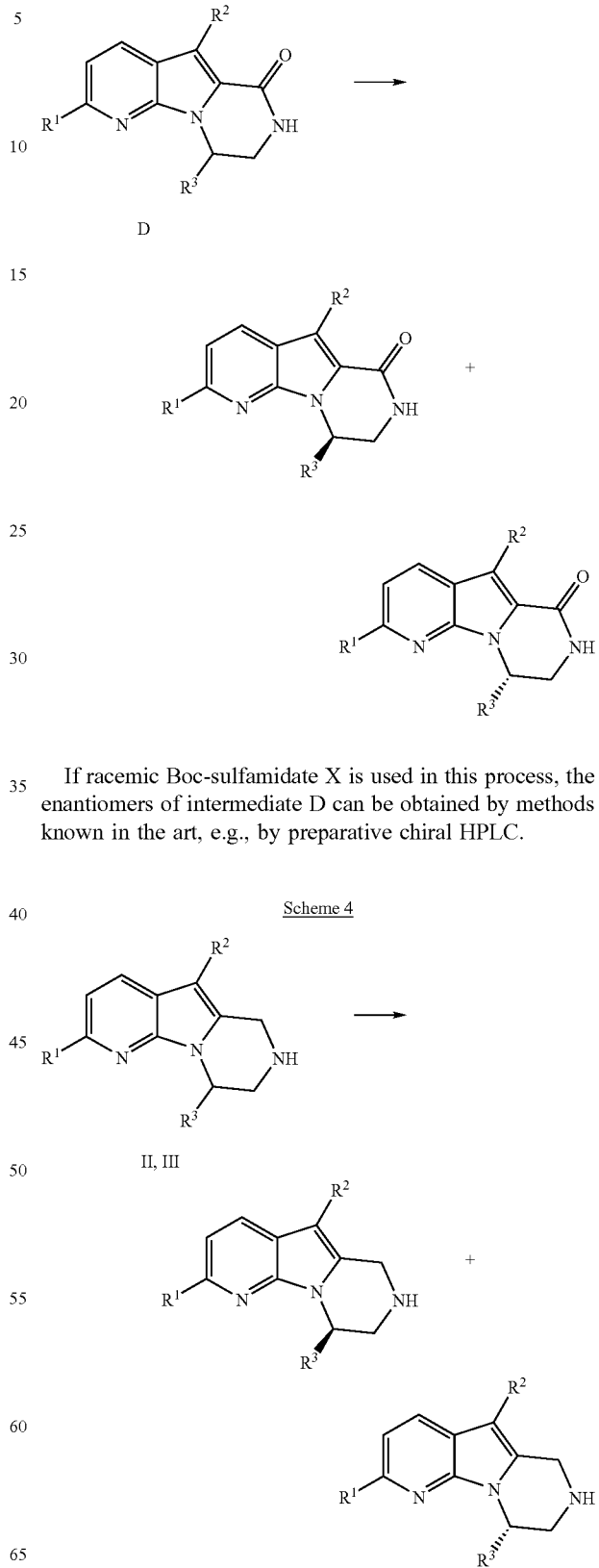

1,2,3,4-Tetrahydro[2,4a,5]triaza-fluorenes of formula II and III can also be prepared according to scheme 2 by a process where the 7-aza-indole-2-carboxylate of formula A is first reacted with the Boc-sulfamidate X in a suitable solvent (e.g., DMF) with a suitable base (e.g., potassium tert-butylate or sodium hydride) followed by removal of the Boc protecting group (Boc means tert-butoxycarbonyl) with a suitable reagent e.g. trifluoroacetic acid (TFA) and ring closure in the presence of base (e.g., potassium carbonate). The stereochemistry of the carbon atom attached to $R^3$ in Boc-sulfamidate X is inverted (>90% e.e.) in this reaction sequence. The intermediate amide D is reduced with a suitable reducing agent in a suitable solvent (e.g., LiAlH$_4$ in tert-butyl methyl ether or borane-dimethylsulfide complex in THF). $R^a$ in scheme 2 is an alkyl group, preferably a lower alkyl group, preferably methyl or ethyl. In case $R^3$ means hydroxyalkyl the corresponding hydroxy group can be protected by, e.g. a tert-butyl-dimethylsilyl group. Compounds II and III are defined as in scheme 1.

Chiral compounds according to formulae II and III can e.g. be obtained as follows:

If racemic Boc-sulfamidate X is used in this process, the enantiomers of intermediate D can be obtained by methods known in the art, e.g., by preparative chiral HPLC.

The enantiomers of 1,2,3,4-tetrahydro[2,4a,5]triaza-fluorenes II and III can be obtained either by using a chiral sulfamidate X or by separation of the enantiomers by preparative chiral HPLC or by crystallization with suitable chiral acids, separation of the diastereomeric salts and isolation of the enantiomers from these salts. An alternative access to the enantiomers of 1,2,3,4-tetrahydro[2,4a,5]triaza-fluorenes II and III involves the separation of the enantiomers of the precursor C, e.g., by preparative chiral HPLC.

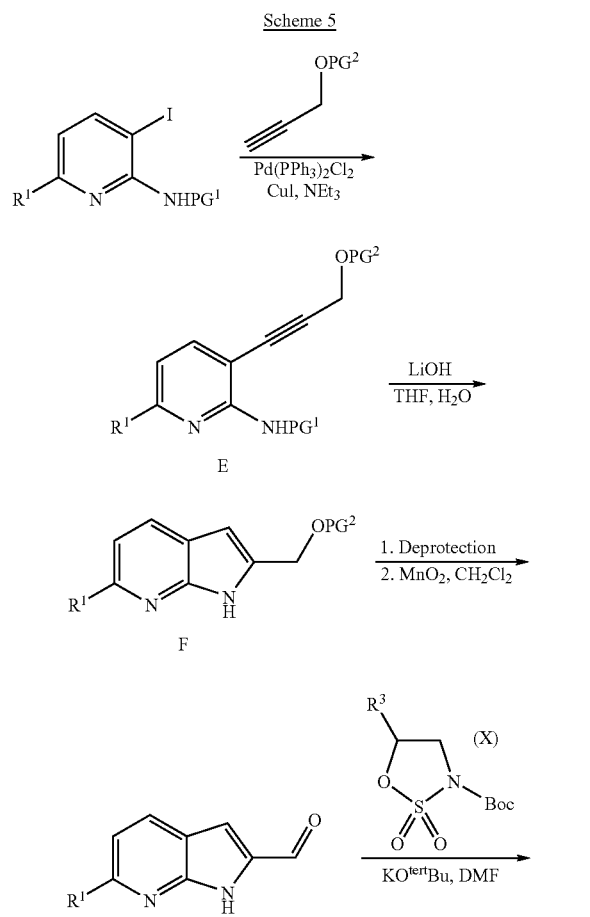

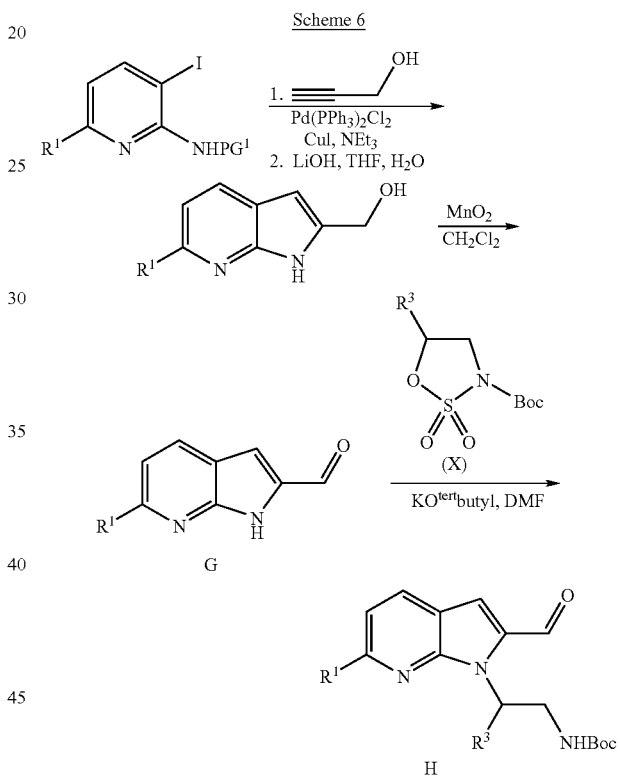

7-Aza-indole derivatives H can be prepared according to scheme 5, starting from protected o-iodoanilines ($PG^1$ means a suitable protective group such as e.g. N-methoxycarbonyl) by cross-coupling reaction with suitably substituted and optionally protected carbinols (preferred protective groups $PG^2$ are silyl ethers, especially preferred is tert-butyl-dimethylsilyl). The reaction proceeds in the presence of a suitable catalyst (e.g., bis-triphenylphosphine palladium dichloride and copper(I)iodide as co-catalyst) in a suitable solvent (e.g. triethylamine). The intermediate E is treated with a base (e.g. LiOH in THF/water) to yield the indole derivative F. After deprotection (e.g., with tetrabutylammonium fluoride) in a suitable solvent (e.g., THF), the resulting alcohol is oxidized (e.g., with manganese dioxide in dichloromethane), to yield the indole derivative G. Alkylation of G with the Boc-sulfamidate X in a suitable solvent (e.g., DMF) in the presence of a suitable base (e.g., sodium hydride or potassium tert-butylate) leads to intermediate H. The stereochemistry of the carbon atom attached to $R^3$ in Boc-sulfamidate X is inverted (>90% e.e.) in this reaction sequence.

Alternatively, compounds of formula H can be prepared according to scheme 6 below:

7-Aza-indole derivatives H can also be prepared according to scheme 6, starting from protected o-iodoanilines (a suitable protective group, PG1, is, e.g. N-methoxycarbonyl) by cross-coupling reaction with propargyl alcohol derivatives in the presence of a suitable catalyst (e.g., bis-triphenylphosphine palladium dichloride and copper(I)iodide as co-catalyst) in a suitable solvent (e.g. triethylamine), followed by treatment with a base (e.g. LiOH in THF/water). The alcohol intermediate is oxidized, e. g. with manganese dioxide in dichloromethane, to yield the indole derivative G. Alkylation of G with the Boc-sulfamidate X in a suitable solvent (e.g., DMF) in the presence of a suitable base (e.g., potassium tert-butylate or sodium hydride) leads to intermediate H. The stereochemistry of the carbon atom attached to $R^3$ in Boc-sulfamidate X is inverted (>90% e.e.) in this reaction sequence.

Scheme 7

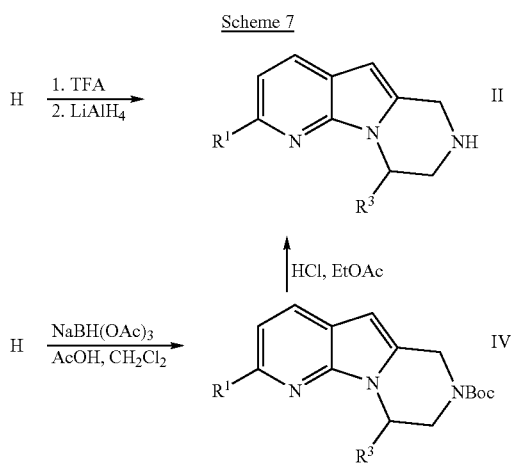

As described in scheme 7, the intermediates of formula H can be further processed to compounds of formula II by either removal of the Boc protecting group (e.g., with trifluoroacetic acid) to yield an imine intermediate which is not isolated but reduced directly with lithium aluminum hydride to yield II as a separable mixture of epimers, or direct reductive amination (e.g., with sodium triacetoxyborohydride, molecular sieves and acetic acid in a suitable solvent, e.g., dichloromethane) to yield compound IV, followed by removal of the protecting group (e.g., with hydrochloric acid in ethyl acetate).

Scheme 8

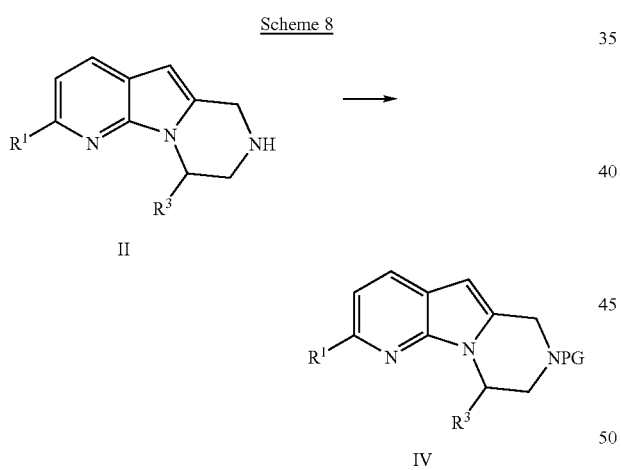

A variety of substituents $R^2$, preferably those functional groups that do not tolerate the methods described for the 1,2,3,4-tetrahydro[2,4a,5]triaza-fluorenes synthesis can be introduced starting from 1,2,3,4-tetrahydro[2,4a,5]triaza-fluorene IV according to scheme 8. To that end, the amine nitrogen of II may be protected, e.g., as the tert-butyl carbamate, to generate compounds of formula IV.

Scheme 9

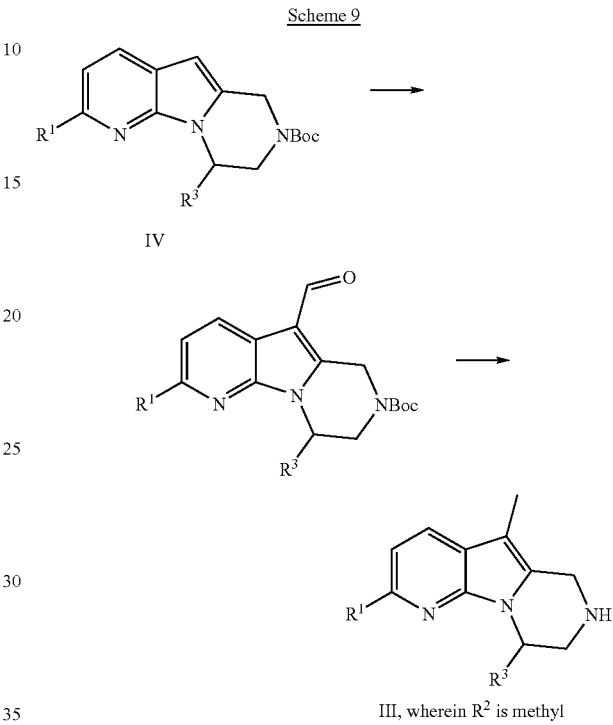

1,2,3,4-Tetrahydro[2,4a,5]triaza-fluorenes of formula III in which $R^2$ equals a methyl substituent can also be prepared as depicted in scheme 9 from intermediate IV by a two step process where an aldehyde moiety is first introduced by, e.g. a Vilsmeier-Haack formylation reaction and subsequent reduction of the formyl intermediate under suitable conditions (e.g., triethylsilane and trifluoroacetic acid in dichloromethane). Under these conditions the protective group may also be cleaved-off, e.g. if it is a tert-butyl carbamate group.

Scheme 10

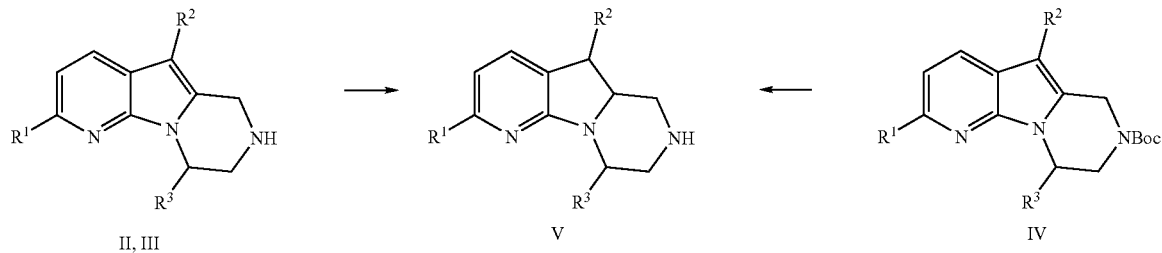

The hexahydro[2,4a,5]triaza-fluorene derivatives of formula V can be prepared as described in scheme 10 from compounds of formula II or III (analogous to WO 0044753) or IV by reduction with suitable reducing agents in suitable solvents or solvent mixtures (e.g. THF/TFA or NaCNBH₃ in acetic acid, respectively). Compounds of formula V may also be prepared from compounds of formula II or III (analogous to WO 0044753) by simultaneous reduction and deprotection of the tert-butoxy carbonyl group with suitable reducing agents in suitable acidic solvents or solvent mixtures (e.g. THF/TFA).

Compounds of formula Ia can also be prepared as shown in scheme 11 below:

Hexahydro[2,4a,5]triaza-fluorene derivatives of formula Ia can also be prepared as depicted in scheme 11 from intermediate J where the indole moiety is reduced with magnesium in methanol to produce indoline-amide K, which is then reduced under suitable conditions (e.g., LiAlH₄ in diethyl ether).

Scheme 11

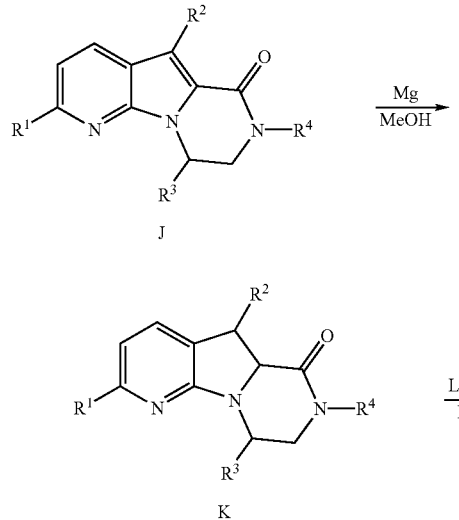

Scheme 12

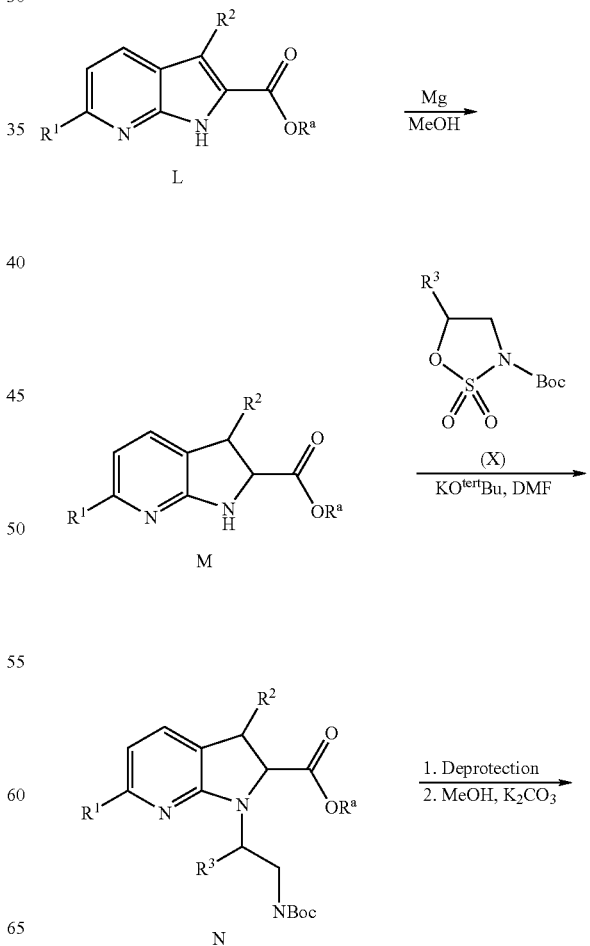

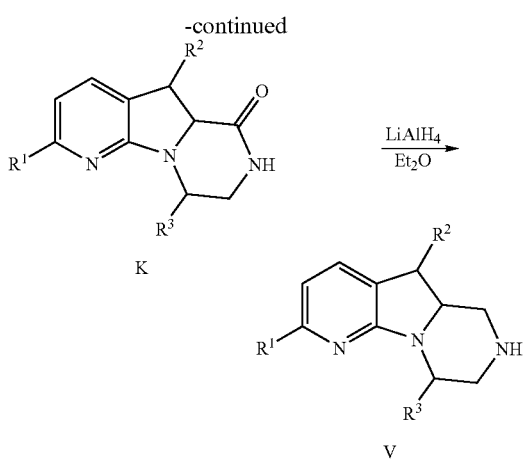

Compounds V can alternatively be prepared as depicted above in scheme 12. Indole intermediates L are reduced with a suitable reducing agent (e.g., magnesium in methanol). The indoline derivative M is alkylated with an alkylating agent such as, e.g. the sulfamidate X in the presence of a suitable base like, e.g. sodium hydride in a suitable solvent such as N,N-dimethylformamide. Intermediate K can be prepared by sequential treatment of intermediate N with an acid (e.g. trifluoroacetic acid in dichloromethane) followed by a base like, e.g. potassium carbonate in methanol. Reduction of intermediate K with a suitable reducing agent such as lithium aluminum hydride in a suitable solvent such as, e.g. tetrahydrofuran or diethyl ether yields derivatives V. In case $R^3$ means hydroxyalkyl the corresponding hydroxy group can be protected by e.g. a tert-butyl-dimethylsilyl group.

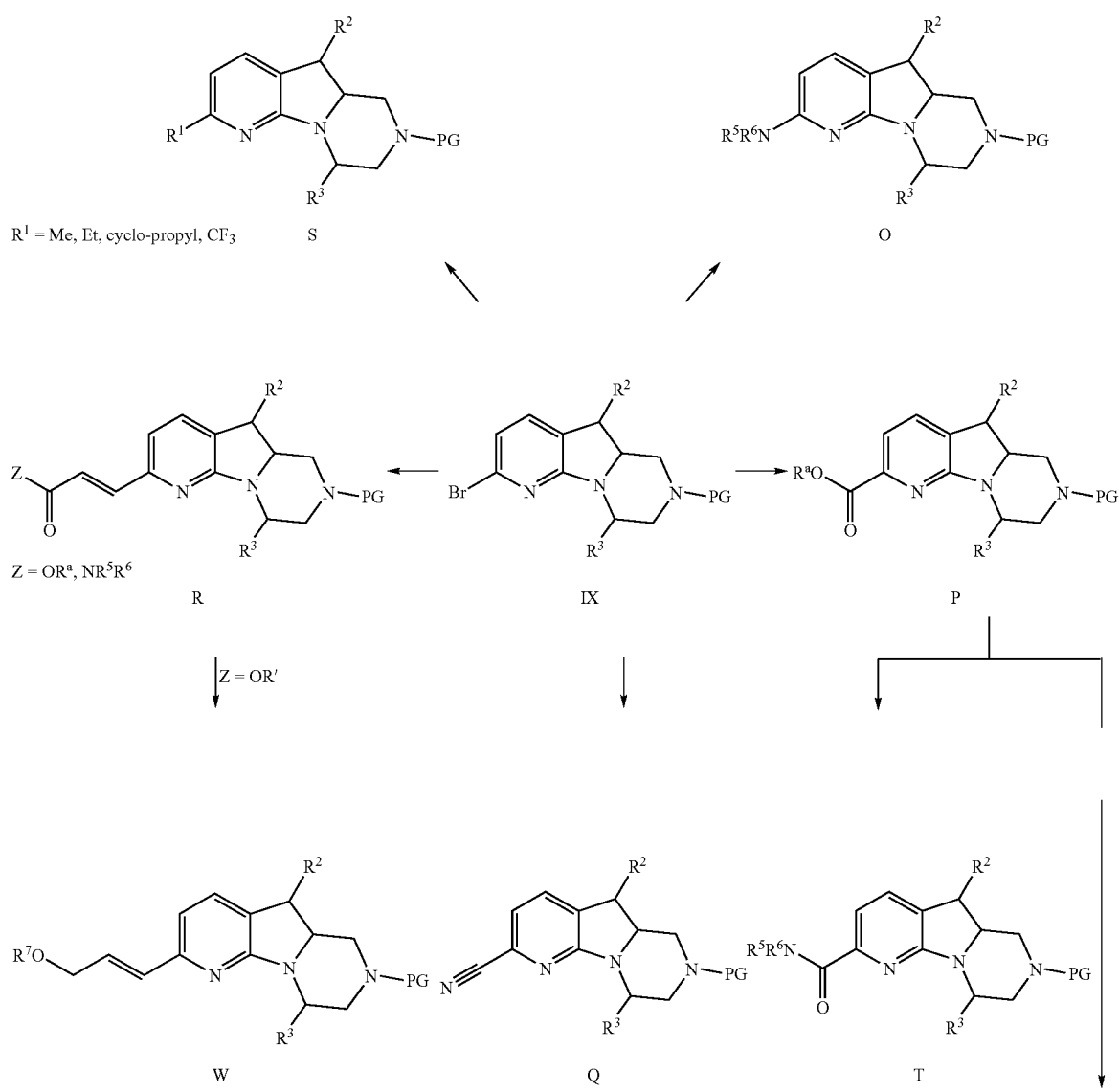

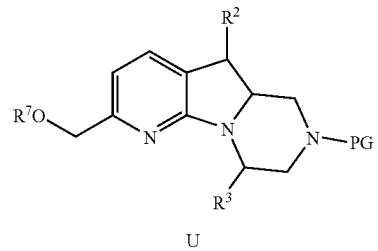

U

PG means a protective group compatible with the chemical transformation, e.g. as described in T. W. Greene and P. G. M. Wuts, Protective groups in organic synthesis, 2$^{nd}$ edition, pp. 309; preferably Boc.

R$^a$ is defined as before and R$^7$ is alkyl, aryl, cycloalkyl, alkoxyalkyl or aryloxyalkyl.

R$^5$ and R$^6$ are hydrogen or alkyl or R$^5$ and R$^6$ together with the N atom to which they are attached form a ring, such as morpholin-1-yl, pyrrolidinyl or piperidinyl.

Compounds according to formula IX can be obtained according to scheme 2 and following reduction according to scheme 10.

A variety of substituents R$^1$, preferably those functional groups that do not tolerate the methods described for the hexahydro[2,4a,5]triaza-fluorene synthesis can be introduced starting from the hexahydro[2,4a,5]triaza-fluorene derivative IX.

Several examples for the elaboration of compound IX are highlighted in scheme 13 above.

a) Amine derivatives O (by, e.g. cross-coupling reaction with benzophenone imine in the presence of a base like, e.g. sodium tert-butoxide and an appropriate catalyst like, e.g. tris(dibenzylideneacetone)dipalladium chloroform complex and R-(+)-2,2'-bis(diphenylphosphino)-1,1'-binaphthalene as ligand in a suitable solvent like, e.g. toluene and cleavage of the imine functionality (with, e.g. palladium on charcoal and ammonium formate in methanol). The amine substituent can be further alkylated or converted into amides or sulfonamides by methods known in the art. In the case where the substituents R$^5$ and R$^6$ together form a ring like in, e.g. morpholine, the substituent can be introduced with, e.g. palladium(II) acetate, 2,2'-dihydroxy-1,1'-dinaphthyl, sodium tert-butylate and morpholine in toluene.

b) Ester-substituted derivatives P (e.g. via bromine-lithium exchange, quenching the lithium intermediate with carbon dioxide and esterification of the acid) or via carbonylation reactions (e.g. under a carbon monoxide atmosphere with a suitable catalyst like, e.g. bis(triphenylphosphine)palladium(II) chloride in an appropriate alcohol like, e.g. methanol or ethanol in the presence of a base like, e.g. triethylamine), which can be further converted into amides (T) or reduced to benzylic alcohols (U), the latter again can be alkylated or arylated by methods known to those skilled in the art.

c) Cyano derivative Q (e.g. with copper(I)cyanide and tetraethylammonium cyanide, tris(dibenzylideneacetone) dipalladium(0) as catalyst and 1,1'-bis(diphenylphosphino)ferrocene as ligand in dioxane), which can be further reduced to the benzylic amine, which in turn can be alkylated and acylated, respectively by methods known to those skilled in the art.

d) α,β-Unsaturated ester derivatives R (e.g. through cross-coupling reaction with ethyl acrylate with allylpalladium chloride dimer as catalyst, an appropriate base like, e.g. sodium acetate and tri(o-tolyl)phosphine as ligand in toluene), which can be further derivatized to yield α,β-unsaturated amides, or reduced to the allylic alcohol (W, R$^7$ is H) derivative which again can be optionally alkylated by methods known to those skilled in the art.

e) Alkyl, trifluoromethyl, or cyclopropyl derivatives S (For example, a methyl group can be introduced through cross-coupling reaction with trimethylboroxine in the presence of a catalyst like, e.g. tetrakis(triphenylphosphine) palladium(0) and an appropriate base like, e.g. sodium carbonate in a solvent mixture like, e.g. dimethoxyethane and water. A trifluoromethyl substituent can be introduced through reaction of intermediate IX with, e.g. trifluoroacetate and copper(I)iodide in an appropriate solvent like, e.g. 1-methyl-2-pyrrolidone. A cyclopropyl substituent can be introduced for example through palladium-catalyzed (e.g. tetrakis(triphenylphosphine) palladium(0)) reaction of IX with a pre-formed complex of 9-borabicyclo[3.3.1]nonane and propargylbromide in the presence of an appropriate base like, e.g. sodium hydroxide in an appropriate solvent like, e.g. tetrahydrofuran.

Scheme 14

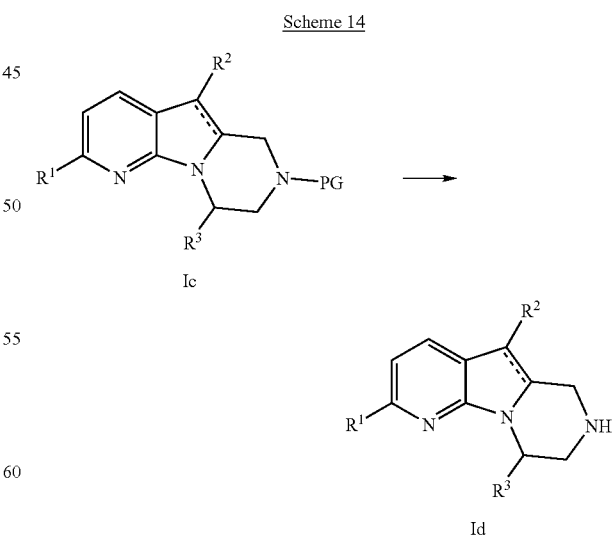

Cleavage of the protective group in compounds according to formula Ic, wherein PG means a protecting group, preferably Boc, can be performed, e.g. with acid such as trifluoroacetic acid or hydrogen chloride in a suitable solvent such as ethyl acetate in order to obtain a compound of formula Id.

Scheme 15

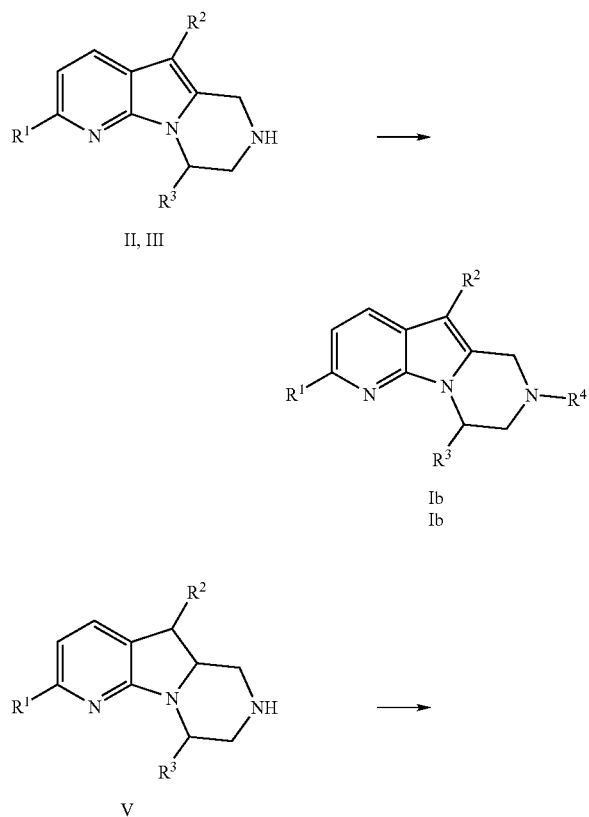

The tetra- and hexahydro[2,4a,5]triaza-fluorenes of formula Ib and Ia can be prepared from compounds of formula II, III and V, respectively, by methods known in the art (e.g. March, Advanced Organic Chemistry, 4 th. edition, page 411ff, 768ff, 898ff, 900ff, 1212ff.), e.g. alkylation reactions (e.g. with $R^4$—Br under basic conditions), Mannich reactions or acylation followed by reduction etc.

Scheme 16

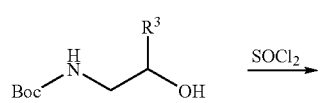

-continued

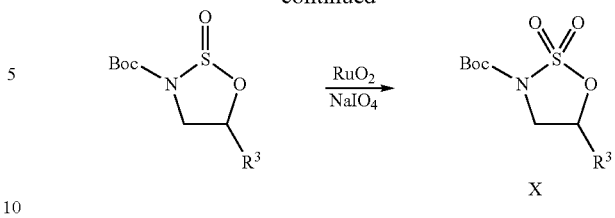

The Boc-sulfamidate X can be prepared according to scheme 16 by treating Boc-protected ethanolamine derivatives with thionyl chloride in a suitable solvent e.g. THF or ethyl acetate in the presence of a suitable base e.g. triethylamine or imidazole and oxidizing the intermediate (e.g., with sodium metaperiodate and ruthenium(IV)oxide) in a suitable solvent (e.g., ethyl acetate). Where $R^3$ is not hydrogen, the stereochemistry of the carbon atom attached to $R^3$ remains unchanged (e.e. >97%) over this sequence.

As mentioned above, one embodiment of the current invention relates to the use of compounds of formula I, or their pharmaceutically acceptable salts, solvates or esters, to treat illnesses that are caused by disorders associated with the 5-$HT_2$ receptors, specifically the 5-$HT_{2A}$, 5-$HT_{2B}$ and 5-$HT_{2C}$ receptor subtypes, more particularly the 5-$HT_{2C}$ receptor subtype.

The invention also relates to pharmaceutical compositions comprising a therapeutically effective amount of a compound of formula I, or a pharmaceutically acceptable salt, solvate or ester thereof, and a therapeutically inert carrier.

The present invention also relates to a method for the treatment and prophylaxis of eating disorders and obesity comprising administering to a patient in need of such therapy a therapeutically effective amount of a compound of formula I.

In another embodiment, the invention relates to the use of a compound of formula I, or a pharmaceutically acceptable salt, solvate or ester thereof, for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance.

It is a further particularly preferred object of the invention to provide a pharmaceutical composition comprising a compound of formula I, or a pharmaceutically acceptable salt, solvate or ester thereof, for the treatment of Type II diabetes (non-insulin dependent diabetes mellitus (NIDDM)).

Another embodiment of the invention relates to a pharmaceutical composition for the treatment of disorders of the central nervous system, cardiovascular disorders, gastrointestinal disorders, diabetes insipidus and sleep apnoea, comprising a therapeutically effective amount of a compound of formula I, or a pharmaceutically acceptable salt, solvate or ester thereof, and an inert carrier.

Particularly an object of the invention is a composition to treat disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A further preferred embodiment of the present invention is a composition as above-described to treat thrombosis.

Also preferred is the aforementioned use of the compounds according to formula I, wherein the gastrointestinal disorder is dysfunction of gastrointestinal motility.

A further object of the invention are compounds in accordance with formula I, when manufactured according to the processess described herein.

A further embodiment of the present invention is a method for the treatment and prophylaxis of disorders of the central nervous system, cardiovascular disorders, gastrointestinal disorders, diabetes insipidus and sleep apnoea, which method comprises administering an effective amount of a compound of formula I as described.

Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

Preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), diabetes insipidus, hyperglycemia, diabetic complications and insulin resistance, which method comprises administering an effective amount of a compound in accordance with formula I.

Particularly preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), hyperglycemia, diabetic complications and insulin resistance, which method comprises administering an effective amount of a compound in accordance with formula I.

It is a preferred object of the invention to provide a method for the treatment and prophylaxis of eating disorders and obesity, which method comprises administering an effective amount of a compound of formula I.

It is a preferred object of the invention to provide a method for the treatment and prophylaxis of Type II diabetes (non-insulin dependent diabetes mellitus (NIDDM), which method comprises administering an effective amount of a compound of formula I.

It is a further preferred object of the invention to provide a method of treatment of obesity in a human which comprises administration of a therapeutically effective amount of a compound according to formula I and a therapeutically effective amount of a lipase inhibitor, particularly, wherein the lipase inhibitor is orlistat. Also an object of the invention is the method as described above for the simultaneous, separate or sequential administration.

It is a further preferred object to provide a method of treatment of Type II diabetes (non-insulin dependent diabetes mellitus (NIDDM) in a human which comprises administration of a therapeutically effective amount of a compound according to formula I and a therapeutically effective amount of a lipase inhibitor, particularly, wherein the lipase inhibitor is orlistat. Also an object of the invention is the method as described above for the simultaneous, separate or sequential administration of a compound according to formula I and a lipase inhibitor, particularly orlistat.

It is a further preferred object of the invention to provide a method of treatment of diabetes mellitus (L)M), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

It is a further particularly preferred object of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

A further object of the invention is the use of a compound of formula I in the manufacture of a medicament for the treatment and prevention of obesity in a patient who is also receiving treatment with a lipase inhibitor and particularly, wherein the lipase inhibitor is orlistat.

A further object of the invention is the use of a compound of formula I in the manufacture of a medicament for the treatment and prevention of Type II diabetes (non-insulin dependent diabetes mellitus (NIDDM)) in a patient who is also receiving treatment with a lipase inhibitor and particularly, wherein the lipase inhibitor is orlistat.

A further preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a patient who is also receiving treatment with a lipase inhibitor particularly, wherein the lipase inhibitor is orlistat.

A further particularly preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a patient who is also receiving treatment with a lipase inhibitor particularly, wherein the lipase inhibitor is orlistat.

It is also an object of the invention to provide a pharmaceutical composition comprising a compound of formula I, a therapeutically inert carrier and a therapeutically effective amount of a lipase inhibitor, particularly, wherein the lipase inhibitor is orlistat.

Other combinations which may be considered are Sibutramine comprising combinations.

It is also a preferred object of the invention to provide a method of treatment and/or prevention in mammals disorders where a reduction of the blood glucose concentration is beneficial comprising administering a therapeutically effective amount of a compound of formula I. Particularly preferred is this use or method wherein the disorders are disorders involving elevated plasma blood glucose.

The compounds of formula (I) may be used in the treatment (including prophylactic treatment) of disorders associated with 5-HT$_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

A further preferred embodiment of the present invention is a process for the preparation of a compound of formula I, comprising any one of the following reactions:

a) reduction of a compound of formula B to obtain a compound of formula Ib

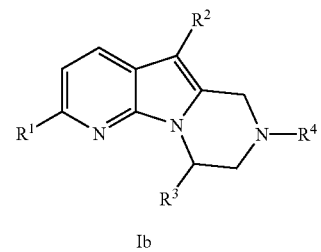

Ib wherein $R^1$ to $R^3$ are defined as in claim 1, $R^4$ means hydrogen and $R^a$ means alkyl, preferably methyl or ethyl; a preferred reducing agent is e.g. LiAlH$_4$, particularly in THF or diethyl ether; or b) reduction of a compound of formula D, preferably with e.g. LiAlH$_4$, particularly in tert-butyl methyl ether or borane-dimethylsulfide complex in THF to obtain a compound of formula Ib

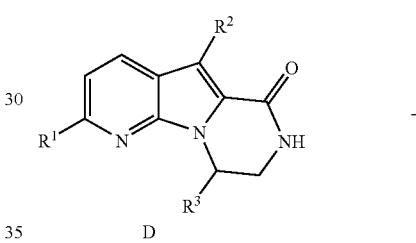

D

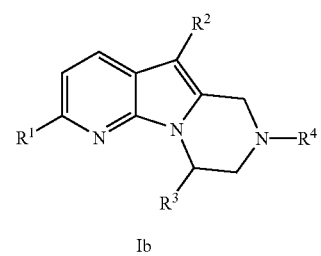

Ib wherein $R^1$ to $R^3$ are defined as in claim 1 and, wherein $R^4$ is hydrogen; or c) reduction of a compound according to formula Ib preferably with a reducing agent in a suitable solvent or solvent mixtures e.g. THF/TFA or NaCNBH$_3$ in acetic acid to obtain a compound of formula Ia

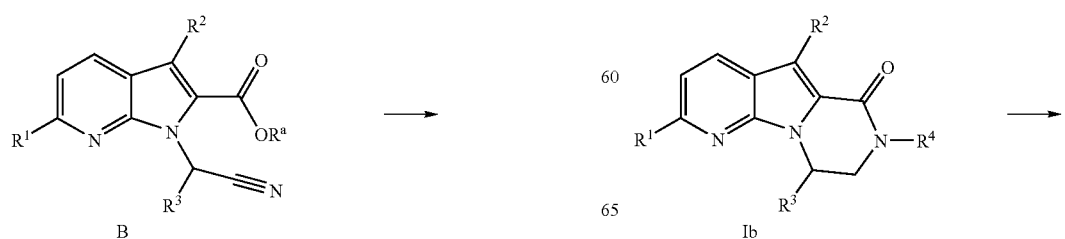

B

Ib

-continued

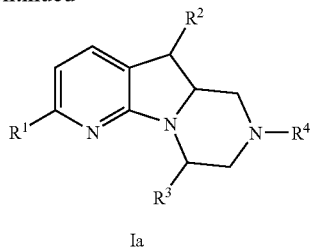

Ia wherein $R^1$ to $R^4$ are defined as in claim 1 and, wherein $R^4$ means preferably hydrogen; or d) reduction of a compound according to formula K, preferably with e.g. LiAlH$_4$, particularly in diethyl ether or THF

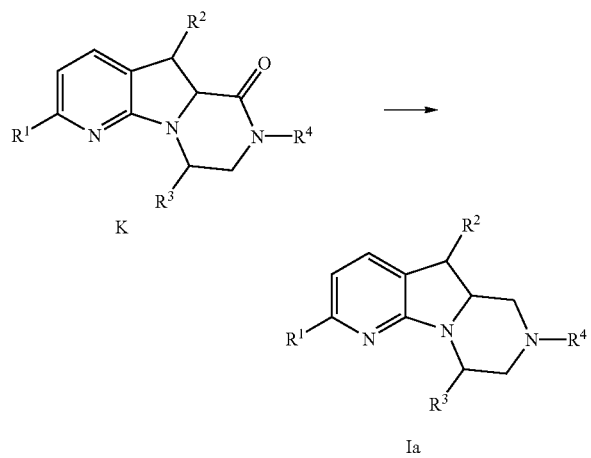

wherein $R^1$ to $R^4$ are defined above; or e) cleavage of the protective group (PG) of a compound according to formula Ic, preferably in the presence of acid such as trifluoroactetic acid or HCl in a suitable solvent such as ethyl acetate in order to obtain a compound of formula Id

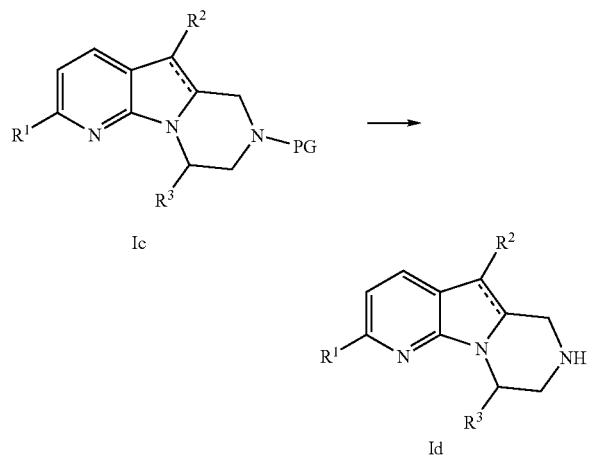

wherein $R^1$ to $R^3$ are defined as in claim 1. A preferred protecting group (PG) is the Boc group.

In another embodiment, the current invention includes the following novel intermediates:

(4R,10aR)-6-Bromo-4-methyl-3,4,9,9a-tetrahydro-1H-2,4a,5-triaza-fluorene-2-carboxylic acid tert-butyl ester;

7-Oxy-pyrrolo[2,3-b]pyridine-1,2-dicarboxylic acid 1-tert-butyl ester 2-ethyl ester;

6-Bromo-pyrrolo[2,3-b]pyridine-1,2-dicarboxylic acid 1-tert-butyl ester 2-ethyl ester;

6-Bromo-1H-pyrrolo[2,3-b]pyridine-2-carboxylic acid ethyl ester;

6-Hydroxy-1H-pyrrolo[2,3-b]pyridine-2-carboxylic acid ethyl ester; and

6-Hydroxy-pyrrolo[2,3-b]pyridine-1,2-dicarboxylic acid 1-tert-butyl ester 2-ethyl ester.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

1. Binding to Serotonin Receptors

The binding of compounds of formula (I) to serotonin receptors was determined in vitro by standard methods. The activity of the test compounds was investigated in accordance with the assays given below.

Method (a): For the binding to the $5\text{-HT}_{2C}$ receptor, the $5\text{-HT}_{2C}$ receptors were radiolabeled with [$^3$H]-5-HT. The affinity of the compounds for $5\text{-HT}_{2C}$ receptors in a CHO cell line was determined according to the procedure of D. Hoyer, G. Engel and H. O. Kalkman, *European J. Pharmacol.*, 1985, 118, 13–23.

Method (b): For the binding to the $5\text{-HT}_{2B}$ receptor, the $5\text{-HT}_{2B}$ receptors were radiolabeled with [$^3$H]-5-HT. The affinity of the compounds for human $5\text{-HT}_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the $5\text{-HT}_{2A}$ receptor, the $5\text{-HT}_{2A}$ receptors were radiolabeled with [$^{125}$I]-DOI. The affinity of the compounds for $5\text{-HT}_{2A}$ receptors in a CHO cell line was determined according to the procedure of D. J. McKenna and S. J. Peroutka, *J. Neurosci.*, 1989, 9, 3482–90.

The thus determined activity of the compound of the designated Example is shown in Table 1.

TABLE 1

| Compound | Method (a) $K_i$ (2C) | Method (b) $K_i$ (2B) | Method (c) $K_i$ (2A) |
|---|---|---|---|
| Example 7 | 8.1 nM | 136.9 nM | 229.0 nM |
| Example 9 | 16.5 nM | 270.8 nM | 212.1 nM |
| Example 20 | 5.1 nM | 108.0 nM | 177.8 nM |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

2. Functional Activity

The functional activity of compounds of formula (I) was assayed using a Fluorimetric Imaging Plate reader (FLIPR). CHO cells expressing the human $5\text{-HT}_{2C}$ or human $5\text{-HT}_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 μL of the assay buffer) was added at a rate of 70 μL/sec to each well of the FLIPR 96 well plate during fluorescence measurements. The measurements were taken at 1 sec intervals and the maximum fluorescent signal was measured (approx 10–15 secs after drug addition) and compared with the response produced by 10 μM 5-HT (defined as 100%) to which it was expressed as a percentage response (relative efficacy). Dose response curves were constructed using Graphpad Prism (Graph Software Inc.).

TABLE 2

| | h5-HT2C | | h5-HT2A | |
|---|---|---|---|---|
| Compound | $EC_{50}$ [nM] | Rel. Eff. [%] | $EC_{50}$ [nM] | Rel. Eff. [%] |
| Example 7 | 19.2 | 99.4 | 342.8 | 21.6 |
| Example 9 | 85.4 | 91.4 | 643.6 | 29.6 |
| Example 20 | 7.6 | 93.3 | 11.1 | 12.0 |

The compounds of formula (I) have activity at the h5-HT2c receptor in the range of 10,000 to 0.01 nM.

Preferred compounds of formula I as described above have activity at the h5-HT2c receptor below 10000 nM; especially preferred compounds below 1000 nM, particularly preferred compounds below 100 nM. Most preferred compounds have activity at the h5-HT2c receptor below 30 nM.

3. Regulation of Feeding Behavior

The in vivo activity of compounds of formula (1) was assessed for their ability to regulate feeding behavior by recording food consumption in food deprived animals. Rats were trained to have access to food for 2 h per day and were food deprived for 22 h. When they were trained under this schedule, the amount of food taken every day during these 2 h food intake session was consistent day after day.

To test the ability of the $5\text{-HT}_{2C}$ receptor agonists to decrease food intake, 8 animals were used in a cross-over study. Rats were individually housed in plexiglass boxes with a grid on the floor and a paper was placed below the cage floor to collect any spillage. A food dispenser (becher) filled with a preweighed amount of food was presented to them for 2 h. At the end of the food intake session, rats returned to their home cage. Each rat was weighed before the start of the experiment and the amount of food consumed during this 2 h food intake session was recorded. Either various doses of test compound or Vehicle was administered orally 60 min before the 2 h food intake session. A positive control Sibutramine was included in the experiment.

An Anova analysis with repeated measures was used followed by a posthoc test Student Neumann-Keuls. *P<0.05 compared to Saline-treated rats.

The minimum effective dose (m.e.d.) is defined as the lowest dose which produces a statistically significant reduction in food intake. The minimum effective doses for selected particularly preferred compounds of formula I are 30 mg/kg p.o. and below.

EXAMPLES

Example 1

(R)-6-Chloro-4-methyl-1,2,3,4-tetrahydro-2,4a,5-triaza-fluorene; hydrochloride

To a solution of 0.3 g (1.3 mmol) (R)-6-chloro-4-methyl-3,4-dihydro-2H-2,4a,5-triaza-fluoren-1-one in 20 ml tert-butyl methyl ether, 0.20 g (5.1 mmol) lithium aluminum hydride was added and the suspension was heated to reflux for 1 h and cooled to room temperature. The reaction mixture was poured into 20 ml saturated aqueous potassium sodium tartrate solution and filtered over dicalite speed plus. The filtrate was extracted four times with ethyl acetate. The combined organic phases were washed with brine, dried over magnesium sulfate and filtered. The crude product was purified by chromatography over silica gel (0.032–0.063 mm) with dichloromethane:methanol (49:1) as eluant. The colorless oil (81%) was dissolved in ethyl acetate and 0.6 ml of a 2M hydrochloric acid solution in ethyl acetate was added. The resulting suspension was stirred at 0 deg C. for 15 min and filtered; the filter-cake was washed with ethyl acetate and dried under high vacuum.

ISP-MS: m/e=222.2 ([M+H$^+$]) Elemental analysis: $C_{11}H_{13}Cl_2N_3$ (258.152) calc.[#]: C, 51.37; H, 5.31; N, 15.35; Cl, 25.90. found: C, 51.10; H, 5.13; N, 15.40; Cl, 25.81.

[#] Calculated with 1 mole $C_{11}H_{13}Cl_2N_3$ and 0.18 mole $C_4H_8O_2$.

Intermediates a) (R)-1-(2-tert-Butoxycarbonylamino-1-methyl-ethyl)-6-chloro-1H-pyrrolo[2,3-b]pyridine-2-carboxylic acid ethyl ester A solution of 3.0 g (13.3 mmol) 6-chloro-1H-pyrrolo[2,3-b]pyridine-2-carboxylic acid ethyl ester in 70 ml N,N-dimethylformamide was cooled to 0 deg C. and 1.58 g (14.0 mmol) potassium tert-butoxide was added. After 30 min, 3.49 g (14.7 mmol) (S)-5-methyl-2,2-dioxo-[1,2,3]oxathiazolidine-3-carboxylic acid tert-butyl ester was added in one portion. The cooling bath was removed and after 1.5 h the reaction mixture was poured into 100 ml 10% aqueous citric acid. The layers were separated and the aqueous phase was extracted three times with ethyl acetate. The combined organic phases were washed four times with water, once with brine and then were dried over magnesium sulfate. After filtration the solvent was removed on a rotary evaporator and the residue was purified by flash-chromatography over silica gel (0.032–0.063 mm) with n-hexane:ethyl acetate (9:1, then 5:1) as eluant to afford the product as a yellow oil (98.0%).

ISP-MS: m/e=382.3 ([M+H$^+$])

b) (R)-6-Chloro-4-methyl-3,4-dihydro-2H-2,4a,5-triaza-fluoren-1-one

A solution of 6.70 g (17.5 mmol) (R)-1-(2-tert-butoxy-carbonylamino-1-methyl-ethyl)-6-chloro-1H-pyrrolo[2,3-b]pyridine-2-carboxylic acid ethyl ester in 80 ml dichloromethane was cooled to 0 deg C. and 27 ml (0.35 mol) trifluoroacetic acid were added over 4 min. The cooling bath was removed and after 1 h the volatile components were removed on a rotary evaporator. The residue was dissolved in 40 ml methanol and 9.70 g (70.2 mmol) potassium carbonate was added. After stirring for 2.5 h the reaction mixture was diluted with water and ethyl acetate and the phases were separated. The aqueous phase was extracted three times with ethyl acetate. The combined organic layers were washed with brine, dried over magnesium sulfate and filtered. After evaporation, the residue was taken up in 50 ml tert-butyl methyl ether upon which the product started to precipitate. The solid was collected by filtration, washed with 20 ml of tert-butyl methyl ether and dried under high vacuum to afford the product as a pale yellow powder. The concentrated mother liquors were purified by flash chromatography over silica gel (0.032–0.063 mm) with ethyl acetate as eluant to yield another batch of product (86.6% total).

EI-MS: m/e=235.2 ([M+H$^+$])

Example 2

(4R,9aR)-6-Chloro-4-methyl-1,2,3,4,9,9a-hexahydro-2,4a,5-triaza-fluorene; hydrochloride A solution of 0.50 g (1.54 mmol) (4R,9aR)-6-chloro-4-methyl-3,4,9,9a-tetrahydro-1H-2,4a,5-triaza-fluorene-2-carboxylic acid tert-butyl ester in 5 ml dichloromethane was cooled to 0 deg C. and treated with 2.5 ml (3.72 g, 32.7 mmol) trifluoroacetic acid. The cooling bath was removed and after 1 h at room temperature the volatile components were removed on a rotary evaporator and the residue was purified by chromatography over silica gel (0.032–0.063 mm) with dichloromethane:methanol:ammonia (9:1:0.1) as eluant. The so-obtained free base was dissolved in 8 ml ethyl acetate and treated with 0.85 ml of a 2M hydrochloric acid solution in ethyl acetate. After 1 h the resulting suspension was filtered; the filter-cake was dried under high vacuum to afford the product as colorless crystals (55.5%).

EI-MS: m/e=224.2 ([M+H$^+$]) Elemental analysis: $C_{11}H_{14}ClN_3 \cdot HCl$ (266.731) calc.[#]: C, 49.67; H, 5.83; N, 15.31; Cl, 28.16. found: C, 49.87; H, 5.82; N, 15.27; Cl, 28.36.

[#] Calculated with 1 mole $C_{11}H_{14}ClN_3$ (HCl) 1.18 and 0.088 mole $C_4H_8O_2$ and 3.59% water.

Intermediates a) (R)-6-Chloro-4-methyl-3,4-dihydro-1H-2,4a,5-triaza-fluorene-2-carboxylic acid tert-butyl ester To a solution of 1.94 g (8.75 mol) (R)-6-chloro-4-methyl-1,2,3,4-tetrahydro-2,4a,5-triaza-fluorene in 20 ml dichloromethane was added successively 2.3 g (10.5 mol) di tert-butyl dicarbonate and 53.5 mg (0.44 mmol N,N-dimethylaminopyridine. After 3 h the solvent was removed on a rotary evaporator and the residue was purified by chromatography over silica gel (0.032–0.063 mm) with n-hexane:ethyl acetate (7:1) as eluant to afford the desired compound as a yellow oil (97.6%).

ISP-MS: m/e=322.3 ([M+H$^+$])

b) (4R,9aR)-6-Chloro-4-methyl-3,4,9,9a-tetrahydro-1H-2,4a,5-triaza-fluorene-2-carboxylic acid tert-butyl ester To a solution of 0.65 g (2.0 mmol) (R)-6-chloro-4-methyl-3,4-dihydro-1H-2,4a,5-triaza-fluorene-2-carboxylic acid tert-butyl ester in 10 ml acetic acid was added 0.64 g (10.1 mmol) sodium cyano borohydride. After 3 h the reaction mixture was poured into 10% aqueous sodium carbonate solution and extracted twice with ethyl acetate. The organic layers were washed with brine, dried over magnesium sulfate, filtered and evaporated. The residue was purified by chromatography over silica gel (0.032–0.063 mm) with n-hexane:ethyl acetate (4:1) as eluant to afford the desired compound as a colorless oil (65.7%).

ISP-MS: m/e=324.3 ([M+H$^+$])

Example 3 a) (4R,9aS)-6-Chloro-4-methyl-1,2,3,4,9,9a-hexahydro-2,4a,5-triaza-fluorene; hydrochloride To a solution of 1.0 g (4.27 mmol) (R)-6-chloro-4-methyl-3,4-dihydro-2H-2,4a,5-triaza-fluoren-1-one (Example 1, intermediate b) in 30 ml methanol was added 0.62 g (25.5 mmol) magnesium turnings. After a few minutes gas production began. Temperature was kept at ambient temperature with a cooling bath. After 2.5 h the reaction mixture was poured into a mixture of 60 ml 1N hydrochloric acid, ice and 90 ml buffer pH 7 and was extracted twice with ethyl acetate. The organic phases were washed with brine, dried over magnesium sulfate and filtered. After evaporation of the solvent the remaining light brown oil (350 mg) was dissolved in 20 ml tert-butyl methyl ether, 0.25 g (6.60 mmol). To the solution was added lithium aluminium hydride and the reaction mixture was heated to reflux for 1 h. The oil bath was removed and the mixture was cooled to room temperature. The suspension was poured into 7 ml saturated aqueous potassium sodium tartrate solution and filtered over dicalite speed plus. The filtrate was extracted twice with ethyl acetate. The combined organic phases were washed with brine, dried over magnesium sulfate and filtered. The crude product was purified by column chromatography over silica gel (0.032–0.063 mm) with dichloromethane:methanol (49:1) as eluant. The colorless oil (28 mg) was dissolved in 2 ml ethyl acetate and 0.1 ml of a 2M hydrochloric acid solution in ethyl acetate was added. The resulting suspension was stirred at 0 deg C. for 45 min and filtered. The filter-cake was washed with ethyl acetate and dried under high vacuum to afford the desired compound as a colorless powder (2.1%).

ISP-MS: m/e=224.1 ([M+H$^+$])

Example 4

(R)-6-Bromo-4-methyl-1,2,3,4-tetrahydro-2,4a,5-triaza-fluorene; hydrochloride

This compound was prepared in analogy to Example 1 from (R)-6-bromo-4-methyl-3,4-dihydro-2H-2,4a,5-triaza-fluoren-1-one.

Light yellow crystals (45.4%).

ISP-MS: m/e=266.2 ([M+H$^+$])

Intermediates a) Pyrrolo[2,3-b]pyridine-1,2-dicarboxylic acid 1-tert-butyl ester 2-ethyl ester To a solution of 80.9 g (0.43 mol) 1H-pyrrolo[2,3-b]pyridine-2-carboxylic acid ethyl ester in 1800 ml acetonitrile was added 111.4 g (0.51 mol) di-tert-butyl dicarbonate followed by 2.60 g (0.02 mol) 4-dimethylaminopyridine. After 1 h the solvent was removed on a rotary evaporator and the residue was purified by flash column chromatography over silica gel (0.032–0.063 mm) with n-hexane:ethyl acetate (9:1) as eluant to afford the product as a yellow oil (96.6%).

ISP-MS: m/e=291.2 ([M+H$^+$])

b) 7-Oxy-pyrrolo[2,3-b]pyridine-1,2-dicarboxylic acid 1-tert-butyl ester 2-ethyl ester To a solution of 88.7 g (0.31 mol) pyrrolo[2,3-b]pyridine-1,2-dicarboxylic acid 1-tert-butyl ester 2-ethyl ester in 1600 ml dichloromethane was added 150.5 g (0.61 mol) 3-chloroperoxybenzoic acid. After 7 h another 150.5 g (0.61 mol) 3-chloroperoxybenzoic acid was added. After 24 h the reaction mixture was poured into 960 ml saturated aqueous potassium carbonate solution. Water and dichloromethane (1750 ml, 1:1) were added, after 5 min the aqueous phase was separated and extracted three times each with 900 ml dichloromethane. The combined organic phases were washed with 1000 ml water and 1000 ml brine, dried over magnesium sulfate and filtered. The solvent was removed on a rotary evaporator until a white suspension had formed. A 150 ml portion of tert-butyl methyl ether was added and the suspension was filtered. The filter-cake was washed with 70 ml tert-butyl methyl ether and dried under high vacuum to afford the desired product as a white solid (59.5%).

EI-MS: m/e306.2 ([M])

c) 6-Bromo-pyrrolo[2,3-b]pyridine-1,2-dicarboxylic acid 1-tert-butyl ester 2-ethyl ester To a suspension of 30.0 g (0.098 mol) 7-oxy-pyrrolo[2,3-b]pyridine-1,2-dicarboxylic acid 1-tert-butyl ester 2-ethyl ester in toluene were added simultaneously solutions of 20.5 ml (15.8 g, 0.098 mol) hexamethyldisilazane in 420 ml toluene and 29.4 ml (45.3 g, 0.24 mol) benzoyl bromide in 420 ml toluene over 1 h. After an additional hour the reaction mixture was poured into 400 ml 10% aqueous sodium carbonate solution and the phases were separated. The aqueous phase was extracted twice with 500 ml ethyl acetate and the combined organic layers washed twice with 600 ml saturated sodium carbonate solution and brine. After filtration and removal of the solvent the residue was purified by chromatography over silica gel (0.032–0.063 mm) with n-hexane:ethyl acetate (24:1 then 19:1) as eluant to afford the product as a colorless solid (50.9%).

ISP-MS: m/e=371.1 ([M+H$^+$])

d) 6-Bromo-1H-pyrrolo[2,3-b]pyridine-2-carboxylic acid ethyl ester

The solution of 18.4 g (0.05 mol) 6-bromo-pyrrolo[2,3-b]pyridine-1,2-dicarboxylic acid 1-tert-butyl ester 2-ethyl ester in 165 ml dichloromethane was cooled to 0 deg C. and then 38.0 ml trifluoroacetic acid was added within 5 min. The cooling bath was removed and after 2 h at room temperature the reaction mixture was poured into 500 ml saturated aqueous sodium bicarbonate solution. The organic layer was extracted three times with 150 ml dichloromethane. The combined organic phases were washed with 200 ml brine, dried over magnesium sulfate and filtered. The solvent was evaporated and the residue was dried under high vacuum to afford 12.0 g (95.5%) of the desired product as a colorless solid.

ISP-MS: m/e=269.2 ([M+H⁺])

e) (R)-6-Bromo-1-(2-tert-butoxycarbonylamino-1-methyl-ethyl)-1H-pyrrolo[2,3-b]pyridine-2-carboxylic acid ethyl ester This compound was prepared in analogy to Example 1, intermediate a) from 6-bromo-1H-pyrrolo[2,3-b]pyridine-2-carboxylic acid ethyl ester, potassium tert-butoxide and (S)-5-methyl-2,2-dioxo-[1,2,3]oxathiazolidine-3-carboxylic acid tert-butyl ester.

Yellow gum (93.2%).

ISP-MS: m/e=426.3 ([M+H⁺])

f) (R)-6-Bromo-4-methyl-3,4-dihydro-2H-2,4a,5-triaza-fluoren-1-one

This compound was prepared in analogy to Example 1, intermediate b) from (R)-6-bromo-1-(2-tert-butoxycarbony-lamino-1-methyl-ethyl)-1H-pyrrolo[2,3-b]pyridine-2-carboxylic acid ethyl ester.

Colorless solid (73.6%).

ISP-MS: m/e=282.0 ([M+H⁺])

Example 5

(4R,9aR)-6-Bromo-4-methyl-1,2,3,4,9,9a-hexahydro-2,4a,5-triaza-fluorene; hydrochloride This compound was prepared in analogy to Example 2 from (4R,9aR)-6-bromo-4-methyl-3,4,9,9a-tetrahydro-1H-2,4a,5-triaza-fluorene-2-carboxylic acid tert-butyl ester.

Light brown solid (37.1%).

ISP-MS: 268.2 ([M+H⁺]) Elemental analysis: $C_{11}H_{15}BrClN_3$ (304.619) calc.: C, 43.37; H, 4.96; N, 13.79; Cl, 11.64; Br, 26.23. found#): C, 43.28; H, 4.98; N, 13.45; Cl, 11.67; Br, 26.00.

) Calculated with 0.51% water

Intermediates a) (R)-6-Bromo-4-methyl-3,4-dihydro-1H-2,4a,5-triaza-fluorene-2-carboxylic acid tert-butyl ester This compound was prepared in analogy to Example 2, intermediate a) from (R)-6-bromo-4-methyl-1,2,3,4-tetrahydro-2,4a,5-triaza-fluorene, 4-(dimethylamino)pyridine and di tert-butyl dicarbonate.

Light yellow foam (97.3%).

ISP-MS: m/e=366.1 ([M+H⁺])

b) (4R,9aR)-6-Bromo-4-methyl-3,4,9,9a-tetrahydro-1H-2,4a,5-triaza-fluorene-2-carboxylic acid tert-butyl ester This compound was prepared in analogy to Example 2, intermediate b) from (R)-6-bromo-4-methyl-3,4-dihydro-1H-2,4a,5-triaza-fluorene-2-carboxylic acid tert-butyl ester and sodium cyano borohydride.

Colorless solid (82.5%).

ISP-MS: m/e370.3 ([M+H⁺])

Example 6

(4R,9aS)-6-Bromo-4-methyl-1,2,3,4,9,9a-hexahydro-2,4a,5-triaza-fluorene; hydrochloride This compound was prepared in analogy to Example 2 from (4R,9aS)-6-bromo-4-methyl-3,4,9,9a-tetrahydro-1H-2,4a,5-triaza-fluorene-2-carboxylic acid tert-butyl ester.

Colorless solid (77.8%).

ISP-MS: m/e=270.2 ([M+H⁺]) Elemental analysis: $C_{11}H_{15}BrClN_3$ (304.619) calc.#): C, 43.55; H, 5.01; N, 13.73; Cl, 11.59; Br, 26.12. found: C, 43.37; H, 4.85; N, 13.57; Cl, 11.57; Br, 25.87.

) Calculated with 1 mole $C_{11}H_{15}BrClN_3$ and 0.0154 mole $C_6H_{14}$ and 0.07% water Intermediate (4R,9aS)-6-Bromo-4-methyl-3,4,9,9a-tetrahydro-1H-2,4a,5-triaza-fluorene-2-carboxylic acid tert-butyl ester This compound was prepared in analogy to Example 2, intermediate b) from (R)-6-bromo-4-methyl-3,4-dihydro-1H-2,4a,5-triaza-fluorene-2-carboxylic acid tert-butyl ester and sodium cyano borohydride.

Colorless solid (6.2%).

ISP-MS: m/e=370.3 ([M+H⁺])

Example 7

(R)-4,6-Dimethyl-1,2,3,4-tetrahydro-2,4a,5-triaza-fluorene; hydrochloride

This compound was prepared in analogy to Example 2 from (R)-4,6-dimethyl-3,4-dihydro-1H-2,4a,5-triaza-fluorene-2-carboxylic acid tert-butyl ester.

Light yellow solid (57.0%).

ISP-MS: m/e=204.2 ([M+H⁺])

Intermediate (R)-4,6-Dimethyl-3,4-dihydro-1H-2,4a,5-triaza-fluorene-2-carboxylic acid tert-butyl ester To a solution of 0.20 g (0.55 mmol) (R)-6-bromo-4-methyl-3,4-dihydro-1H-2,4a,5-triaza-fluorene-2-carboxylic acid tert-butyl ester (Example 5, intermediate a) in 10 ml 1,2-dimethoxyethane was added 63 mg (55 µmol) tetrakis (triphenylphosphine)palladium. After 30 min, 5 ml saturated aqueous sodium carbonate solution and 0.09 ml (0.65 mmol) of a 1M trimethylboroxine solution in THF were added and the resulting suspension was heated to reflux for 5 h. The reaction mixture was cooled to room temperature, poured into 20 ml 1M aqueous sodium hydroxide solution and extracted three times with ethyl acetate. The combined organic layers were washed with brine, dried over magnesium sulfate, filtered and evaporated. The residue was purified by flash column chromatography on silica gel (0.032–0.063 mm) with ethyl acetate:n-hexane (1:1) as eluant to yield the desired product as a yellow solid (71.1%).

ISP-MS: m/e=302.3 ([M+H⁺])

Example 8

(4R,9aR)-4,6-Dimethyl-1,2,3,4,9,9a-hexahydro-2,4a,5-triaza-fluorene; hydrochloride This compound was prepared in analogy to Example 2 from (4R,9aR)-4,6-dimethyl-3,4,9,9a-tetrahydro-1H-2,4a,5-triaza-fluorene-2-carboxylic acid tert-butyl ester.

Light yellow solid (75.9%).

ISP-MS: m/e=204.2 ([M+H⁺])

Intermediate (4R,9aR)-4,6-Dimethyl-3,4,9,9a-tetrahydro-1H-2,4a, 5-triaza-fluorene-2-carboxylic acid tert-butyl ester To a solution of 19.5 g (0.053 mol) (4R,9aR)-6-bromo-4-methyl-3,4,9,9a-tetrahydro-1H-2,4a,5-triaza-fluorene-2-carboxylic acid tert-butyl ester (Example 5, intermediate b) in 800 ml 1,2-dimethoxyethane was added 12.2 g (0.01 mol) tetrakis(triphenylphosphine)palladium(0) and the suspension was stirred for 30 min at room temperature. Water (400 ml), 16.8 g (0.16 mol) sodium carbonate and 13.3 g (0.10 mol) trimethylboroxine were added and the reaction mixture was heated to reflux and stirred for 3 h under reflux. The suspension was poured into 10% aqueous sodium bicarbonate solution and ethyl acetate and the phases were separated. The organic layer was washed with brine, dried over magnesium sulfate, filtered and evaporated. The residue was purified by chromatography on silica gel (0.032–0.063 mm) with n-hexane:ethyl acetate (4:1) as eluant to afford the compound as a light yellow oil (52.6%).

ISP-MS: m/e304.3 ([M+H$^+$])

Example 9

(4R,9aR)-6-Ethyl-4-methyl-1,2,3,4,9,9a-hexahydro-2,4a,5-triaza-fluorene; hydrochloride This compound was prepared in analogy to Example 2 from (4R,9aR)-6-ethyl-4-methyl-3,4,9,9a-tetrahydro-1H-2,4a,5-triaza-fluorene-2-carboxylic acid tert-butyl ester.

Off-white solid (94.5%).
ISP-MS: m/e=218.3 ([M+H$^+$])

Intermediate (4R,9aR)-6-Ethyl-4-methyl-3,4,9,9a-tetrahydro-1H-2,4a,5-triaza-fluorene-2-carboxylic acid tert-butyl ester To a solution of 0.70 g (1.90 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 14 ml N,N-dimethylformamide was added 73.0 mg [1,1'-bis(diphenyphosphino)ferrocene]-dichloropalladium(II) and after 15 min, 4.8 ml of a 1M triethylborane solution in THF and 0.79 g (5.70 mmol) potassium carbonate were added. After 4 h another 2.4 ml triethylborane solution was added and the reaction mixture stirred overnight at 65 deg C. The mixture was cooled to room temperature and the suspension was poured into water and extracted twice with ethyl acetate. The combined organic phases were washed with brine, dried over magnesium sulfate, filtered and evaporated. The crude product was purified by column chromatography on silica gel (Q0.032–0.063 mm) with tert-butyl methyl ether:n-hexane (1:4) as eluant to yield the product as a colorless oil (89.5%).

ISP-MS: m/e=318.4 ([M+H$^+$])

Example 10

(4R,9aR)-4-Methyl-6-trifluoromethyl-1,2,3,4,9,9a-hexahydro-2,4a,5-triaza-fluorene; hydrochloride This compound was prepared in analogy to Example 2 from (4R,9aR)-4-methyl-6-trifluoromethyl-3,4,9,9a-tetrahydro-1H-2,4a,5-triaza-fluorene-2-carboxylic acid tert-butyl ester.

Light brown solid (73.0%).
ISP-MS: m/e=258.2 ([M+H$^+$])

Intermediate (4R,9aR)-4-Methyl-6-trifluoromethyl-3,4,9,9a-tetrahydro-1H-2,4a,5-triaza-fluorene-2-carboxylic acid tert-butyl ester To a solution of 0.8 g (2.17 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 12 ml 1-methyl-2-pyrrolidone, 2.36 g (17.4 mmol) sodium trifluoroacetate was added. After a solution had formed, 1.65 g (8.7 mmol) copper iodide was added and the reaction mixture was heated to 180 deg C. for 2 h. The mixture was cooled to room temperature, ethyl acetate and water were added and the suspension was filtered through a bed of dicalite speed plus. The phases were separated, the aqueous layer was washed with ethyl acetate and the combined organic phases were washed with brine, dried over magnesium sulfate, filtered and evaporated. The residue was purified by chromatography over silica gel (0.032–0.063 mm) with tert-butyl methyl ether:n-hexane (1:5) as eluant to afford the desired compound as a colorless oil (27.7%).

ISP-MS: m/e=358.3 ([M+H$^+$])

Example 11

(4R,9aR)-6-Cyclopropyl-4-methyl-1,2,3,4,9,9a-hexahydro-2,4a,5-triaza-fluorene; hydrochloride This compound was prepared in analogy to Example 2 from (4R,9aR)-6-cyclopropyl-4-methyl-3,4,9,9a-tetrahydro-1H-2,4a,5-triaza-fluorene-2-carboxylic acid tert-butyl ester.

Light brown solid (62.0%).
ISP-MS: m/e=230.3 ([M+H$^+$])

Intermediate (4R,9aR)-6-Cyclopropyl-4-methyl-3,4,9,9a-tetrahydro-1H-2,4a,5-triaza-fluorene-2-carboxylic acid tert-butyl ester A suspension of 150.0 mg (1.23 mmol) 9-borabicyclo[3.3.1]nonane and 47 µl (0.62 mmol) propargyl bromide in 1 ml tetrahydrofuran was heated to reflux for 2 h. The mixture was cooled to room temperature then 0.61 ml (1.83 mmol) of a degassed 3M sodium hydroxide solution was added and after 1 h a mixture of 0.20 g (0.54 mmol) (4R,9aR)-6-bromo-4-methyl-3,4,9,9a-tetrahydro-1H-2,4a, 5-triaza-fluorene-2-carboxylic acid tert-butyl ester (Example 5, intermediate b) and 19.0 mg tetrakis(triphenylphosphine)palladium in 1 ml tetrahydrofuran was added. The mixture was heated to reflux for 16 h then cooled to room temperature and poured into water and ethyl acetate; the phases were separated. The aqueous phase was extracted three times with ethyl acetate and the combined organic layers were washed with 1M aqueous sodium hydroxide solution and brine, dried over magnesium sulfate, filtered and evaporated. The residue was purified by chromatography on silica gel (0.032–0.063 mm) with n-hexane as eluant to afford the desired product as a colorless oil (35.2%).

ISP-MS: m/e=330.4 ([M+H$^+$])

Example 12

(4R,9aR)-3-(4-Methyl-1,2,3,4,9,9a-hexahydro-2,4a, 5-triaza-fluoren-6-yl)-acrylic acid ethyl ester; hydrochloride This compound was prepared in analogy to Example 2 from (4R 9aR)-6-(2-ethoxycarbonyl-vinyl)-4-methyl-3,4,9, 9a-tetrahydro-1H-2,4a,5-triaza-fluorene-2-carboxylic acid tert-butyl ester.
Yellow solid (66.5%).
ISP-MS: m/e288.3 ([M+H$^+$])

Intermediate (4R,9aR)-6-(2-Ethoxycarbonyl-vinyl)-4-methyl-3,4, 9,9a-tetrahydro-1H-2,4a,5-triaza-fluorene-2-carboxylic acid tert-butyl ester To a solution of 1.0 g (2.71 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) and 0.36 ml (3.25 mmol) ethyl acrylate in 30 ml toluene were added 0.67 g (8.15 mmol) sodium acetate, 82.6 mg (0.27 mmol) tri(o-tolyl)phosphine and 0.04 mg (0.1 mmol) allylpalladium chloride dimer. The reaction mixture was heated under reflux for 20 h, then poured into saturated aqueous sodium bicarbonate solution and extracted with ethyl acetate. The organic phase was washed with 10% aqueous citric acid solution and brine, dried over magnesium sulfate, filtered and evaporated. The crude product was purified by column chromatography on silica gel (0.032–0.063 mm) with n-hexane:ethyl acetate (9:1) as eluant to afford the desired compound as a yellow solid (91.2%).
ISP-MS: m/e=388.3 ([M+H$^+$])

Example 13

(4R,9aR)-6-(3-Methoxy-propyl)-4-methyl-1,2,3,4,9, 9a-hexahydro-2,4a,5-triaza-fluorene This compound was prepared in analogy to Example 2 from (4R,9aR)-6-(3-methoxy-propyl)-4-methyl-3,4,9,9a-tetrahydro-1H-2,4a,5-triaza-fluorene-2-carboxylic acid tert-butyl ester.
Light brown oil (90.5%).
ISP-MS: m/e=262.3 ([M+H$^+$])

Intermediate a) (4R,9aR)-6-(3-Hydroxy-propyl)-4-methyl-3,4,9,9a-tetrahydro-1H-2,4a,5-triaza-fluorene-2-carboxylic acid tert-butyl ester
To a solution of 245.0 mg (0.63 mmol) (4R,9aR)-6-(2-ethoxycarbonyl-vinyl)-4-methyl-3,4,9,9a-tetrahydro-1H-2, 4a,5-triaza-fluorene-2-carboxylic acid tert-butyl ester (Example 12, intermediate) in 10 ml diethyl ether were added 50.0 mg (1.32 mmol) lithium aluminium hydride. After 2 h the reaction mixture was poured into saturated aqueous potassium sodium tartrate solution and ethyl acetate then filtered through a short pad of dicalite speed plus. The aqueous phase was extracted four times with ethyl acetate and the combined organic layers were washed with brine, dried over magnesium sulfate, filtered and evaporated. The residue was purified by chromatography on silica gel (0.032–0.063 mm) with ethyl acetate:n-hexane as eluant to afford the compound as a colorless solid (50.5%).
ISP-MS: m/e=348.6 ([M+H$^+$])

b) (4R,9aR)-6-(3-Methoxy-propyl)-4-methyl-3,4,9,9a-tetrahydro-1H-2,4a,5-triaza-fluorene-2-carboxylic acid tert-butyl ester
A solution of 160.0 mg (0.46 mmol) (4R,9aR)-6-(3-hydroxy-propyl)-4-methyl-3,4,9,9a-tetrahydro-1H-2,4a,5-triaza-fluorene-2-carboxylic acid tert-butyl ester in 4 ml tetrahydrofuran was cooled to 0 deg C. and treated with 24.0 mg (0.51 mmol, 60% dispersion in mineral oil) sodium hydride. After 30 min 32 μl (0.51 mmol) methyl iodide was added and the cooling bath was removed. After 6 h another 0.64 μl (1.02 mmol) methyl iodide was added and the reaction was stirred overnight. The reaction mixture was poured into water and was extracted three times with ethyl acetate. The combined organic layers were washed with brine, dried over magnesium sulfate, filtered and concentrated on a rotary evaporator. The residue was purified by chromatography on silica gel (0.032–0.063 mm) with ethyl acetate:n-hexane (1:4) as eluant to afford the desired compound as a colorless oil (73.9%).
ISP-MS: m/e362.4 ([M+H$^+$])

Example 14

(4R,9aR)-4-Methyl-1,2,3,4,9,9a-hexahydro-2,4a,5-triaza-fluorene-6-carbonitrile; hydrochloride This compound was prepared in analogy to Example 2 from (4R,9aR)-6-cyano-4-methyl-3,4,9,9a-tetrahydro-1H-2, 4a,5-triaza-fluorene-2-carboxylic acid tert-butyl ester.
Light yellow solid (62.3%).
ISP-MS: m/e=215.4 ([M+H$^+$])

Intermediate (4R,9aR)-6-Cyano-4-methyl-3,4,9,9a-tetrahydro-1H-2,4a,5-triaza-fluorene-2-carboxylic acid tert-butyl ester To a solution of 0.20 g (0.54 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 5 ml dioxane were added 195.0 mg (2.17 mmol) copper (I)cyanide, 22.5 mg (22 μmol) tris(dibenzylideneacetone) dipalladium(0), 48.2 mg (87 μmol) 1,1'-bis(diphenylphosphino)ferrocene and 0.13 g (0.81 mmol) tetraethylammonium cyanide and the suspension was heated to reflux and stirred for 1.5 h. The mixture was cooled to room temperature, filtered and the filtrate was washed successively with aqueous saturated sodium bicarbonate solution, aqueous 10% citric acid solution, brine, dried over magnesium sulfate, filtered and evaporated. The residue was immediately purified by flash column chromatography on silica gel (0.032–0.063 mm) to afford the desired compound as a colorless foam (98.4%).
ISP-MS: m/e=315.3 ([M+H$^+$])

Example 15

(4R,9aR)-6-Cyclopropylmethoxymethyl-4-methyl-1,2,3,4,9,9a-hexahydro-2,4a,5-triaza-fluorene; hydrochloride This compound was prepared in analogy to Example 2 from (4R,9aR)-6-cyclopropylmethoxymethyl-4-methyl-3,4,9,9a-tetrahydro-1H-2,4a,5-triaza-fluorene-2-carboxylic acid tert-butyl ester.

Light yellow crystals (89.6%).
ISP-MS: m/e=274.4 ([M+H$^+$])

Intermediates a) (4R,9aR)-4-Methyl-3,4,9,9a-tetrahydro-1H-2,4a,5-triaza-fluorene-2,6-dicarboxylic acid 2-tert-butyl ester 6-methyl ester To a solution of 6.0 g (16.3 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 60 ml methanol were added 0.57 g (0.8 mmol) and 3.4 ml (2.5 g, 24.4 mmol) triethylamine and the reaction mixture was stirred at 80 deg C. for 24 h under a carbon monoxide atmosphere of 40 bar. The suspension was cooled to room temperature, poured into a mixture of water, ethyl acetate and brine and was extracted with further portions of ethyl acetate. The combined organic layers were separated, dried over magnesium sulfate and filtered. The residue was purified by chromatography on silica gel (0.032–0.063 mm) to afford the product as a light yellow foam (74.4%).
ISP-MS: m/e=348.5 ([M+H$^+$])

b) (4R,9aR)-6-Hydroxymethyl-4-methyl-3,4,9,9a-tetrahydro-1H-2,4a,5-triaza-fluorene-2-carboxylic acid tert-butyl ester A solution of 4.2 g (12.1 mmol) (4R,9aR)-4-methyl-3,4,9,9a-tetrahydro-1H-2,4a,5-triaza-fluorene-2,6-dicarboxylic acid 2-tert-butyl ester 6-methyl ester in 100 ml tetrahydrofuran was cooled to 0 deg C. and treated dropwise with 48.4 ml diisobutylaluminium hydride (48.4 mmol; 1M solution in THF). The cooling bath was removed and after 1 h at room temperature the reaction was quenched with a 10% aqueous potassium sodium tartrate solution and ethyl acetate was added. The two-phase system was filtered through a bed of dicalite speed plus; the filtrate was extracted with ethyl acetate and the organic phase was dried over magnesium sulfate. After filtration and evaporation the residue was purified by chromatography on silica gel (0.032–0.062 mm) with ethyl acetate as eluant to afford the desired product as a light yellow foam (67.3%).
ISP-MS: m/e=320.4 ([M+H$^+$])

c) (4R,9aR)-6-Cyclopropylmethoxymethyl-4-methyl-3,4,9,9a-tetrahydro-1H-2,4a,5-triaza-fluorene-2-carboxylic acid tert-butyl ester To a solution of 1.2 g (37.6 mmol) (4R,9aR)-6-hydroxymethyl-4-methyl-3,4,9,9a-tetrahydro-1H-2,4a,5-triaza-fluorene-2-carboxylic acid tert-butyl ester in 30 ml N,N-dimethylformamide was added 0.18 g (41.4 mmol) sodium hydride. After 30 min 0.72 ml (1.01 g, 75.2 mmol) (bromomethyl)cyclopropane was added and the reaction was stirred for 3 h. The reaction mixture was poured into 10% aqueous sodium bicarbonate solution and ethyl acetate. The organic layer was washed with brine, dried over magnesium sulfate, filtered and evaporated. The residue was purified by chromatography on silica gel (0.032–0.063 mm) with a gradient of ethyl acetate:n-hexane (1:1 to 100:0) as eluant to afford the compound as a light yellow oil (67.1%).
ISP-MS: m/e=374.5 ([M+H$^+$])

Example 16

(4R,9aR)-6-(2-Methoxy-ethoxymethyl)-4-methyl-1,2,3,4,9,9a-hexahydro-2,4a,5-triaza-fluorene This compound was prepared in analogy to Example 2 from (4R,9aR)-6-(2-methoxy-ethoxymethyl)-4-methyl-3,4,9,9a-tetrahydro-1H-2,4a,5-triaza-fluorene-2-carboxylic acid tert-butyl ester.
EI-MS: m/e=278.3 ([M+H$^+$])

Intermediate (4R,9aR)-6-(2-Methoxy-ethoxymethyl)-4-methyl-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester, sodium hydride and 2-bromoethyl methyl ether.
Colorless oil (33.8%).
ISP-MS: m/e=378.5 ([M+H$^+$])

Example 17

(4R,9aR)-6-Methoxymethyl-4-methyl-1,2,3,4,9,9a-hexahydro-2,4a,5-triaza-fluorene

This compound was prepared in analogy to Example 2 from (4R,9aR)-6-methoxymethyl-4-methyl-3,4,9,9a-tetrahydro-1H-2,4a,5-triaza-fluorene-2-carboxylic acid tert-butyl ester.
Light yellow oil (95.3%).
ISP-MS: m/e234.4 ([M+H$^+$])

Intermediate (4R,9aR)-6-Methoxymethyl-4-methyl-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester and methyl iodide.
Light yellow oil (75.8%).
ISP-MS: m/e334.4 ([M+H$^+$])

Example 18

(R)-4-Methyl-1,2,3,4,9,9a-hexahydro-2,4a,5-triaza-fluorene; hydrochloride 1:1.45

This compound was prepared in analogy to Example 2 from (R)-4-methyl-3,4,9,9a-tetrahydro-1H-2,4a,5-triaza-fluorene-2-carboxylic acid tert-butyl ester.
Colorless solid (51.7%).
EI-MS: m/e=189.2 ([M]) Elemental analysis: $C_{11}H_{14}ClN_{13}$·1.45HCl (242.130) calc.: C, 54.57; H, 6.85; N, 17.36; Cl, 21.23. found*: C, 54.63 H, 6.61; N, 17.41; Cl, 21.38.

) Calculated with 0.48% water

Intermediates a) (R)-1-(2-tert-Butoxycarbonylamino-1-methyl-ethyl)-1H-pyrrolo[2,3-b]pyridine-2-carboxylic acid ethyl ester This compound was prepared in analogy to Example 1 intermediate a), from 1H-pyrrolo[2,3-b]pyridine-2-carboxylic acid ethyl ester, potassium tert-butoxide and (S)-5-methyl-2,2-dioxo-[1,2,3]oxathiazolidine-3-carboxylic acid tert-butyl ester.

Yellow oil (100%).
ISP-MS: m/e=348.4 ([M+H$^+$])

b) (R)-4-Methyl-3,4-dihydro-2H-2,4a,5-triaza-fluoren-1-one

This compound was prepared in analogy to Example 1 intermediate b), from (R)-1-(2-tert-butoxycarbonylamino-1-methyl-ethyl)-1H-pyrrolo [2,3-b]pyridine-2-carboxylic acid ethyl ester.

Colorless solid (70.2%).
EI-MS: m/e=201.1 ([M])

c) (R)-4-Methyl-1,2,3,4-tetrahydro-2,4a,5-triaza-fluorene

This compound was prepared in analogy to Example 1 from (R)-4-methyl-3,4-dihydro-2H-2,4a,5-triaza-fluoren-1-one.

Pale yellow oil (79%).
ISP-MS: m/e=188.3 ([M+H$^+$])

d) (R)-4-Methyl-3,4-dihydro-1H-2,4a,5-triaza-fluorene-2-carboxylic acid tert-butyl ester This compound was prepared in analogy to Example 2 intermediate a), from (R)-4-methyl-1,2,3,4-tetrahydro-2,4a, 5-triaza-fluorene, 4-(dimethylamino)pyridine and di tert-butyl dicarbonate.

Yellow oil (96.1%).
EI-MS: m/e=287.3 ([M])

e) (R)-4-Methyl-3,4,9,9a-tetrahydro-1H-2,4a,5-triaza-fluorene-2-carboxylic acid tert-butyl ester This compound was prepared in analogy to Example 2 intermediate b), from (R)-4-methyl-3,4-dihydro-1H-2,4a,5-triaza-fluorene-2-carboxylic acid tert-butyl ester and sodium cyano borohydride.

Light brown oil (83.4%).
ISP-MS: m/e=290.3 ([M+H$^+$])

Example 19

(4R,9aR)-4-Methyl-1,2,3,4,9,9a-hexahydro-2,4a,5-triaza-fluoren-6-ylamine

This compound was prepared in analogy to Example 2 from (4R,9aR)-6-amino-4-methyl-3,4,9,9a-tetrahydro-1H-2,4a,5-triaza-fluorene-2-carboxylic acid tert-butyl ester.
White foam (78.2%).
EI-MS: m/e=205.2 ([M+H$^+$])

Intermediates a) (4R,9aR)-6-(Benzhydrylidene-amino)-4-methyl-3,4,9,9a-tetrahydro-1H-2,4a,5-triaza-fluorene-2-carboxylic acid tert-butyl ester A mixture consisting of 0.20 g (0.54 mmol) (4R,9aR)-6-bromo-4-methyl-3,4,9,9a-tetrahydro-1H-2,4a,5-triaza-fluorene-2-carboxylic acid tert-butyl ester, 91 μl (0.54 mmol) benzophenone imine, 73.0 mg (0.76 mmol) sodium tert-butoxide, 5.6 mg (0.01 mmol) tris(dibenzylideneacetone) dipalladium chloroform complex and 10.1 mg (0.02 mmol) R-(+)-2,2'-bis(diphenylphosphino)-1,1'-binaphthalene in 3 ml toluene was stirred at reflux for 1 h. The reaction mixture was cooled to room temperature, poured into 10% aqueous sodium bicarbonate solution and extracted twice with ethyl acetate. The combined organic layers were washed with brine, dried over magnesium sulfate, filtered and evaporated. The residue was purified by chromatography on silica gel (0.032–0.063 mm) with n-hexane:ethyl acetate (2:1) as eluant to afford the product as a yellow foam (94.3%).
ISP-MS: m/e=469.3 ([M+H$^+$])

b) (4R,9aR)-6-Amino-4-methyl-3,4,9,9a-tetrahydro-1H-2, 4a,5-triaza-fluorene-2-carboxylic acid tert-butyl ester To a solution of 0.23 g (0.49 mmol) (4R,9aR)-6-(benzhydrylidene-amino)-4-methyl-3,4,9,9a-tetrahydro-1H-2,4a,5-triaza-fluorene-2-carboxylic acid tert-butyl ester in 2.5 ml methanol were added 0.46 g (7.4 mmol) ammonium formate and 104 mg (0.05 mmol) 5% palladium on charcoal and the suspension was stirred for 1 h at 60 deg C. The cooled reaction mixture was filtered through a short bed of dicalite speed plus, extracted with 10% aqueous sodium bicarbonate, brine, dried over magnesium sulfate, filtered and evaporated. The residue was purified by chromatography on silica gel (0.032–0.063 mm) to yield the product as a colorless oil (58.9%).
ISP-MS: m/e=305.3 ([M+H$^+$])

Example 20

(R)-6-Chloro-4,9-dimethyl-1,2,3,4-tetrahydro-2,4a, 5-triaza-fluorene; hydrochloride A solution of 0.25 g (0.71 mmol) (R)-6-chloro-9-formyl-4-methyl-3,4-dihydro-1H-2,4a,5-triaza-fluorene-2-carboxylic acid tert-butyl ester in 5 ml dichloromethane was cooled to 0 deg C. Trifluoroacetic acid (5.0 ml) and, after 5 min, 0.68 ml (4.30 mmol) triethyl silane were added. The cooling bath was removed and after 7 h at room temperature the solution was poured into saturated aqueous sodium bicarbonate solution and was extracted four times with dichloromethane. The combined organic layers were washed with brine, dried over magnesium sulfate, filtered and evaporated. The residue was purified by chromatography on silica gel (0.032–0.063 mm) with dichloromethane:methanol:ammonia (49:1:0.1) as eluant. The resulting oil was dissolved in 5 ml ethyl acetate and treated dropwise with 0.22 ml of a 2.1M hydrochloric acid solution in ethyl acetate. The suspension was filtered; the filter-cake was washed with ethyl acetate and dried under high vacuum to afford the compound as a colorless solid (69.4%).
ISP-MS: m/e=236.2 ([M+H$^+$]) Elemental analysis: $C_{12}H_{15}Cl_2N_3$ (272.179) calc.: C, 52.95; H, 5.56; N, 15.44; Cl, 26.05. found[*]: C, 53.20; H, 5.71; N, 15.19; Cl, 25.82.

[#] Calculated with 0.46% water.

Intermediate (R)-6-Chloro-9-formyl-4-methyl-3,4-dihydro-1H-2, 4a,5-triaza-fluorene-2-carboxylic acid tert N,N-Dimethylformamide (10 ml) was cooled to 1 deg C. and treated dropwise with 5.1 ml (56.0 mmol) phosphorus oxychloride. After the addition the temperature was again cooled to 1 deg C. and a solution of 1.0 g (3.11 mmol) (R)-6-chloro-4-methyl-3,4-dihydro-1H-2,4a,5-triaza-fluorene-2-carboxylic acid tert-butyl ester in (Example 2, intermediate a) in 10 ml N,N-dimethylformamide was added.

The cooling bath was removed and after 1.5 h at room temperature the reaction mixture was poured into saturated aqueous sodium bicarbonate solution and was extracted three times with ethyl acetate. The combined organic phases were washed with water and brine, dried over magnesium sulfate, filtered and evaporated. The residue was purified by chromatography on silica gel (0.032–0.063 mm) with ethyl acetate:n-hexane (1:3) as eluant to yield the desired compound as a yellow foam (55.2%).

ISP-MS: m/e=350.3 ([M+H$^+$]

Example 21

(4R,9aR)-6-Benzyloxy-4-methyl-1,2,3,4,9,9a-hexahydro-2,4a,5-triaza-fluorene

This compound was prepared in analogy to Example 2 from (4R,9aR)-6-benzyloxy-4-methyl-3,4,9,9a-tetrahydro-1H-2,4a,5-triaza-fluorene-2-carboxylic acid tert-butyl ester.
Colorless oil (93.7%).
ISP-MS: m/e=296.4 ([M+H$^+$])

Intermediate (4R,9aR)-6-Benzyloxy-4-methyl-3,4,9,9a-tetrahydro-1H-2,4a,5-triaza-fluorene-2-carboxylic acid tert-butyl ester To a solution of 3.0 g (8.15 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 30 ml toluene was added 0.20 g (0.29 mmol) (S)-(−)-2,2'-bis(di-p-tolylphosphino)-1,1'-binaphthyl and 0.12 g (0.12 mmol) di-palladium-tris(dibenzylideneacetone)chloroform complex. After 30 min, 1.0 ml (1.06 g, 9.80 mmol) benzylalcohol and 0.70 g (16.0 mmol) sodium hydride (55–65% dispersion in oil) were added and the reaction mixture was stirred for 3.5 h at 70 deg C. After cooling to room temperature, the reaction mixture was poured onto 10% aqueous sodium carbonate solution and extracted three times with ethyl acetate. The combined organic phases were washed with brine, dried over magnesium sulfate and filtered. After evaporation of the volatile components, the residue was chromatographed on silica gel (0.032–0.063 mm) with ethyl acetate:n-hexane (1:4) as eluant.
Yellow oil (62.0%).
ISP-MS: m/e=396.4 ([M+H$^+$])

Example 22

(4R,9aR)-6-Methoxy-4-methyl-1,2,3,4,9,9a-hexahydro-2,4a,5-triaza-fluorene

This compound was prepared in analogy to Example 2 from (4R,9aR)-6-methoxy-4-methyl-3,4,9,9a-tetrahydro-1H-2,4a,5-triaza-fluorene-2-carboxylic acid tert-butyl ester.
Colorless solid (95.4%).
ISP-MS: m/e=220.4 ([M+H$^+$])

Intermediates a) (4R,9aR)-6-Hydroxy-4-methyl-3,4,9,9a-tetrahydro-1H-2,4a,5-triaza-fluorene-2-carboxylic acid tert-butyl ester To a solution of 3.90 g (9.86 mmol) (4R,9aR)-6-benzyloxy-4-methyl-3,4,9,9a-tetrahydro-1H-2,4a,5-triaza-fluorene-2-carboxylic acid tert-butyl ester (Example 21, intermediate) in 30 ml methanol:ethyl acetate (1:1 v/v) 0.20 g 10% palladium on charcoal was added and the reaction was hydrogenated at atmospheric pressure for 2 h. After filtration over dicalite speed plus the filtrate was evaporated and the residue was chromatographed on silica gel (0.032–0.063 mm) with ethyl acetate:n-hexane (1:1) as eluant to afford the desired compound as a colorless foam (82.0%).
ISP-MS: m/e=306.4 ([M+H$^+$])

b) (4R,9aR)-6-Methoxy-4-methyl-3,4,9,9a-tetrahydro-1H-2,4a,5-triaza-fluorene-2-carboxylic acid tert-butyl ester To a solution of 0.25 g (0.82 mmol) (4R,9aR)-6-hydroxy-4-methyl-3,4,9,9a-tetrahydro-1H-2,4a,5-triaza-fluorene-2-carboxylic acid tert-butyl ester in 2 ml N,N-dimethylformamide, 40 mg (0.90 mmol) sodium hydride (55–65% dispersion in oil) was added. After 30 min, 0.10 ml (0.23 g, 1.64 mmol) methyl iodide was added. After 1 h the reaction mixture was poured onto water and extracted three times with ethyl acetate. The organic layers were washed twice with water, then brine and were dried over magnesium sulfate. After filtration and evaporation of the solvent the product was purified by column chromatography on silica gel (0.032–0.063 mm) with ethyl acetate:n-hexane (1:5) as eluant.
Colorless oil (80.3%).
ISP-MS: m/e=320.4 ([M+H$^+$])

Example 23

(4R,9aR)-6-Ethoxy-4-methyl-1,2,3,4,9,9a-hexahydro-2,4a,5-triaza-fluorene

This compound was prepared in analogy to Example 2 from (4R,9aR)-6-ethoxy-4-methyl-3,4,9,9a-tetrahydro-1H-2,4a,5-triaza-fluorene-2-carboxylic acid tert-butyl ester.
Light yellow oil (87.8%).
ISP-MS: m/e=234.4 ([M+H$^+$])

Intermediate (4R,9aR)-6-Ethoxy-4-methyl-3,4,9,9a-tetrahydro-1H-2,4a,5-triaza-fluorene-2-carboxylic tert-butyl ester This compound was prepared in analogy to Example 22 intermediate b), from (4R,9aR)-6-hydroxy-4-methyl-3,4,9,9a-tetrahydro-1H-2,4a,5-triaza-fluorene-2-carboxylic acid tert-butyl ester, sodium hydride and ethyl bromide.
Colorless oil (64.6%).
ISP-MS: m/e=334.3 ([M+H$^+$])

Example 24

(4R,9aR)-2-(4-Methyl-1,2,3,4,9,9a-hexahydro-2,4a,5-triaza-fluoren-6-yloxy)-ethanol This compound was prepared in analogy to Example 2 from (4R,9aR)-6-(2-hydroxy-ethoxy)-4-methyl-3,4,9,9a-tetrahydro-1H-2,4a,5-triaza-fluorene-2-carboxylic acid tert-butyl ester.
Light brown solid (84.1%).
ISP-MS: m/e=250.3 ([M+H$^+$])

Intermediate (4R,9aR)-6-(2-Hydroxy-ethoxy)-4-methyl-3,4,9,9a-tetrahydro-1H-2,4a,5-triaza-fluorene-2-carboxylic acid tert-butyl ester This compound was prepared in analogy to Example 22 intermediate b), from (4R,9aR)-6-hydroxy-4-methyl-3,4,9,9a-tetrahydro-1H-2,4a,5-triaza-fluorene-2-carboxylic acid tert-butyl ester, sodium hydride and 2-bromoethanol.
Colorless oil (48.9%).
ISP-MS: m/e=350.5 ([M+H$^+$])

Example 25

(4R,9aR)-6-(2-Methoxy-ethoxy)-4-methyl-1,2,3,4,9,9a-hexahydro-2,4a,5-triaza-fluorene This compound was prepared in analogy to Example 2 from (4R,9aR)-6-(2-methoxy-ethoxy)-4-methyl-3,4,9,9a-tetrahydro-1H-2,4a,5-triaza-fluorene-2-carboxylic acid tert-butyl ester.
Light brown oil (97.3%).
ISP-MS: m/e=264.3 ([M+H$^+$])

Intermediate (4R,9aR)-6-(2-Methoxy-ethoxy)-4-methyl-3,4,9,9a-tetrahydro-1H-2,4a,5-triaza-fluorene-2-carboxylic acid tert-butyl ester This compound was prepared in analogy to Example 22 intermediate b), from (4R,9aR)-6-hydroxy-4-methyl-3,4,9,9a-tetrahydro-1H-2,4a,5-triaza-fluorene-2-carboxylic acid tert-butyl ester, sodium hydride and 2-bromoethyl methyl ether.
Colorless oil (72.3%).
ISP-MS: m/e=364.3 ([M+H$^+$])

Example 26

(4R,9aR)-6-Cyclobutylmethoxymethyl-4-methyl-1,2,3,4,9,9a-hexahydro-2,4a,5-triaza-fluorene This compound was prepared in analogy to Example 2 from (4R,9aR)-6-cyclobutylmethoxymethyl-4-methyl-3,4,9,9a-tetrahydro-1H-2,4a,5-triaza-fluorene-2-carboxylic acid tert-butyl ester.
Yellow oil (78.8%).
ISP-MS: m/e=288.3 ([M+H$^+$])

Intermediate (4R,9aR)-6-Cyclobutylmethoxymethyl-4-methyl-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester, sodium hydride and (bromomethyl)cyclobutane.

Light yellow oil (16.2%).
ISP-MS: m/e=388.4 ([M+H$^+$])

Example 27

(4R,9aR)-6-Ethoxymethyl-4-methyl-1,2,3,4,9,9a-hexahydro-2,4a,5-triaza-fluorene

This compound was prepared in analogy to Example 2 from (4R,9aR)-6-ethoxymethyl-4-methyl-3,4,9,9a-tetrahydro-1H-2,4a,5-triaza-fluorene-2-carboxylic acid tert-butyl ester.
Yellow oil (93.6%).
ISP-MS: m/e=248.3 ([M+H$^+$])

Intermediate (4R,9aR)-6-Ethoxymethyl-4-methyl-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester, sodium hydride and ethyl bromide.
Light yellow oil (69.6%).
ISP-MS: m/e=348.5 ([M+H$^+$])

Example 28

(4R,9aR)-6-Cyclohexylmethoxymethyl-4-methyl-1,2,3,4,9,9a-hexahydro-2,4a,5-triaza-fluorene This compound was prepared in analogy to Example 2 from (4R,9aR)-6-cyclohexylmethoxymethyl-4-methyl-3,4,9,9a-tetrahydro-1H-2,4a,5-triaza-fluorene-2-carboxylic acid tert-butyl ester.
Yellow oil (45.5%).
ISP-MS: m/e=316.3 ([M+H$^+$])

Intermediate (4R,9aR)-6-Cyclohexylmethoxymethyl-4-methyl-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester, sodium hydride and (bromomethyl)cyclohexane.
Light yellow oil (19.0%).
ISP-MS: m/e=416.4 ([M+H$^+$])

Example 29

(4R,9aR)-2-(4-Methyl-1,2,3,4,9,9a-hexahydro-2,4a,5-triaza-fluoren-6-ylmethoxy)-ethanol This compound was prepared in analogy to Example 2 from (4R,9aR)-6-(2-hydroxy-ethoxymethyl)-4-methyl-3,4,9,9a-tetrahydro-1H-2,4a,5-triaza-fluorene-2-carboxylic acid tert-butyl ester.
Light yellow oil (82.8%).
ISP-MS: m/e=264.2 ([M+H$^+$])

Intermediates a) (4R,9aR)-4-Methyl-6-[2-(tetrahydro-pyran-2-yloxy)-ethoxymethyl]-3,4,9,9a-tetrahydro-1H-2,4a,5-triaza-fluorene-2-carboxylic acid tert-butyl ester This compound was prepared in analogy to Example 15 intermediate c), from (4R,9aR)-6-hydroxymethyl-4-methyl-3,4,9,9a-tetrahydro-1H-2,4a,5-triaza-fluorene-2-carboxylic acid tert-butyl ester, sodium hydride and 2-(2-bromoethoxy)tetrahydro-2H-pyran.
Light yellow oil (30.3%).
ISP-MS: m/e=448.5 ([M+H$^+$])

b) (4R,9aR)-6-(2-Hydroxy-ethoxymethyl)-4-methyl-3,4,9,9a-tetrahydro-1H-2,4a,5-triaza-fluorene-2-carboxylic acid tert-butyl ester To the solution of 0.16 g (0.36 mmol) (4R,9aR)-4-methyl-6-[2-(tetrahydro-pyran-2-yloxy)-ethoxymethyl]-3,4,9,9a-tetrahydro-1H-2,4a,5-triaza-fluorene-2-carboxylic acid tert-butyl ester in 3 ml methanol was added 0.136 g (0.71 mmol) para-toluenesulphonic acid. After 30 min, the solvent was removed on a rotary evaporator and the residue was chromatographed on silica gel (0.032–0.063 mm) with dichloromethane:methanol:ammonia (19:1:0.1) as eluant to afford the desired compound as a light yellow oil (71.6%).
ISP-MS: m/e=364.2 ([M+H$^+$])

Example 30

(4R,9aR)-(4-Methyl-1,2,3,4,9,9a-hexahydro-2,4a,5-triaza-fluoren-6-yl)-methanol

This compound was prepared in analogy to Example 2 from (4R,9aR)-6-hydroxymethyl-4-methyl-3,4,9,9a-tetrahydro-1H-2,4a,5-triaza-fluorene-2-carboxylic acid tert-butyl ester (Example 15, intermediate b).
White solid (25.6%).
ISP-MS: m/e=220.4 ([M+H$^+$])

Example 31

(4R,9aR)-6-Isobutyl-4-methyl-1,2,3,4,9,9a-hexahydro-2,4a,5-triaza-fluorene; hydrochloride This compound was prepared in analogy to Example 2 from (4R,9aR)-6-isobutyl-4-methyl-3,4,9,9a-tetrahydro-1H-2,4a,5-triaza-fluorene-2-carboxylic acid tert-butyl ester.
Colorless solid (62.5%).
ISP-MS: m/e=246.4 ([M+H$^+$])

Intermediate (4R,9aR)-6-Isobutyl-4-methyl-3,4,9,9a-tetrahydro-1H-2,4a,5-triaza-fluorene-2-carboxylic acid tert-butyl ester To a solution of 2.0 g (5.43 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 50 ml 1,2-dimethoxyethane 0.75 g (0.65 mmol) tetrakis(triphenylphosphine)palladium was added. After 20 min, 16.3 ml (16.3 mmol) triisobutylaluminium (1M solution in n-hexane) was added and the reaction mixture was heated under reflux for 66 h. After cooling to room temperature another 8.1 ml (8.1 mmol) triisobutylaluminium (1M solution in n-hexane) was added and the reaction again heated under reflux. After 5 h the reaction was poured onto 1M aqueous sodium hydroxide solution and extracted three times with ethyl acetate. The combined organic layers were washed with brine, dried over magnesium sulfate, filtered and evaporated. The residue was chromatographed on silica gel (0.032–0.063 mm) with ethyl acetate:n-hexane (1:3) as eluant to afford the desired compound as a light brown oil (76.2%).
ISP-MS: m/e=346.4 ([M+H$^+$])

Example 32

(4R,9aR)-6-Difluoromethyl-4-methyl-1,2,3,4,9,9a-hexahydro-2,4a,5-triaza-fluorene This compound was prepared in analogy to Example 2 from (4R,9aR)-6-difluoromethyl-4-methyl-3,4,9,9a-tetrahydro-1H-2,4a,5-triaza-fluorene-2-carboxylic acid tert-butyl ester.
Light brown oil (98.0%).
ISP-MS: m/e=240.4 ([M+H$^+$])

Intermediates a) (4R,9aR)-6-Formyl-4-methyl-3,4,9,9a-tetrahydro-1H-2,4a,5-triaza-fluorene-2-carboxylic acid tert-butyl ester A solution of 2.0 g (5.43 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 15 ml tetrahydrofuran was cooled to −75 deg C. and treated with 4.40 ml (0.65 mmol) tert-butyllithium (1.5 M solution in n-pentane). After 30 min, 0.60 ml (0.63 g, 8.15 mmol) N,N-dimethylformamide was added dropwise. After 2.5 h the reaction mixture was poured onto 10% aqueous citric acid solution and extracted three times with ethyl acetate. The combined organic layers were washed with brine, dried over magnesium sulfate, filtered and evaporated. The residue was purified by flash-chromatography on silica gel (0.032–0.063 mm) with ethyl acetate:n-hexane (1:3) as eluant to afford the desired compound as a yellow oil (40.1%).
ISP-MS: m/e=319.5 ([M+H$^+$])

b) (4R,9aR)-6-Difluoromethyl-4-methyl-3,4,9,9a-tetrahydro-1H-2,4a,5-triaza-fluorene-2-carboxylic acid tert-butyl ester To a solution of 83.0 µl (0.10 g, 0.63 mmol) diethylaminosulphur trifluoride in 3 ml dichlorormethane 0.20 g (0.63 mmol) (4R,9aR)-6-formyl-4-methyl-3,4,9,9a-tetrahydro-1H-2,4a,5-triaza-fluorene-2-carboxylic acid tert-butyl ester dissolved in 3 ml dichloromethane was added and the reaction was stirred at room temperature for 5.5 h. After 1 h at reflux the reaction was poured onto water and extracted three times with ethyl acetate. The combined organic layers were washed with water and brine, dried over magnesium sulfate, filtered and evaporated. The residue was flash-chromatographed on silica gel (0.032–0.063 mm) with ethyl acetate:n-hexane (1:2) as eluant to afford the desired compound as a light brown oil (28.1%).
ISP-MS: m/e=340.3 ([M+H$^+$])

Example 33

(4R,9aR)-6-Fluoromethyl-4-methyl-1,2,3,4,9,9a-hexahydro-2,4a,5-triaza-fluorene

This compound was prepared in analogy to Example 2 from (4R,9aR)-6-fluoromethyl-4-methyl-3,4,9,9a-tetrahydro-1H-2,4a,5-triaza-fluorene-2-carboxylic acid tert-butyl ester.
Colorless oil (88.6%).
ISP-MS: m/e=222.3 ([M+H$^+$])

Intermediate (4R,9aR)-6-Fluoromethyl-4-methyl-3,4,9,9a-tetrahydro-1H-2,4a,5-triaza-fluorene-2-carboxylic acid tert-butyl ester A solution of 82.0 μl (0.11 g, 0.63 mmol) diethylaminosulphur trifluoride in 2 ml dichloromethane was cooled to −78 deg C. and treated with a solution of 0.20 g (0.63 mmol) (4R,9aR)-6-(2-hydroxy-ethoxymethyl)-4-methyl-3,4,9,9a-tetrahydro-1H-2,4a,5-triaza-fluorene-2-carboxylic acid tert-butyl ester (Example 15, intermediate b) in 2 ml dichloromethane. The cooling bath was removed and the reaction stirred for 1 h at room temperature. The solution was extracted with 10% aqueous sodium bicarbonate solution, washed with brine, dried over magnesium sulfate, filtered and evaporated. The residue was chromatographed on silica gel (0.032–0.063 mm) with ethyl acetate:n-hexane (1:2) as eluant to afford the desired compound as a colorless oil (51.7%).
ISP-MS: m/e=322.4 ([M+H$^+$])

Example 34

(4R,9aR)-1-(4-Methyl-1,2,3,4,9,9a-hexahydro-2,4a,5-triaza-fluoren-6-yl)-ethanone This compound was prepared in analogy to Example 2 from (4R,9aR)-6-acetyl-4-methyl-3,4,9,9a-tetrahydro-1H-2,4a,5-triaza-fluorene-2-carboxylic acid tert-butyl ester.
Yellow oil (93.9%).
ISP-MS: m/e=232.2 ([M+H$^+$])

Intermediate (4R,9aR)-6-Acetyl-4-methyl-3,4,9,9a-tetrahydro-1H-2,4a,5-triaza-fluorene-2-carboxylic acid tert-butyl ester Procedure 1

The solution of 0.50 g (1.0 mmol) (4R,9aR)-6-bromo-4-methyl-3,4,9,9a-tetrahydro-1H-2,4a,5-triaza-fluorene-2-carboxylic acid tert-butyl ester (Example 5, intermediate b) in 20 ml diethyl ether was cooled to −100 deg C. and treated dropwise with 1.0 ml (1.5 mmol) tert-butyllithium (1.5 M solution in n-pentane). After 30 min, 0.14 ml N,N-dimethylacetamide was added and the reaction temperature was raised to −75 deg C. After 30 min, the reaction was quenched with 10% aqueous ammonium chloride solution and extracted twice with ethyl acetate. The combined organic layers were washed with brine, dried over magnesium sulfate, filtered and evaporated. The residue was flash-chromatographed on silica gel (0.032–0.063 mm) with ethyl acetate:n-heptane (1:1) as eluant.
Yellow oil (55.4%).
ISP-MS: m/e=332.2 ([M+H$^+$])

Procedure 2

To a solution of (4R,9aR)-6-(1-hydroxy-ethyl)-4-methyl-3,4,9,9a-tetrahydro-1H-2,4a,5-triaza-fluorene-2-carboxylic acid tert-butyl ester (Example 38, intermediate) (229 mg) in CH$_2$Cl$_2$ (4 ml) was added MnO$_2$ (598 mg) under argon. The mixture was stirred at room temperature for 24 hours. Further MnO$_2$ (299 mg) was added and the mixture was stirred for 2 days. The mixture was filtered through a Celite® pad, washing with CH$_2$Cl$_2$ and the filtrate was concentrated in vacuo. The residue was purified by column chromatography [SiO$_2$; isohexane-ethyl acetate (4:1)]. A portion (15 mg) of the purified intermediate was deprotected according to the procedure described for Example 56 to afford (4R,9aR)-1-(4-methyl-1,2,3,4,9,9a-hexahydro-2,4a,5-triaza-fluoren-6-yl)-ethanone di-trifluoroacetate (37 mg) as a yellow oil: HPLC [Xterra; 20/50; 235 nm] 98.7%, 1.11 min; MS (ES) 231.0 (MH$^+$).

Example 35

(4R,9aR)-1-(4-Methyl-1,2,3,4,9,9a-hexahydro-2,4a,5-triaza-fluoren-6-yl)-propan-1-one (4R,9aR)-1-(4-Methyl-1,2,3,4,9,9a-hexahydro-2,4a,5-triaza-fluoren-6-yl)-propan-1-one di-trifluoroacetate (40 mg) was made from 6-(1-hydroxy-propyl)-4-methyl-3,4,9,9a-tetrahydro-1H-2,4a,5-triaza-fluorene-2-carboxylic acid tert-butyl ester (190 mg) according to procedure 2 described in Example 34 to afford the product as a yellow oil: HPLC [Xterra; 20/50; 220 nm] 98.0%, 2.46 min; MS (ES) 245.0 (MH$^+$).

Example 36

(4R,9aR)-1-(4-Methyl-1,2,3,4,9,9a-hexahydro-2,4a,5-triaza-fluoren-6-yl)-butan-1-one (4R,9aR)-1-(4-Methyl-1,2,3,4,9,9a-hexahydro-2,4a,5-triaza-fluoren-6-yl)-butan-1-one di-trifluoroacetate (35 mg) was made from 6-(1-hydroxy-butyl)-4-methyl-3,4,9,9a-tetrahydro-1H-2,4a,5-triaza-fluorene-2-carboxylic acid tert-butyl ester (142 mg) according to procedure 2 described in Example 34 to afford the product as a yellow oil: HPLC [Xterra; 50/80; 220 nm] 99.3%, 1.08 min; MS (ES) 259.0 (MH$^+$).

Example 37

(4R,9aR)-2,2,2-Trifluoro-1-(4-methyl-1,2,3,4,9,9a-hexahydro-2,4a,5-triaza-fluoren-6-yl)-ethanone This compound was prepared in analogy to Example 2 from (4R,9aR)-4-methyl-6-trifluoroacetyl-3,4,9,9a-tetrahydro-1H-2,4a,5-triaza-fluorene-2-carboxylic acid tert-butyl ester.
Yellow solid (40.7%).
ISP-MS: m/e=304.3 ([M+Na$^+$])

Intermediate (4R,9aR)-4-Methyl-6-trifluoroacetyl-3,4,9,9a-tetrahydro-1H-2,4a,5-triaza-fluorene-2-carboxylic acid tert-butyl ester To a solution of 0.30 g (0.86 mmol) (4R,9aR)-4-methyl-3,4,9,9a-tetrahydro-1H-2,4a,5-triaza-fluorene-2,6-dicarboxylic acid 2-tert-butyl ester 6-methyl ester (Example 15, intermediate a) in 5 ml toluene 0.16 ml (0.15 g, 1.08 mmol) (trifluoromethyl) trimethylsilane was added. The solution was cooled to −75 deg C. and 22 μl (0.022 mmol) tetrabutylammonium fluoride (1M in tetrahydrofuran) was added. The cooling bath was removed and after 2 h at room temperature the reaction was poured onto 1M hydrochloric acid and extracted with ethyl acetate. The combined organic layers were washed with brine, dried over magnesium sulfate, filtered and evaporated. The residue was flash-chromatographed on silica gel (0.032–0.063 mm) with ethyl acetate:n-hexane (1:2) as eluant to afford the desired compound as a light yellow oil (23.7%).

Example 38

(4R,9aR)-1-(RS)-(4-Methyl-1,2,3,4,9,9a-hexahydro-2,4a,5-triaza-fluoren-6-yl)-ethanol This compound was prepared in analogy to Example 2 from (4R,9aR)-6-(1-(RS)-hydroxy-ethyl)-4-methyl-3,4,9,9a-tetrahydro-1H-2,4a,5-triaza-fluorene-2-carboxylic acid tert-butyl ester.
Light brown oil (77.6%).
ISP-MS: m/e=234.3 (M+H$^+$)

Intermediate (4R,9aR)-6-(1-(RS)-Hydroxy-ethyl)-4-methyl-3,4,9,9a-tetrahydro-1H-2,4a,5-triaza-fluorene-2-carboxylic acid tert-butyl ester A solution of 6.0 g (16.3 mmol) (4R,9aR)-6-bromo-4-methyl-3,4,9,9a-tetrahydro-1H-2,4a,5-triaza-fluorene-2-carboxylic acid tert-butyl ester in 250 ml diethyl ether was cooled to −100 deg C. and treated with 11.9 ml (17.9 mmol) tert-butyllithium (1.5 M in n-pentane). After 15 min, 1.0 ml (0.79 g, 17.9 mmol) acetaldehyde was added and the reaction was stirred for 40 min at the same temperature. After warming to −75 deg C. the reaction mixture was poured onto 10% aqueous ammonium chloride solution and extracted three times with ethyl acetate. The combined organic layers were washed with brine, dried over magnesium sulfate, filtered and evaporated. The residue was chromatographed on silica gel (0.032–0.063 mm) with ethyl acetate:n-hexane (2:3) as eluant to afford a first batch of compound. The remaining product-containing fractions were pooled and chromatographed again to yield a second batch of compound (56.9% total).
Light brown oil.
ISP-MS: m/e=334.3 (M+H$^+$)

Examples 39 and 40

(4R,9aR)-6-(1-(R)-Hydroxy-ethyl)-4-methyl-3,4,9,9a-tetrahydro-1H-2,4a,5-triaza-fluorene and (4R,9aR)-6-(1-(S)-Hydroxy-ethyl)-4-methyl-3,4,9,9a-tetrahydro-1H-2,4a,5-triaza-fluorene A solution of 3.09 g (9.27 mmol) (4R,9aR)-6-(1-(RS)-hydroxy-ethyl)-4-methyl-3,4,9,9a-tetrahydro-1H-2,4a,5-triaza-fluorene-2-carboxylic acid tert-butyl ester (Example 38, intermediate) in 33 ml dichloromethane was cooled to 0 deg C. and treated with 8.8 ml (12.7 g, 0.11 mol) trifluoroacetic acid. The cooling bath was removed and the volatile components were removed on a rotary evaporator. The residue was chromatographed on silica gel (0.032–0.063 mm) with dichloromethane:methanol:ammonia (19:1:0.1). The remaining oil was dissolved in dichloromethane and saturated aqueous sodium bicarbonate solution and extracted until all product was extracted from the aqueous phase. The combined organic layers were washed with brine, dried over magnesium sulfate, filtered and evaporated. The remaining light brown oil was chromatographed on a Chiralpak-AD column with 7% ethanol/n-heptane yielding the two diastereomers, the R-diastereomer being eluted first.

Example 39

(4R,9aR)-6-(1-(R)-Hydroxy-ethyl)-4-methyl-3,4,9,9a-tetrahydro1H-2,4a,5-triaza-fluorene Light brown solid (36.5%).
ISP-MS: m/e=234.2 (M+H$^+$)

Example 40

(4R,9aR)-6-(1-(S)-Hydroxy-ethyl)-4-methyl-3,4,9,9a-tetrahydro-1H-2,4a,5-triaza-fluorene Light brown oil (38.4%).
ISP-MS: m/e=234.2 (M+H$^+$)

Example 41

(4R,9aR)-6-(1-(R)-Methoxy-ethyl)-4-methyl-1,2,3,4,9,9a-hexahydro-2,4a,5-triaza-fluorene This compound was prepared in analogy to Example 2 from (4R,9aR)-6-(1-(R)-methoxy-ethyl)-4-methyl-3,4,9,9a-tetrahydro-1H-2,4a,5-triaza-fluorene-2-carboxylic acid tert-butyl ester.
Light yellow oil (87.8%).
ISP-MS: m/e=248.2 (M+H$^+$)

Intermediates a) (4R,9aR)-6-(1-(R)-Hydroxy-ethyl)-4-methyl-3,4,9,9a-tetrahydro-1H-2,4a,5-triaza-fluorene-2-carboxylic acid tert-butyl ester To a solution of 0.68 g (2.91 mmol) (4R,9aR)-6-(1-(R)-hydroxy-ethyl)-4-methyl-3,4,9,9a-tetrahydro-1H-2,4a,5-triaza-fluorene (Example 39) in 5 ml dichloromethane were added 0.70 g (0.32 mmol) di-tert-butyldicarbonate and 17.8 mg (0.15 mmol) 4-(dimethylamino)pyridine. After 1 h the solvent was evaporated and the residue was chromatographed on silica gel (0.032–0.063 mm) with ethyl acetate: n-heptane (1:2) as eluant.
Colorless foam (77.7%).
ISP-MS: m/e =334.3 (M+H$^+$)

b) (4R,9aR)-6-(1-(R)-Methoxy-ethyl)-4-methyl-3,4,9,9a-tetrahydro-1H-2,4a,5-triaza-fluorene-2-carboxylic acid tert-butyl ester To a solution of 0.75 g (2.25 mmol) (4R,9aR)-6-(1-(R)-hydroxy-ethyl)-4-methyl-3,4,9,9a-tetrahydro-1H-2,4a,5-triaza-fluorene-2-carboxylic acid tert-butyl ester in 5 ml N,N-dimethylformamide was added 0.12 g (2.70 mmol) sodium hydride (55–65% dispersion in oil). After 30 min, 0.28 ml (0.64 g, 4.50 mmol) methyl iodide was added and the reaction mixture was stirred at 50 deg C. for 2 h. After cooling to room temperature the reaction mixture, was poured onto 10% aqueous ammonium chloride solution and extracted three times with ethyl acetate. The combined organic layers were washed with brine, dried over magnesium sulfate, filtered and evaporated. The residue was chromatographed on silica gel (0.032–0.063 mm) with ethyl acetate:n-heptane (1:2) as eluant.
Yellow oil (89.6%).
ISP-MS: m/e=348.4 (M+H$^+$)

Example 42

(4R,9aR)-6-(1-(S)-Methoxy-ethyl)-4-methyl-1,2,3,4,9,9a-hexahydro-2,4a,5-triaza-fluorene This compound was prepared in analogy to Example 2 from (4R,9aR)-6-(1-(S)-methoxy-ethyl)-4-methyl-3,4,9,9a-tetrahydro-1H-2,4a,5-triaza-fluorene-2-carboxylic acid tert-butyl ester.

Light yellow oil (94.2%).
ISP-MS: m/e=248.2 (M+H$^+$)

Intermediates a) (4R,9aR)-6-(1-(S)-Hydroxy-ethyl)-4-methyl-3,4,9,9a-tetrahydro-1H-2,4a,5-triaza-fluorene-2-carboxylic acid tert-butyl ester This compound was prepared in analogy to Example 41 intermediate a), from (4R,9aR)-6-(1-(S)-hydroxy-ethyl)-4-methyl-3,4,9,9a-tetrahydro-1H-2,4a,5-triaza-fluorene (Example 40), di-tert-butyldicarbonate and 4-(dimethylamino)pyridine.

Colorless foam (94.4%).
ISP-MS: m/e=334.3 (M+H$^+$)

Alternatively, this compound was obtained in the following way:

To a stirred solution of (R)-Me-CBS-oxazaborolidine (770 μl, 1M in toluene) in THF (3 ml) was added borane-dimethylsulfide (770 μl, 2M in THF) at 0° C. under nitrogen. A solution was stirred for 5 mins, then 6-acetyl-4-methyl-3,4,9,9a-tetrahydro-1H-2,4a,5-triaza-fluorene-2-carboxylic acid tert-butyl ester (Example 34, intermediate b) (255 mg) in THF (2.5 ml) was added dropwise over 45 mins. A solution was stirred at 0° C. for 3 hours, quenched with methanol and partitioned between aqueous ammonium chloride and EtOAc. The phases were separated and the organic layer was washed with brine, dried (MgSO$_4$) and concentrated in vacuo. The residue was purified by column chromatography [SiO$_2$; isohexane-ethyl acetate (1:1)] to afford 6-((1S)-1-hydroxy-ethyl)-(4R,9aR)-4-methyl-3,4,9,9a-tetrahydro-1H-2,4a,5-triaza-fluorene-2-carboxylic acid tert-butyl ester (185 mg) as a colorless oil: $^1$H NMR (400 MHz, CDCl$_3$): 7.16 (1H, d, J 7 Hz), 6.35 (1H, d, J 7 Hz), 4.37–4.31 (1H, br s), 4.31–4.19 (1H, br s), 4.09–3.95 (1H, m), 3.95–3.85 (1H, m), 3.13–2.94 (2H, m), 2.79–2.55 (1H, br s), 2.54 (1H, dd, J 6 and 16 Hz), 1.48 (9H, s), 1.44 (3H, d, J 6.5 Hz) and 1.24 (3H, d, J 6.5 HZ); MS (ES) 334.3 (MH$^+$).

b) (4R,9aR)-6-(1-(S)-Methoxy-ethyl)-4-methyl-3,4,9,9a-tetrahydro-1H-2,4a,5-triaza-fluorene-2-carboxylic acid tert-butyl ester This compound was prepared in analogy to Example 41 intermediate b), from (4R,9aR)-6-(1-(S)-hydroxy-ethyl)-4-methyl-3,4,9,9a-tetrahydro-1H--2,4a,5-triaza-fluorene-2-carboxylic acid tert-butyl ester.

Yellow oil (88.7%).
ISP-MS: m/e=348.4 (M+H$^+$)

Example 43

(4R,9aR)-6-(1-(R)-Ethoxy-ethyl)-4-methyl-1,2,3,4,9,9a-hexahydro-2,4a,5-triaza-fluorene This compound was prepared in analogy to Example 2 from (4R,9aR)-6-(1-(R)-ethoxy-ethyl)-4-methyl-3,4,9,9a-tetrahydro-1H-2,4a,5-triaza-fluorene-2-carboxylic acid tert-butyl ester, prepared in analogy to Example 41, intermediates a) and b).

Light yellow oil (86.1%).
ISP-MS: m/e=262.2 (M+H$^+$)

Example 44

(4R,9aR)-6-(1-(R)-Cyclopropylmethoxy-ethyl)-4-methyl-1,2,3,4,9,9a-hexahydro-2,4a,5-triaza-fluorene This compound was prepared in analogy to Example 2 from (4R,9aR)-6-(1-(R)-cyclopropylmethoxy-ethyl)-4-methyl-3,4,9,9a-tetrahydro-1H-2,4a,5-triaza-fluorene-2-carboxylic acid tert-butyl ester, prepared in analogy to Example 41, intermediates a) and b).

Light yellow oil (90.4%).
ISP-MS: m/e=288.2 (M+H$^+$)

Example 45

(4R,9aR)-6-(1-(S)-Ethoxy-ethyl)-4-methyl-1,2,3,4,9,9a-hexahydro-2,4a,5-triaza-fluorene This compound was prepared in analogy to Example 2 from (4R,9aR)-6-(1-(S)-ethoxy-ethyl)-4-methyl-3,4,9,9a-tetrahydro-1H-2,4a,5-triaza-fluorene-2-carboxylic acid tert-butyl ester, prepared in analogy to Example 41, intermediates a) and b).

Colorless oil (96.1%).
ISP-MS: m/e=262.2 (M+H$^+$)

Example 46

(4R,9aR)-6-(1-(S)-Cyclopropylmethoxy-ethyl)-4-methyl-1,2,3,4,9,9a-hexahydro-2,4a,5-triaza-fluorene This compound was prepared in analogy to Example 2 from (4R,9aR)-6-(1-(S)-cyclopropylmethoxy-ethyl)-4-methyl-3,4,9,9a-tetrahydro-1H-2,4a,5-triaza-fluorene-2-carboxylic acid tert-butyl ester, prepared in analogy to Example 41, intermediates a) and b).

Light yellow oil (89.9%).
ISP-MS: m/e=288.2 (M+H$^+$)

Examples 47 and 48

(4R,9aR)-3,3,3-Trifluoro-1-(4-methyl-1,2,3,4,9,9a-hexahydro-2,4a,5-triaza-fluoren-6-yl)-(R)-propan-1-ol and (4R,9aR)-3,3,3-Trifluoro-1-(4-methyl-1,2,3,4,9,9a-hexahydro-2,4a,5-triaza-fluoren-6-yl)-(S)-propan-1-ol These compounds were prepared in analogy to Examples 39 and 40 from (4R,9aR)-4-methyl-6-((RS)-3,3,3-trifluoro-1-hydroxy-propyl)-3,4,9,9a-tetrahydro-1H-2,4a,5-triaza-fluorene-2-carboxylic acid tert-butyl ester and subsequent separation of the diastereomers.

Example 47

(4R,9aR)-3,3,3-Trifluoro-1-(4-methyl-1,2,3,4,9,9a-hexahydro-2,4a,5-triaza-fluoren-6-yl)-(R)-propan-1-ol Light brown solid (50.9%).
ISP-MS: m/e=302.1 ([M+H⁺])

Example 48

(4R,9aR)-3,3,3-Trifluoro-1-(4-methyl-1,2,3,4,9,9a-hexahydro-2,4a,5-triaza-fluoren-6-yl)-(S)-propan-1-ol Colorless solid (36.4%).
ISP-MS: m/e=302.1 ([M+H⁺])

Intermediate (4R,9aR)-4-Methyl-6-((RS)-3,3,3-trifluoro-1-hydroxy-propyl)-3,4,9,9a-tetrahydro-1H-2,4a,5-triaza-fluorene-2-carboxylic acid tert-butyl ester This compound was prepared in analogy to Example 38 intermediate, from (4R,9aR)-6-bromo-4-methyl-3,4,9,9a-tetrahydro-1H-2,4a,5-triaza-fluorene-2-carboxylic acid tert-butyl ester (Example 5, intermediate b), tert-butyllithium and 3,3,3-trifluoropropanal.
Light brown oil (50.5%).
ISP-MS: m/e 402.4 ([M+H⁺])

Examples 49 and 50

(4R,9aR)-(R)-(4-Methyl-1,2,3,4,9,9a-hexahydro-2,4a,5-triaza-fluoren-6-yl)-thiazol-2-yl-methanol and (4R,9aR)-(S)-(4-Methyl-1,2,3,4,9,9a-hexahydro-2,4a,5-triaza-fluoren-6-yl)-thiazol-2-yl-methanol These compounds were prepared in analogy to Examples 39 and 40 from (4R,9aR)-6-((RS)-hydroxy-thiazol-2-yl-methyl)-4-methyl-3,4,9,9a-tetrahydro-1H-2,4a,5-triaza-fluorene-2-carboxylic acid tert-butyl ester and subsequent separation of the diastereomers.

Example 49

(4R,9aR)-(R)-(4-Methyl-1,2,3,4,9,9a-hexahydro-2,4a,5-triaza-fluoren-6-yl)-thiazol-2-yl-methanol Light yellow foam (29.6%).
ISP-MS: m/e=303.2 ([M+H⁺])

Example 50

(4R,9aR)-(S)-(4-Methyl-1,2,3,4,9,9a-hexahydro-2,4a,5-triaza-fluoren-6-yl)-thiazol-2-yl-methanol Light yellow foam (41.9%).
ISP-MS: m/e=303.2 ([M+H⁺])

Intermediate (4R,9aR)-6-((RS)-Hydroxy-thiazol-2-yl-methyl)-4-methyl-3,4,9,9a-tetrahydro-1H-2,4a,5-triaza-fluorene-2-carboxylic acid tert-butyl ester This compound was prepared in analogy to Example 38 intermediate, from (4R,9aR)-6-bromo-4-methyl-3,4,9,9a-tetrahydro-1H-2,4a,5-triaza-fluorene-2-carboxylic acid tert-butyl ester (Example 5, intermediate b), tert-butyllithium and 2-thiazolecarboxadlehyde.
Colorless foam (82.3%).
ISP-MS: m/e=403.4 ([M+H⁺])

Example 51

(4R,9aR)-2-(4-Methyl-1,2,3,4,9,9a-hexahydro-2,4a,5-triaza-fluoren-6-yl)-propan-2-ol This compound was prepared in analogy to Example 2 from (4R,9aR)-6-(1-hydroxy-1-methyl-ethyl)-4-methyl-3,4,9,9a-tetrahydro-1H-2,4a,5-triaza-fluorene-2-carboxylic acid tert-butyl ester.
Light yellow oil (73.5%).
ISP-MS: m/e=248.3 ([M+H⁺])

Intermediate (4R,9aR)-6-(1-Hydroxy-1-methyl-ethyl)-4-methyl-3,4,9,9a-tetrahydro-1H-2,4a,5-triaza-fluorene-2-carboxylic acid tert-butyl ester A solution of 0.30 g (0.81 mmol) (4R,9aR)-6-bromo-4-methyl-3,4,9,9a-tetrahydro-1H-2,4a,5-triaza-fluorene-2-carboxylic acid tert-butyl ester in 5 ml tetrahydrofuran was cooled to −78 deg C. and treated with 0.61 ml (0.98 mmol) n-butyllithium solution (1.6 M in n-hexane). After 30 min, 80 µL (71 mg, 1.22 mmol) acetone was added. After 30 min, the reaction was quenched with 10% aqueous ammonium chloride and extracted with ethyl acetate. The organic layer was washed with brine, dried over magnesium sulfate and filtered. The solvent was removed on a rotary evaporator and the residue was chromatographed on silica gel (0.032–0.063 mm) with ethyl acetate:n-hexane (1:1) as eluant to afford the compound as a light yellow foam (24.4%).
ISP-MS: m/e=348.5 ([M+H⁺])

Example 52

(4R,9aR)-3-Methyl-2-(RS)-(4-methyl-1,2,3,4,9,9a-hexahydro-2,4a,5-triaza-fluoren-6-yl)-butan-2-ol This compound was prepared in analogy to Example 2 from (4R,9aR)-6-(1-(RS)-hydroxy-1,2-dimethyl-propyl)-4-methyl-3,4,9,9a-tetrahydro-1H-2,4a,5-triaza-fluorene-2-carboxylic acid tert-butyl ester.
Light yellow oil (79.5%).
ISP-MS: m/e=276.2 ([M+H⁺])

Intermediate (4R,9aR)-6-(1-(RS)-Hydroxy-1,2-dimethyl-propyl)-4-methyl-3,4,9,9a-tetrahydro-1H-2,4a,5-triaza-fluorene-2-carboxylic acid tert-butyl ester This compound was prepared in analogy to Example 51 intermediate, from (4R,9aR)-6-bromo-4-methyl-3,4,9,9a-tetrahydro-1H-2,4a,5-triaza-fluorene-2-carboxylic acid tert-butyl ester (Example 5, intermediate b), n-butyllithium and 3-methyl-2-butanone.

Colorless oil (39.8%).
ISP-MS: m/e=374.5 ([M+H$^+$])

Example 53

(4R,9aR)-1-Methoxy-2-(RS)-(4-methyl-1,2,3,4,9,9a-hexahydro-2,4a,5-triaza-fluoren-6-yl)-propan-2-ol This compound was prepared in analogy to Example 2 from (4R,9aR)-6-(1-(RS)-hydroxy-2-methoxy-1-methyl-ethyl)-4-methyl-3,4,9,9a-tetrahydro-1H-2,4a,5-triaza-fluorene-2-carboxylic acid tert-butyl ester.

Light yellow oil (84.6%).
ISP-MS: m/e=278.2 ([M+H$^+$])

Intermediate (4R,9aR)-6-(1-(RS)-Hydroxy-2-methoxy-1-methyl-ethyl)-4-methyl-3,4,9,9a-tetrahydro-1H-2,4a,5-triaza-fluorene-2-carboxylic acid tert-butyl ester This compound was prepared in analogy to Example 51, intermediate, from (4R,9aR)-6-bromo-4-methyl-3,4,9,9a-tetrahydro-1H-2,4a,5-triaza-fluorene-2-carboxylic acid tert-butyl ester (Example 5, intermediate b), n-butyllithium and methoxy-2-propanone.

Colorless oil (46.5%).
ISP-MS: m/e=378.4 ([M+H$^+$])

Example 54

(4R,9aR)-5-Chloro-2-(RS)-(4-methyl-1,2,3,4,9,9a-hexahydro-2,4a,5-triaza-fluoren-6-yl)-pentan-2-ol This compound was prepared in analogy to Example 2 from (4R,9aR)-6-(4-chloro-1-(RS)-hydroxy-1-methyl-butyl)-4-methyl-3,4,9,9a-tetrahydro-1H-2,4a,5-triaza-fluorene-2-carboxylic acid tert-butyl ester.

Colorless oil (77.8%).
ISP-MS: m/e=310.2 ([M+H$^+$])

Intermediate (4R,9aR)-6-(4-Chloro-1-(RS)-hydroxy-1-methyl-butyl)-4-methyl-3,4,9,9a-tetrahydro-1H-2,4a,5-triaza-fluorene-2-carboxylic acid tert-butyl ester A solution of 0.30 g (0.81 mmol) (4R,9aR)-6-bromo-4-methyl-3,4,9,9a-tetrahydro-1H-2,4a,5-triaza-fluorene-2-carboxylic acid tert-butyl ester in 20 ml diethyl ether was cooled to −100 deg C. and treated dropwise with 65 μl (0.97 mmol) tert-butyllithium (1.5 M solution in n-pentane). After 15 min, 0.12 g (0.11 ml, 0.98 mmol) 5-chloro-2-pentanone was added, the temperature was allowed to rise to −75 deg C. and after an additional 15 min, the reaction was quenched with 10%. aqueous ammonium chloride solution and extracted with ethyl acetate. The organic layer was washed with brine, dried over magnesium sulfate and filtered. The solvent was removed on a rotary evaporator and the residue was chromatographed on silica gel (0.032–0.063 mm) with ethyl acetate:n-hexane (1:2) as eluant to afford the compound as a colorless oil (50.9%).

ISP-MS: m/e=410.4 ([M+H$^+$])

Example 55

(4R,9aR)4-Methyl-6-(2-(RS)-methyl-tetrahydro-furan-2-yl)-1,2,3,4,9,9a-hexahydro-2,4a,5-triaza-fluorene This compound was prepared in analogy to Example 2 from (4R,9aR)-4-methyl-6-(2-methyl-tetrahydro-furan-(RS)-2-yl)-3,4,9,9a-tetrahydro-1H-2,4a,5-triaza-fluorene-2-carboxylic acid tert-butyl ester.

Colorless oil (94.1%).
ISP-MS: m/e=274.2 ([M+H$^+$])

Intermediate (4R,9aR)-4-Methyl-6-(2-methyl-tetrahydro-furan-(RS)-2-yl)-3,4,9,9a-tetrahydro-1H-2,4a,5-triaza-fluorene-2-carboxylic acid tert-butyl ester To a solution of 0.20 g (0.49 mmol) (4R,9aR)-6-(4-chloro-1-(RS)-hydroxy-1-methyl-butyl)-4-methyl-3,4,9,9a-tetrahydro-1H-2,4a,5-triaza-fluorene-2-carboxylic acid tert-butyl ester (Example 49, intermediate) in 2.0 ml N,N-dimethylformamide was added 25.5 mg (0.59 mmol) sodium hydride (55–65% dispersion in oil). After 1 h the reaction mixture was poured onto 10% aqueous ammonium chloride solution and extracted with ethyl acetate. The organic layer was washed with brine, dried over magnesium sulfate and filtered. The solvent was removed on a rotary evaporator and the residue was chromatographed on silica gel (0.032–0.063 mm) with ethyl acetate:n-hexane (1:3) as eluant to afford the compound as a colorless oil (78.5%).

ISP-MS: m/e=347.5 ([M+H$^+$])

Example 56

(4R,9aR)-6-((RS)-1-Fluoro-ethyl)-4-methyl-1,2,3,4,9,9a-hexahydro-2,4a,5-triaza-fluorene; di-trifluoroacetate To a stirred solution of (4R,9aR)-6-(1-hydroxy-ethyl)-4-methyl-3,4,9,9a-tetrahydro-1H-2,4a,5-triaza-fluorene-2-carboxylic acid tert-butyl ester (92 mg) in CH$_2$Cl$_2$ (3 ml) at 0° C. under argon was added DAST (73 μl). The solution was stirred for 1 hour and partitioned between CH$_2$Cl$_2$ and aqueous NaHCO$_3$. The phases were separated, the organics washed with brine, dried (MgSO$_4$) and concentrated in vacuo. The residue was purified by column chromatography [SiO$_2$; isohexane-ethyl acetate (4:1)]. The purified product was dissolved in CH$_2$Cl$_2$ (1 ml) and trifluoroacetic acid (1 ml) was added. The solution was left to stand at room temperature for 1 hour and concentrated in vacuo to afford (4R,9aR)-6-((RS)-1-fluoro-ethyl)-4-methyl-1,2,3,4,9,9a-hexahydro-2,4a,5-triaza-fluorene di-trifluoroacetate (50 mg) as a yellow oil: HPLC [Xterra; 50/80; 235 nm] 97%, 0.71 min; MS (ES) 235.0 (MH$^+$).

Intermediate (4R,9aR)-6-(1-hydroxy-ethyl)-4-methyl-3,4,9,9a-tetrahydro-1H-2,4a,5-triaza-fluorene-2-carboxylic acid tert-butyl ester To a stirred solution of (4R,9aR)-6-bromo-4-methyl-3,4,9,9a-tetrahydro-1H-2,4a,5-triaza-fluorene-2-carboxylic acid tert-butyl ester (Example 5, intermediate b) (2 g) in THF (24 ml) at −78° C. was added n-butyllithium (2.72 ml, 2.5 M in hexanes) dropwise. The solution was stirred at −78° C. for 45 mins and acetaldehyde (604 μl) in THF (2 ml) was added dropwise. The solution was stirred for a further 2 hours, allowed to warm to room temperature slowly and stirred for a further 4.5 hours. The reaction was quenched with aqueous ammonium chloride (20 ml), diluted with ethyl acetate and the phases separated. The organics were washed successively with water and brine, dried (MgSO$_4$) and concentrated in vacuo. The residue was purified by column chromatography [SiO$_2$; isohexane-ethyl acetate (3:2)] to afford (4R,9aR)-6-(1-hydroxy-ethyl)-4-methyl-3,4,9,9a-tetrahydro-1H-2,4a,5-triaza-fluorene-2-carboxylic acid tert-butyl ester (742 mg) as a yellow oil: $^1$H NMR (400 MHz, CDCl$_3$) 7.16 (1H, d, J 7 Hz), 6.35 (1H, d, J 7 Hz), 4.37–4.31 (1H, br s), 4.31–4.19 (1H, br s), 4.09–3.95 (1H, m), 3.95–3.85 (1H, m), 3.13–2.94 (2H, m), 2.79–2.55 (1H, br s), 2.54 (1H, dd, J 6 and 16 Hz), 1.48 (9H, s), 1.44 (3H, d, J 6.5 Hz), 1.25 (1.5H, R epimer, d, J 6.5 Hz) and 1.24 (1.5H, S epimer, d, J 6.5 HZ); MS (ES) 334.3 (MH$^+$).

Example 57

(4R,9aR)-6-((RS)-1-Fluoro-propyl)-4-methyl-1,2,3,4,9,9a-hexahydro-2,4a,5-triaza-fluorene (4R,9aR)-6-((RS)-1-Fluoro-propyl)-4-methyl-1,2,3,4,9,9a-hexahydro-2,4a,5-triaza-fluorene (59 mg) was made from (4R,9aR)-6-(1-hydroxy-propyl)-4-methyl-3,4,9,9a-tetrahydro-1H-2,4a,5-triaza-fluorene-2-carboxylic acid tert-butyl ester (52 mg) using the procedure described in Example 56 to afford the product as a colorless oil: HPLC [Xterra; 20/50; 250 nm] 100%, 2.17 min; MS (ES) 250.3 (MH$^+$).

Intermediate (4R,9aR)-6-(1-Hydroxy-propyl)-4-methyl-3,4,9,9a-tetrahydro-1H-2,4a,5-triaza-fluorene-2-carboxylic acid tert-butyl ester (4R,9aR)-6-(1-Hydroxy-propyl)-4-methyl-3,4,9,9a-tetrahydro-1H-2,4a,5-triaza-fluorene-2-carboxylic acid tert-butyl ester (465 mg) was made from (4R,9aR)-6-bromo-4-methyl-1,2,3,4,9,9a-hexahydro-2,4a,5-triaza-fluorene (Example 5, intermediate b) (1 g), using propionaldehyde (390 μl) in place of acetaldehyde, according to the procedure described in Example 56, intermediate, to afford the product as a pale yellow solid (465 mg): $^1$H NMR (400 MHz, CDCl$_3$) 7.15 (1H, d, J 7 Hz), 6.33 (1H, d, J 7 Hz), 4.47 (1H, t, J 5.5 Hz), 4.42–4.30 (1H, br s), 4.29–4.14 (1H, br s), 4.02–3.92 (2H, m), 3.92–3.83 (1H, br s), 3.11–2.94 (2H, m), 2.81–2.58 (1H, br s), 2.52 (1H, dd, J 6 and 16 Hz), 1.85–1.72 (1H, m), 1.72–1.56 (1H, m), 1.48 (9H, s), 1.24 (1.5H, epimer, 1, d, J 7 Hz), 1.23 (1.5H, epimer 2, d, J 7 Hz), 0.95 (1.5H, epimer 1, t, J 7.5 Hz) and 0.94 (1.5H, epimer 2, t, J 7.5 Hz); MS (ES) 348.0 (MH$^+$).

Example 58

(4R,9aR)-6-((RS)-1-Fluoro-butyl)-4-methyl-1,2,3,4,9,9a-hexahydro-2,4a,5-triaza-fluorene (4R,9aR)-6-((RS)-1-Fluoro-butyl)-4-methyl-1,2,3,4,9,9a-hexahydro-2,4a,5-triaza-fluorene di-trifluoroacetate (47 mg) was made from 6-(1-hydroxy-butyl)-4-methyl-3,4,9,9a-tetrahydro-1H-2,4a,5-triaza-fluorene-2-carboxylic acid tert-butyl ester (54 mg) according to the procedures described in Example 56 to afford the product as a colorless oil: HPLC [Xterra; 50/80; 255 nm] 98.6%, 1.60 min; MS (ES) 264.0 (MH$^+$).

Intermediate (4R,9aR)-6-(1-Hydroxy-butyl)-4-methyl-3,4,9,9a-tetrahydro-1H-2,4a,5-triaza-fluorene-2-carboxylic acid tert-butyl ester (4R,9aR)-6-(1-Hydroxy-butyl)-4-methyl-3,4,9,9a-tetrahydro-1H-2,4a,5-triaza-fluorene-2-carboxylic acid tert-butyl ester (430 mg) was made from (4R,9aR)-6-bromo-4-methyl-1,2,3,4,9,9a-hexahydro-2,4a,5-triaza-fluorene (Example 5, intermediate b) (1 g), using butyraldehyde (487 μl) in place of acetaldehyde, according to the procedure described in Example 56, intermediate, to afford the product as an off-white solid (420 mg): $^1$H NMR (400 MHz, CDCl$_3$) 7.14 (1H, d, J 7 Hz), 6.33 (1H, d, J 7 Hz), 4.56–4.48 (1H, m), 4.40–4.29 (1H, br s), 4.26–4.13 (1H, br s), 4.03–3.93 (2H, m), 3.93–3.86 (1H, br s), 3.11–2.92 (2H, m), 2.77–2.57 (1H, br s), 2.51 (1H, dd, J 6 and 16 Hz), 1.77–1.58 (2H, m), 1.48 (9H, s), 1.48–1.39 (2H, m), 1.24 (1.5H, epimer 1, d, J 7 Hz), 1.23 (1.5H, epimer 2, d, J 7 Hz), 0.94 (1.5H, epimer 1, t, J 7.5 Hz) and 0.93 (1.5H, epimer 2, t, J 7.5 Hz); MS (ES) 362.1 (MH$^+$).

Example 59

(4R,9aR)-6-Ethylsulfanyl-4-methyl-1,2,3,4,9,9a-hexahydro-2-4a,5-triaza-fluorene (4R,9aR)-6-Ethylsulfanyl-4-methyl-3,4,9,9a-tetrahydro-1H-2,4a,5-triaza-fluorene-2-carboxylic acid tert-butyl ester THF (5 mL) was cooled to −78° C. under an argon atmosphere. n-Butyl lithium (1.6 M in hexanes, 0.5 mL, 0.8 mmol) was added and the mixture was stirred at −78° C. for 5 min. A mixture of (4R,9aR)-6-bromo-4-methyl-3,4,9,9a-tetrahydro-1H-2,4a,5-triaza-fluorene-2-carboxylic acid tert-butyl ester (Example 5, intermediate b) (0.2 g, 0.54 mmol) in THF (5 mL) was added dropwise, maintaining the temperature below −70° C. The resultant dark red solution was stirred at −78° C. for 30 min and ethyl disulfide (0.13 mL, 1.08 mmol) was added. The mixture was stirred at −78° C. for 2 h and left to warm to room temperature over 2 h. Water (1 mL) was added and the mixture was poured onto an isolute HM-N SPE cartridge and eluted with ethyl acetate (10 mL). The eluant was evaporated under reduced pressure and the crude material was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to afford the title compound (0.071 g, 53% yield) as a pale yellow oil: m/z 350.14 (MH$^+$); HPLC (50% to 80% gradient [95:5 MeOH:water, 10 mmol ammonium acetate] 220 nm XTERRA 2.0 ml/min) 6.21 min. (4R,9aR)-6-Ethylsulfanyl-4-methyl-1,2,3,4,9,9a-hexahydro-2-4a,5-triaza-fluorene A mixture of (4R,9aR)-6-ethylsulfanyl-4-methyl-3,4,9,9a-tetrahydro-1H-2,4a,5-triaza-fluorene-2-carboxylic acid tert-butyl ester (0.02 g, 0.057 mmol), DCM (2 mL) and TFA (2 mL) was shaken at room temperature for 2 h. The reaction mixture was evaporated under reduced pressure. The crude material was dissolved in methanol and transferred onto a SCX-2 ion exchange column (500 mg) and washed with methanol (10 mL), ammonia in methanol (2M, 3 mL) was added and the eluant collected and evaporated under reduced pressure to afford the title compound (0.014 g, 100% yield) as a pale yellow oil: m/z 250.25 (MH$^+$); HPLC (50% to 80% gradient [95:5 MeOH:water, 10 mmol ammonium acetate] 220 nm XTERRA 2.0 ml/min) 1.23 min.

Example 60

(4R,9aR)-6-Allylsulfanyl-4-methyl-1,2,3,4,9,9a-hexahydro-2-4a,5-triaza-fluorene (4R,9aR)-6-Allylsulfanyl-4-methyl-3,4,9,9a-tetrahydro-1H-2,4a,5-triaza-fluorene-2-carboxylic acid tert-butyl ester This was prepared according to the method described in Example 59 using allyl disulfide to produce 0.0578 g (30% yield) of the product as a pale yellow oil: m/z 462.16 (MH$^+$); HPLC (50% to 80% gradient [95:5 MeOH:water, 10 mmol ammonium acetate] 220 nm XTERRA 2.0 ml/min) 6.45 min.

(4R,9aR)-6-Allylsulfanyl-4-methyl-1,2,3,4,9,9a-hexahydro-2,4a,5-triaza-fluorene

This was prepared according to the method described in Example 59 using (4R,9aR)-6-allylsulfanyl-4-methyl-3,4,9,9a-tetrahydro-1H-2,4a,5-triaza-fluorene-2-carboxylic acid tert-butyl ester to produce 0.014 g of the product as a pale yellow oil: m/z 262.19 (MH$^+$); HPLC (50% to 80% gradient [95:5 MeOH:water, 10 mmol ammonium acetate] 220 nm XTERRA 2.0 ml/min) 1.49 min.

Example 61

(4R,9aR)-6-Propylsulfanyl-4-methyl-1,2,3,4,9,9a-hexahydro-2-4a,5-triaza-fluorene (4R,9aR)-4-Methyl-6-propylsulfanyl-3,4,9,9a-tetrahydro-1H-2,4a,5-triaza-fluorene-2-carboxylic acid tert-butyl ester This was prepared according to the method described in Example 59 using propyl disulfide to produce 0.053 g (27% yield) of the product as a pale yellow oil: m/z 364.24 (MH$^{30}$); HPLC (50% to 80% gradient [95:5 MeOH:water, 10 mmol ammonium acetate] 220 nm XTERRA 2.0 ml/min) 6.94 min.

(4R,9aR)-6-Propylsulfanyl-4-methyl-1,2,3,4,9,9a-hexahydro-2,4a,5-triaza-fluorene This was prepared according to the method described in Example 59 from (4R,9aR)-4-methyl-6-propylsulfanyl-3,4,9,9a-tetrahydro-1H-2,4a,5-triaza-fluorene-2-carboxylic acid tert-butyl ester to produce 0.015 g of the product as a pale yellow oil: m/z 264.24 (MH$^+$); HPLC (50% to 80% gradient [95:5 MeOH:water, 10 mmol ammonium acetate] 220 nm XTERRA 2.0 ml/min) 2.02 min.

Example 62

(4R,9aR)-6-Isopropylsulfanyl-4-methyl-1,2,3,4,9,9a-hexahydro-2-4a,5-triaza-fluorene (4R,9aR)-6-Isopropylsulfanyl-4-methyl-3,4,9,9a-tetrahydro-1H-2,4a,5-triaza-fluorene-2-carboxylic acid tert-butyl ester This was prepared according to the method described in Example 59 using isopropyl disulfide to produce 0.051 g (26% yield) of the product as a pale yellow oil: m/z 364.31 (MH$^+$); NMR $\delta_H$ (400 MHz, CDCl$_3$) 1.25 (3H, d, J 7.0 Hz), 1.36 (6H, d, J 6.5 Hz), 1.48 (9H, s), 2.55 (1H, dd, J 16.5 and 6.0 Hz), 3.02–3.11 (4H, m), 3.84–4.02 (4H, m), 6.36 (1H, d, J 7.0 Hz) and 7.0 (1H, d, J 7.0 Hz).

(4R,9aR)-6-Isopropylsulfanyl-4-methyl-1,2,3,4,9,9a-hexahydro-2,4a,5-triaza-fluorene This was prepared according to the method described in Example 59 using (4R,9aR)-6-isopropylsulfanyl-4-methyl-3,4,9,9a-tetrahydro-1H-2,4a,5-triaza-fluorene-2-carboxylic acid tert-butyl ester to produce 0.0146 g of the product as a pale yellow oil: m/z 264.3 (MH$^+$); NMR $\delta_H$ (400 MHz, CDCl$_3$) 1.37 (3H, d, J 7.0 Hz), 1.39 (6H, d, J 7.0 Hz), 2.55 (1H, dd, J 16.0 and 5.5 Hz), 2.69–3.15 (5H, m), 4.06–4.13 (1H, m), 4.46–4.50 (2H, m), 5.31 (1H, br s), 6.40 (1H, d, J 7.5 Hz) and 7.04 (1H, d, J 7.0 Hz).

Example 63

(4R,9aR)-6-(1-(RS)-Methoxy-propyl)-4-methyl-1,2,3,4,9,9a-hexahydro-2,4a,5-triaza-fluorene To a solution of (4R,9aR)-6-(1-hydroxy-propyl)-4-methyl-3,4,9,9a-tetrahydro-1H-2,4a,5-triaza-fluorene-2-carboxylic acid tert-butyl ester (52 mg) in DMF (1 ml) was added NaH (12 mg) under argon. The mixture was shaken at room temperature for 25 minutes, methyl iodide (19 µl) was added and the mixture was shaken for a further 24 hours. The mixture was partitioned between CH$_2$Cl$_2$ and aqueous NH$_4$Cl, the phases were separated and the dried organic layer was concentrated in vacuo. The residue was purified by preparatory HPLC (Prep Nova-Pak HR C18 6 µm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min). The purified product was deprotected according to the procedure described for Example 56 to afford (4R,9aR)-6-(1-(RS)-methoxy-propyl)-4-methyl-1,2,3,4,9,9a-hexahydro-2,4a,5-triaza-fluorene di-trifluoroacetate as a colorless oil (53 mg): HPLC [Xterra; 50/80; 255 nm] 100%, 0.74 min; MS (ES) 262.1 (MH$^+$).

Example 64

(4R,9aR)-6-(1-(RS)-Cyclopropylmethoxy-propyl)-4-methyl-1,2,3,4,9,9a-hexahydro-2,4a,5-triaza-fluorene (4R,9aR)-6-(1-(RS)-Cyclopropylmethoxy-propyl)-4-methyl-1,2,3,4,9,9a-hexahydro-2,4a,5-triaza-fluorene di-trifluoroacetate (32 mg) was made from 6-(1-hydroxy-propyl)-4-methyl-3,4,9,9a-tetrahydro-1H-2,4a,5-triaza-fluorene-2-carboxylic acid tert-butyl ester (52 mg), using cyclopropylmethyl bromide (29 µl) in place of methyl iodide, according to the procedures described in Example 63 to afford the product as a colorless oil. HPLC [Xterra; 50/80; 255 nm] 100%, 1.44 min; MS (ES) 302.1 (MH$^+$).

Example 65

(4R,9aR)-6-(1-(RS)-Methoxy-butyl)-4-methyl-1,2,3,4,9,9a-hexahydro-2,4a,5-triaza-fluorene (4R,9aR)-6-(1-(RS)-Methoxy-butyl)-4-methyl-1,2,3,4,9,9a-hexahydro-2,4a,5-triaza-fluorene di-trifluoroacetate (69 mg) was made from 6-(1-hydroxy-butyl)-4-methyl-3,4,9,9a-tetrahydro-1H-2,4a,5-triaza-fluorene-2-carboxylic acid tert-butyl ester (54 mg), according to the procedure described in Example 63 to afford the product as a colorless oil: HPLC [Xterra; 50/80; 255 nm] 99.8%, 1.05 min; MS (ES) 276.0 (MH$^+$).

Example 66

(4R,9aR)-6-(1-(RS)-Ethoxy-butyl)-4-methyl-1,2,3,4,9,9a-hexahydro-2,4a,5-triaza-fluorene (4R,9aR)-6-(1-(RS)-Ethoxy-butyl)-4-methyl-1,2,3,4,9,9a-hexahydro-2,4a,5-triaza-fluorene di-trifluoroacetate (41 mg) was made from 6-(1-hydroxy-butyl)-4-methyl-3,4,9,9a-tetrahydro-1H-2,4a,5-triaza-fluorene-2-carboxylic acid tert-butyl ester (54 mg), using ethyl iodide (21 µl) in place of methyl iodide, according to the procedures described in Example 63 to afford the product as a yellow oil: HPLC [Xterra; 50/80; 255 nm] 99.8%, 1.46 min; MS (ES) 290.3 (MH$^+$).

Example 67

(4R,9aR)-6-(1-(RS)-Cyclopropylmethoxy-butyl)-4-methyl-1,2,3,4,9,9a-hexahydro-2,4a,5-triaza-fluorene (4R,9aR)-6-(1-(RS)-Cyclopropylmethoxy-butyl)-4-methyl-1,2,3,4,9,9a-hexahydro-2,4a,5-triaza-fluorene di-trifluoroacetate (53 mg) was made from 6-(1-hydroxy-butyl)-4-methyl-3,4,9,9a-tetrahydro-1H-2,4a,5-triaza-fluorene-2-carboxylic acid tert-butyl ester (54 mg), using cyclopropylmethyl bromide (29 µl) in place of methyl iodide, according to the procedure described in Example 63 to afford the product as a colorless oil: HPLC [Xterra; 50/80; 255 nm] 99.6%, 2.29 min; MS (ES) 316.4 (MH$^+$).

Example 68

(4R,9aR)-Isopropyl-carbamic acid 4-methyl-1,2,3,4,9,9a-hexahydro-2-4a,5-triaza-fluorene-6-ylmethyl-ester (4R,9aR)-6-Isopropylcarbamoyloxymethyl-4-methyl-3,4,9,9a-tetrahydro-1H-2,4a,5-triaza-fluorene-2-carboxylic acid tert-butyl ester A solution of (4R,9aR)-6-hydroxymethyl-4-methyl-3,4,9,9a-tetrahydro-1H-2,4a,5-triaza-fluorene-2-carboxylic acid tert-butyl ester (Example 15, intermediate b) (0.01 g, 0.03 mmol) and DCM (1 mL) was added to PS-BEMP (2.2 mmol/g, 0.03 g, 0.06 mmol). The mixture was shaken at room temperature for 5 min, isopropyl isocyanate (17 µL, 0.15 mmol) was added, the mixture was heated at 40° C. and left to shake for 24 h. PS-Trisamine (4.7 mmol/g, 0.06 g, 0.3 mmol) and DCM (1 mL) were added and the reaction mixture was left to shake at room temperature for 4 h. The reaction mixture was filtered and the solid washed with DCM (3 mL). The filtrate was evaporated and the crude product purified by reverse phase preparative HPLC (Prep Nova-Pak HR C18 6 µm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to afford the title compound (0.053 g, 44% yield) as a pale yellow oil: m/z 405.29 (MH$^+$); NMR $\delta_H$ (400 MHz, CDCl$_3$) 1.15 (6H, d, J 6.5 Hz), 1.24 (3H, d, J 6.5 Hz), 1.47 (9H, s) 2.50–2.60 (2H, m), 3.0–3.1 (2H, m), 3.8–3.9 (1H, m), 3.9–4.1 (2H, m), 4.5–4.6 (2H, m), 4.7–4.8 (1H, br s), 5.04 (2H, s), 6.50 (1H, d, J 7.0 Hz) and 7.18 (1H, d, J 7.0 Hz).

(4R,9aR)-Isopropyl-carbamic acid 4-methyl-1,2,3,4,9,9a-hexahydro-2-4a,5-triaza-fluorene-6-ylmethyl-ester This was prepared according to the method described in Example 59 using (4R,9aR)-6-isopropylcarbamoyloxymethyl-4-methyl-3,4,9,9a-tetrahydro-1H-2,4a,5-triaza-fluorene-2-carboxylic acid tert-butyl ester to produce 0.003 g of the product as a pale yellow oil: m/z 305.33 (MH$^+$); NMR $\delta_H$ (400 MHz, CDCl$_3$) 1.15 (6H, d, J 6.5 Hz), 1.33 (3H, d, J 7.0 Hz), 2.46 (1H, dd, J 16.0 and 6.5 Hz), 2.62 (1H, t, J 11.5 Hz), 2.84 (1H, d, J 12.0 Hz), 2.95–3.01 (2H, m), 3.05 (1H, dd, J 12.0 and 3.5 Hz), 3.79–3.88 (1H, m), 3.95–4.02 (1H, m), 4.35–4.39 (1H, m), 4.59 (1H, br s), 4.98 (2H, s), 6.44 (1H, d, J 7.0 Hz) and 7.11 (1H, d, J 7.0 Hz) (note NH unobserved).

Example 69

(4R,9aR)-tert-Butyl-carbamic acid 4-methyl-1,2,3,4,9,9a-hexahydro-2,4a,5-triaza-fluoren-6-ylmethyl ester (4R,9aR)-6-tert-Butylcarbamoyloxymethyl-4-methyl-3,4,9,9a-tetrahydro-1H-2,4a,5-triaza-fluorene-2-carboxylic acid tert-butyl ester This was prepared according to the method described in Example 68 using tert-butyl isocyanate to produce 0.0061 g (49% yield) of the product as a pale yellow oil: m/z 419.28 (MH$^+$); NMR $\delta_H$ (400 MHz, CDCl$_3$) 1.24 (3H, d, J 7.0 Hz), 1.32 (9H, s), 1.47 (9H, s), 2.52–2.57 (4H, m), 3.01–3.08 (2H, m), 3.99–4.05 (2H, m), 4.50 (1H, br s), 4.98 (2H, s), 6.47 (1H, d, J 7.0 Hz) and 7.17 (1H, d, J 7.0 Hz).

(4R,9aR)-tert-Butyl-carbamic acid 4-methyl-1,2,3,4,9,9a-hexahydro-2,4a,5-triaza-fluoren-6-ylmethyl ester This was prepared according to the method described in Example 59 using (4R,9aR)-6-tert-butylcarbamoyloxymethyl-4-methyl-3,4,9,9a-tetrahydro-1H-2,4a,5-triaza-fluorene-2-carboxylic acid tert-butyl ester to produce 0.003 g of the product as a pale yellow oil: m/z 319.32 (MH$^+$); NMR $\delta_H$ (400 MHz, CDCl$_3$) 3.31 (3H, d, J 7.0 Hz), 3.32 (9H, s), 2.45 (1H, dd, J 16.0 and 6.0 Hz), 2.61 (1H, t, J 12.0 Hz), 2.80 (1H, d, J 12.0 Hz), 2.94 (1H, m), 3.01 (1H, dd, J 11.5 and 3.5 Hz), 3.91–3.98 (2H, m), 4.34–4.36 (2H, m), 4.74 (1H, br s), 4.94 (2H, s), 6.41 (1H, d, J 7.0 Hz) and 7.1 (1H, d, J 7.0 Hz).

Example 70

Cyclohexyl-carbamic acid 4-methyl-1,2,3,4,9,9a-hexahydro-2,4a,5-triaza-fluoren-6-ylmethyl ester (4R,9aR)-6-Cyclohexylcarbamoyloxymethyl-4-methyl-3,4,9,9a-tetrahydro-1H-2,4a,5-triaza-fluorene-2-carboxylic acid tert-butyl ester This was prepared according to the method described in Example 68 using cyclohexylisocyanate to produce 0.0058 g (44% yield) of the product as a pale yellow oil: m/z 445.28 (MH$^+$); NMR $\delta_H$ (400 MHz, CDCl$_3$) 1.08 (6H, d, J 6.5 Hz), 1.23 (3H, d, J 7.0 Hz), 1.28 (6H, d, J 7.5 Hz), 1.44 (9H, s), 2.60 (2H, m), 3.0–3.16 (2H, m), 3.84–4.0 (2H, m), 4.44–4.96 (1H, m), 5.18 (2H, s), 6.48 (1H, d, J 7.0 Hz), 7.24 (1H, d, J 7.0 Hz) and 8.25 (1H, br s).

Cyclohexyl-carbamic acid 4-methyl-1,2,3,4,9,9a-hexahydro-2,4a,5-triaza-fluoren-6-ylmethyl ester This was prepared according to the method described in Example 59 using (4R,9aR)-6-cyclohexylcarbamoyloxymethyl-4-methyl-3,4,9,9a-tetrahydro-1H-2,4a,5-triaza-fluorene-2-carboxylic acid tert-butyl ester to produce 0.003 g of the product as a pale yellow oil: m/z 345.31 (MH$^+$); NMR $\delta_H$ (400 MHz, CDCl$_3$) 1.1–1.21 (6H, m), 1.31 (3H, d, J 7.0 Hz), 1.56–1.61 (4H, m), 1.66–1.72 (2H, m), 1.91–1.96 (4H, m), 2.45 (1H, dd, J 16.0 and 6.5 Hz), 2.60 (1H, t, J 11.0 Hz), 2.78 (1H, d, J 12.5 Hz), 2.93–2.97 (1H, m), 3.01 (1H, dd, J 12.0 and 3.5 Hz), 3.49–3.54 (1H, m), 3.91–3.98 (1H, m), 4.31–4.37 (1H, m), 4.68 (1H, br s), 4.98 (2H, s), 6.42 (1H, d, J 7.0 Hz) and 7.10 (1H, d, J 7.0 Hz).

Example 71

(4R,9aR)-Ethyl-carbamic acid 4-methyl-1,2,3,4,9,9a-hexahydro-2,4a,5-triaza-fluoren-6-ylmethyl ester (4R,9aR)-6-Ethylcarbamoyloxymethyl-4-methyl-3,4,9,9a-tetrahydro-1H-2,4a,5-triaza-fluorene-2-carboxylic acid tert-butyl ester Ethyl isocyanate (22 mL, 0.31 mmol) was added to a mixture of DMAP (0.008 g, 0.063 mmol) (4R,9aR)-6-hydroxymethyl-4-methyl-3,4,9,9a-tetrahydro-1H-2,4a,5-triaza-fluorene-2-carboxylic acid tert-butyl ester (Example 15, intermediate b) (0.02 g, 0.063 mmol), 4 Å molecular sieves (0.02 g, crushed) and DCM (2 mL). The reaction vessel was sealed and heated at 140° C. in a CEM Discoverer™ microwave for 15 min. The reaction mixture was cooled to room temperature, DCM (2 mL) and AP-trisamine (2.49 mmol/g, 0.25 g, 0.63 mmol) were added, the reaction vessel was sealed and heated at 130° C. in a CEM Discoverer™ microwave for 5 min. The reaction mixture was filtered and the solid washed with DCM (4 mL) the filtrate was evaporated and the crude product purified by reverse phase preparative HPLC (Prep Nova-Pak HR C18 6 μm 60 Å 30 mm×300 mm column, UV detection 254 nm, mobile phase 95:5 methanol:water and 10 mmol ammonium acetate, gradient 50 methanol to 100% 0 to 10 min then 100% methanol to 13 min, 20 mL/min) to afford the title compound (0.053 g, 22% yield) as a pale yellow oil: m/z 391.28 (MH$^+$); HPLC (50% to 80% gradient [95:5 MeOH:water, 10 mmol ammonium acetate] 255 nm XTERRA 2.0 ml/min) 2.98 min, 99%.

(4R,9aR)-Ethyl-carbamic acid 4-methyl-1,2,3,4,9,9a-hexahydro-2,4a,5-triaza-fluoren-6-ylmethyl ester This was prepared according to the method described in Example 59 using (4R,9aR)-6-ethylcarbamoyloxymethyl-4-methyl-3,4,9,9a-tetrahydro-H-2,4a,5-triaza-fluorene-2-carboxylic acid tert-butyl ester to produce 0.0011 g of the product as a pale yellow oil: m/z 291.28 (MH$^+$); HPLC (50% to 80% gradient [95:5 MeOH:water, 10 mmol ammonium acetate] 255 nm XTERRA 2.0 ml/min) 0.55 min, 98.3%.

Example 72

(4R,9aR)-Phenyl-carbamic acid 4-methyl-1,2,3,4,9,9a-hexahydro-2,4a,5-triaza-fluoren-6-ylmethyl ester (4R,9aR)-4-Methyl-6-phenylcarbamoyloxymethyl-3,4,9,9a-tetrahydro-1H-2,4a,5-triaza-fluorene-2-carboxylic acid tert-butyl ester This was prepared according to the method described in Example 71 using phenylisocyanate to afford 0.0106 g (38% yield) of the product as a pale yellow oil: m/z 439.28 (MH$^+$); HPLC (50% to 80% gradient [95:5 MeOH:water, 10 mmol ammonium acetate] 255 nm XTERRA 2.0 ml/min) 5.76 min, 82%.

(4R,9aR)-Phenyl-carbamic acid 4-methyl-1,2,3,4,9,9a-hexahydro-2,4a,5-triaza-fluoren-6-ylmethyl ester This was prepared according to the method described in Example 59 using (4R,9aR)-4-methyl-6-phenylcarbamoyloxymethyl-3,4,9,9a-tetrahydro-1H-2,4a,5-triaza-fluorene-2-carboxylic acid tert-butyl ester to produce 0.0023 g of the pale yellow oil: m/z 339.11 (MH$^+$); HPLC (50% to 80% gradient [95:5 MeOH:water, 10 mmol ammonium acetate] 255 nm XTERRA 2.0 ml/min) 1.33 min, 99.2%.

Example 73

(4R,9aR)-Benzyl-carbamic acid 4-methyl-1,2,3,4,9,9a-hexahydro-2,4a,5-triaza-fluoren-6-ylmethyl ester (4R,9aR)-6-Benzylcarbamoyloxymethyl-4-methyl-3,4,9,9a-tetrahydro-1H-2,4a,5-triaza-fluorene-2-carboxylic acid tert-butyl ester This was prepared according to the method described in Example 71 using benzylisocyanate to produce 0.008 g (29% yield) of the product as a pale yellow oil: m/z 453.08 (MH$^+$); HPLC (50% to 80% gradient [95:5 MeOH:water, 10 mmol ammonium acetate] 255 nm XTERRA 2.0 ml/min) 5.28 min, 98.7%.

(4R,9aR)-Benzyl-carbamic acid 4-methyl-1,2,3,4,9,9a-hexahydro-2,4a,5-triaza-fluoren-6-ylmethyl ester This was prepared according to the method described in Example 59 using (4R,9aR)-6-benzylcarbamoyloxymethyl-4-methyl-3,4,9,9a-tetrahydro-1H-2,4a,5-triaza-fluorene-2-carboxylic acid tert-butyl ester to produce 0.0023 g of the product as a pale yellow oil: m/z 353.30 (MH$^+$); HPLC (50% to 80% gradient [95:5 MeOH:water, 10 mmol ammonium acetate] 255 nm XTERRA 2.0 ml/min) 1.10 min, 99.8%.

Example 74

(4R,9aR)-Allyl-carbamic acid 4-methyl-1,2,3,4,9,
9a-hexahydro-2,4a,5-triaza-fluoren-6-ylmethyl ester (4R,9aR)-6-Allylcarbamoyloxymethyl-4-methyl-3,4,
9,9a-tetrahydro-1H-2,4a,5-triaza-fluorene-2-carboxylic acid tert-butyl ester This was prepared according to the method described in Example 71 using allylisocyanate to produce 0.0094 g (37% yield) of the product as a pale yellow oil: m/z 403.04 (MH$^+$); HPLC (50% to 80% gradient [95:5 MeOH:water, 10 mmol ammonium acetate] 255 nm XTERRA 2.0 ml/min) 3.51 min, 98%.

(4R,9aR)-Allyl-carbamic acid 4-methyl-1,2,3,4,9,
9a-hexahydro-2,4a,5-triaza-fluoren-6-ylmethyl ester This was prepared according to the method described in Example 59 using (4R,9aR)-6-allylcarbamoyloxymethyl-4-methyl-3,4,9,9a-tetrahydro-1H-2,4a,5-triaza-fluorene-2-carboxylic acid tert-butyl ester to produce 0.0012 g of the product as a pale yellow oil: m/z 303.09 (MH$^+$); HPLC (50% to 80% gradient [95:5 MeOH:water, 10 mmol ammonium acetate] 255 nm XTERRA 2.0 ml/min) 0.60 min, 96.3%.

Example 75

(4R,9aR)-Ethyl-carbamic acid 1-(RS)-(4-methyl-1,
2,3,4,9,9a-hexahydro-2,4a,5-triaza-fluoren-6-yl)-propyl ester To a solution of (4R,9aR)-6-(1-hydroxy-propyl)-4-methyl-3,4,9,9a-tetrahydro-1H-2,4a,5-triaza-fluorene-2-carboxylic acid tert-butyl ester (52 mg) in THF (1 ml) was added NaH (12 mg). The mixture was shaken for 5 mins, ethylisocyanate was added and the mixture shaken for 18 hours. The mixture was partitioned between $CH_2Cl_2$ and aqueous ammonium chloride, the phases were separated and the organics were concentrated in vacuo. The residue was purified by preparatory HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min). The purified product was deprotected according to the method described for Example 56 to afford (4R,9aR)-ethyl-carbamic acid 1-(RS)-(4-methyl-1,2,3,4,9,9a-hexahydro-2,4a,5-triaza-fluoren-6-yl)-propyl ester di-trifluoroacetate (59 mg) as a colorless oil: HPLC [Xterra; 50/80; 255 nm] 100%, 0.78 min; MS (ES) 319.2 (MH$^+$).

Example 76

(4R,9aR)-Ethyl-carbamic acid 1-(RS)-(4-methyl-1,
23,4,9,9a-hexahydro-2,4a,5-triaza-fluoren-6-yl)-butyl ester (4R,9aR)-Ethyl-carbamic acid 1-(RS)-(4-methyl-1,2,3,4,9,9a-hexahydro-2,4a,5-triaza-fluoren-6-yl)-butyl ester di-trifluoroacetate (50 mg) was made from 6-(1-hydroxy-butyl)-4-methyl-3,4,9,9a-tetrahydro-1H-2,4a,5-triaza-fluorene-2-carboxylic acid tert-butyl ester (54 mg), according to the procedure described in Example 75 to afford the product as a colorless oil: HPLC [Xterra; 50/80; 255 nm] 100%, 1.09 min; MS (ES) 333.3 (MH$^+$).

Example 77

(4R,9aR)-Ethyl-carbamic acid 1-(S)-(4-methyl-1,2,
3,4,9,9a-hexahydro-2,4a,5-triaza-fluoren-6-yl)-ethyl ester (4R,9aR)-Ethyl-carbamic acid 1-(S)-(4-methyl-1,2,
3,4,9,9a-hexahydro-2,4a,5-triaza-fluoren-6-yl)-ethyl ester di-trifluoroacetate (4R,9aR)-Ethyl-carbamic acid 1-(S)-(4-methyl-1,2,3,4,9,9a-hexahydro-2,4a,5-triaza-fluoren-6-yl)-ethyl ester di-trifluoroacetate (50 mg) was made from 6-(1S)-(1-hydroxy-ethyl)-(4R,9aR)-4-methyl-3,4,9,9a-tetrahydro-1H-2,4a,5-triaza-fluorene-2-carboxylic acid tert-butyl ester (40 mg) according to the procedure described in Example 75 to afford the product as a colorless oil: HPLC [Xterra; 20/50; 250 nm] 99.5%, 1.90 min; MS (ES) 304.0 (MH$^+$).

Example 78

(4R,9aR)-Propyl-carbamic acid 1-(S)-(4-methyl-1,2,
3,4,9,9a-hexahydro-2,4a,5-triaza-fluoren-6-yl)-ethyl ester di-trifluoroacetate (4R,9aR)-Propyl-carbamic acid 1-(S)-(4-methyl-1,2,3,4,9,9a-hexahydro-2,4a,5-triaza-fluoren-6-yl)-ethyl ester di-trifluoroacetate (55 mg) was made from 6-((1S)-1-hydroxy-ethyl)-(4R,9aR)-4-methyl-3,4,9,9a-tetrahydro-1H-2,4a,5-triaza-fluorene-2-carboxylic acid tert-butyl ester (40 mg), using propylisocyanate (22 μl) in place of ethylisocyanate, according to the procedure described in Example 75 to afford the product as a colorless oil. HPLC [Xterra; 20/50; 250 nm] 99.9%, 3.45 min; MS (ES) 318.0 (MH$^+$).

Example 79

(4R,9aR)-Isopropyl-carbamic acid 1-(S)-(4-methyl-1,2,3,4,9,9a-hexahydro-2,4a,5-triaza-fluoren-6-yl)-ethyl ester di-trifluoroacetate (4R,9aR)-Isopropyl-carbamic acid 1-(S)-(4-methyl-1,2,3,4,9,9a-hexahydro-2,4a,5-triaza-fluoren-6-yl)-ethyl ester di-trifluoroacetate (58 mg) was made from 6-(1S)-(1-hydroxy-ethyl)-(4R,9aR)-4-methyl-3,4,9,9a-tetrahydro-1H-2,4a,5-triaza-fluorene-2-carboxylic acid tert-butyl ester (40 mg), using isopropylisocyanate (24 μl) in place of ethylisocyanate, according to the procedure described in Example 75 to afford the product as a colorless oil. HPLC [Xterra; 20/50; 255 nm] 100%, 3.17 min; MS (ES) 318.4 (MH$^+$).

Example 80

(4R,9aR)-Pyrrolidine-1-carboxylic acid 4-methyl-1,
2,3,4,9,9a-hexahydro-2,4a,5-triaza-fluoren-6-ylmethyl ester (4R,9aR)-4-Methyl-6-(pyrrolidine-1-carbonyloxymethyl)-3,4,9,9a-tetrahydro-1H-2,4a,5-triaza-fluorene-2-carboxylic acid tert-butyl ester A mixture of 6-hydroxymethyl-4-methyl-3,4,9,9a-tetrahydro-1H-2,4a,5-triaza-fluorene-2-carboxylic acid tert-butyl ester (0.02 g, 0.063 mmol) and DCM (1 mL) was cooled to 0° C. and carbonyl diimidazole (0.010 g, 0.063 mmol) was added, the mixture was stirred at 0° C. for 2 h and stirred at room temperature for 3 h. A mixture of pyrrolidine (10 mL, 0.13 mmol) and DCM (1 mL) was added and the reaction mixture was sealed and shaken at 60° C. for 48 h. The reaction mixture was cooled and water (2 mL) added, the mixture was shaken at room temperature for 1 h then filtered through a PTFE frit. The filtrate was evaporated and the crude product purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min) to afford the title compound (0.16 g, 61% yield) as a pale yellow oil: m/z 417.07 (MH$^+$); HPLC (50% to 80% gradient [95:5 MeOH:water, 10 mmol ammonium acetate] 255 nm XTERRA 2.0 ml/min) 4.20 min, 99.3%.

(4R,9aR)-Pyrrolidine-1-carboxylic acid 4-methyl-1,2,3,4,9,9a-hexahydro-2,4a,5-triaza-fluoren-6-ylmethyl ester This was prepared according to the method described in Example 59 using (4R,9aR)-4-methyl-6-(pyrrolidine-1-carbonyloxymethyl)-3,4,9,9a-tetrahydro-1H-2,4a,5-triaza-fluorene-2-carboxylic acid tert-butyl ester to produce 0.0018 g of the product as a pale yellow oil: m/z 317.21 (MH$^+$); HPLC (50% to 80% gradient [95:5 MeOH:water, 10 mmol ammonium acetate] 255 nm XTERRA 2.0 ml/min) 0.76 min, 100%.

Example 81

(4R,9aR)-Piperazine-1,4-dicarboxylic acid benzyl ester 4-methyl-1,2,3,4,9,9a-hexahydro-2,4a,5-triaza-fluoren-6-ylmethyl ester (4R,9aR)-Piperazine-1,4-dicarboxylic acid benzyl ester 2-tert-butoxycarbonyl-4-methyl-1,2,3,4,9,9a-hexahydro-2,4a,5-triaza-fluoren-6-ylmethyl ester This was prepared according to the method described in Example 80 using piperazine-1-carboxylic acid benzyl ester to produce 0.0143g (40% yield) of the product as a pale yellow oil: m/z 566.30 (MH$^+$); HPLC (50% to 80% gradient [95:5 MeOH:water, 10 mmol ammonium acetate] 255 nm XTERRA 2.0 ml/min) 6.03 min, 99.6%.

(4R,9aR)-Piperazine-1,4-dicarboxylic acid benzyl ester 4-methyl-1,2,3,4,9,9a-hexahydro-2,4a,5-triaza-fluoren-6-ylmethyl ester This was prepared according to the method described in Example 59 using (4R,9aR)-piperazine-1,4-dicarboxylic acid benzyl ester 2-tert-butoxycarbonyl-4-methyl-1,2,3,4,9,9a-hexahydro-2,4a,5-triaza-fluoren-6-ylmethyl ester to produce 0.0035g (31% yield) of the product as a pale yellow oil: m/z 466.26 (MH$^+$); HPLC (50% to 80% gradient [95:5 MeOH:water, 10 mmol ammonium acetate] 255 nm XTERRA 2.0 ml/min) 1.93 min, 95.6%.

Example A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions can have the following composition:

| | |
|---|---|
| Compound of formula I | 3.0 mg |
| Gelatin | 150.0 mg |
| Phenol | 4.7 mg |
| Water for injection solutions | ad 1.0 ml |

What is claimed is:
1. A compound of formula (I)

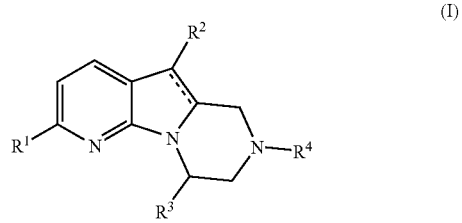

(I)

wherein

R$^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino, haloalkyl, hydroxyalkoxy, alkoxyalkoxy, hydroxyalkoxyalkyl, alkylcarbonyl, haloalkylcarbonyl, alkyl-S—, alkenyl-S—, A$^1$ or A$^2$;

R$^2$ is hydrogen, alkyl or alkoxy;

R$^3$ is alkyl, hydroxyalkyl or alkoxyalkyl;

R$^4$ is hydrogen or alkyl;

A$^1$ is

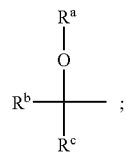

R$^a$ is hydrogen, alkyl, cycloalkyl or cycloalkylalkyl;

R$^b$ is hydrogen or alkyl; or R$^a$ and R$^b$ together with the oxygen atom and the carbon atom to which they are attached form tetrahydrofuranyl;

$R^C$ is haloalkyl, alkyl, alkoxyalkyl or thiazolyl;

$A^2$ is

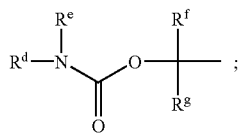

$R^d$ is alkyl, cycloalkyl, aryl, aralkyl or alkenyl;

$R^e$ is hydrogen or alkyl; or $R^d$ and $R^e$ together with the nitrogen atom to which they are attached form pyrrolidinyl or benzyloxycarbonylpiperazinyl;

$R^f$ is hydrogen or alkyl;

$R^g$ is hydrogen or alkyl;

or the pharmaceutically acceptable salts and esters of said compound.

2. The compound of claim 1, wherein $R^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino or haloalkyl.

3. The compound of claim 2, wherein $R^2$ is hydrogen.

4. The compound of claim 2, wherein $R^2$ is methyl.

5. The compound of claim 4, wherein $R^3$ is methyl.

6. The compound of claim 5, wherein $R^4$ is hydrogen.

7. The compound of claim 2, wherein $R^1$ is hydrogen, halogen, alkyl, cycloalkyl, alkoxycarbonylalkenyl, alkoxyalkyl, cyano, cycloalkylalkoxyalkyl, alkoxyalkoxyalkyl, amino or haloalkyl.

8. The compound according to claim 7, wherein $R^1$ is hydrogen, chloro, bromo, methyl, ethyl, trifluoromethyl, cyclopropyl, ethoxycarbonylethenyl, methoxypropyl, cyano, cyclopropylmethoxymethyl, methoxyethoxymethyl, methoxymethyl or primary amino.

9. The compound of claim 8, wherein $R^1$ is fluoromethyl, difluoromethyl, hydroxy-ethyl, methoxyethyl, ethoxyethyl, cyclopropylmethoxy-ethyl or allyl-S—.

10. A compound of formula (Ia)

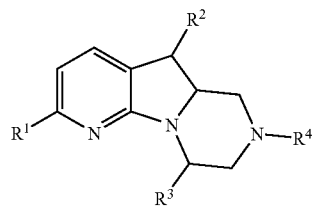

(Ia)

wherein $R^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino, haloalkyl, hydroxyalkoxy, alkoxyalkoxy, hydroxyalkoxyalkyl, alkylcarbonyl, haloalkylcarbonyl, alkyl-S—, alkenyl-S—, $A^1$ or $A^2$;

$R^2$ is hydrogen, alkyl or alkoxy;

$R^3$ is alkyl, hydroxyalkyl or alkoxyalkyl;

$R^4$ is hydrogen or alkyl;

$A^1$ is

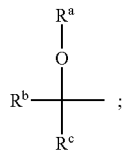

$R^a$ is hydrogen, alkyl, cycloalkyl or cycloalkylalkyl;

$R^b$ is hydrogen or alkyl; or $R^a$ and $R^b$ together with the oxygen atom and the carbon atom to which they are attached form tetrahydrofuranyl;

$R^C$ is haloalkyl, alkyl, alkoxyalkyl or thiazolyl;

$A^2$ is

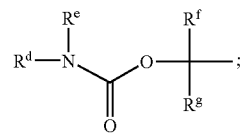

$R^d$ is alkyl, cycloalkyl, aryl, aralkyl or alkenyl;

$R^e$ is hydrogen or alkyl; or $R^d$ and $R^e$ together with the nitrogen atom to which they are attached form pyrrolidinyl or benzyloxycarbonylpiperazinyl;

$R^f$ is hydrogen or alkyl;

$R^g$ is hydrogen or alkyl;

or the pharmaceutically acceptable salts and esters of said compound.

11. A compound of formula (Ib)

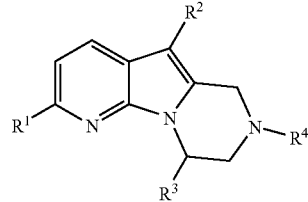

(Ib)

wherein $R^1$ is hydrogen, halogen, alkyl, cycloalkyl, alkenyl, alkoxycarbonylalkenyl, alkoxy, alkoxyalkyl, arylalkoxy, hydroxyalkyl, cyano, cycloalkylalkoxyalkyl, alkoxyalkoxyalkyl, arylalkoxyalkyl, amino, haloalkyl, hydroxyalkoxy, alkoxyalkoxy, hydroxyalkoxyalkyl, alkylcarbonyl, haloalkylcarbonyl, alkyl-S—, alkenyl-S—, $A^1$ or $A^2$;

$R^2$ is hydrogen, alkyl or alkoxy;

$R^3$ is alkyl, hydroxyalkyl or alkoxyalkyl;

$R^4$ is hydrogen or alkyl;

$A^1$ is

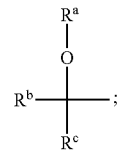

R$^a$ is hydrogen, alkyl, cycloalkyl or cycloalkylalkyl;
R$^b$ is hydrogen or alkyl; or R$^a$ and R$^b$ together with the oxygen atom and the carbon atom to which they are attached form tetrahydrofuranyl;
R$^C$ is haloalkyl, alkyl, alkoxyalkyl or thiazolyl;
A$^2$ is

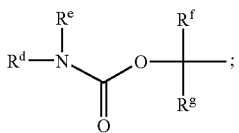

R$^d$ is alkyl, cycloalkyl, aryl, aralkyl or alkenyl;
R$^e$ is hydrogen or alkyl; or R$^d$ and R$^e$ together with the nitrogen atom to which they are attached form pyrrolidinyl or benzyloxycarbonylpiperazinyl;
R$^f$ is hydrogen or alkyl;
R$^g$ is hydrogen or alkyl;
or the pharmaceutically acceptable salts and esters of said compound.

12. A compound selected from the group
(R)-6-Chloro-4-methyl-1,2,3,4-tetrahydro-2,4a,5-triaza-fluorene;
(4R,9aR)-6-Chloro-4-methyl-1,2,3,4,9,9a-hexahydro-2,4a,5-triaza-fluorene;
(4R,9aS)-6-Chloro-4-methyl-1,2,3,4,9,9a-hexahydro-2,4a,5-triaza-fluorene;
(R)-6-Bromo-4-methyl-1,2,3,4-tetrahydro-2,4a,5-triaza-fluorene;
(4R,9aR)-6-Bromo-4-methyl-1,2,3,4,9,9a-hexahydro-2,4a,5-triaza-fluorene;
(4R,9aS)-6-Bromo-4-methyl-1,2,3,4,9,9a-hexahydro-2,4a,5-triaza-fluorene;
(R)-4,6-Dimethyl-1,2,3,4-tetrahydro-2,4a,5-triaza-fluorene;
(4R,9aR)-4,6-Dimethyl-1,2,3,4,9,9a-hexahydro-2,4a,5-triaza-fluorene;
(4R,9aR)-6-Ethyl-4-methyl-1,2,3,4,9,9a-hexahydro-2,4a,5-triaza-fluorene; and
(4R,9aR)-4-Methyl-6-trifluoromethyl-1,2,3,4,9,9a-hexahydro-2,4a,5-triaza-fluorene.

13. A compound selected from the group
(4R,9aR)-6-Cyclopropyl-4-methyl-1,2,3,4,9,9a-hexahydro-2,4a,5-triaza-fluorene;
(4R,9aR)-3-(4-Methyl-1,2,3,4,9,9a-hexahydro-2,4a,5-triaza-fluoren-6-yl)-acrylic acid ethyl ester;
(4R,9aR)-6-(3-Methoxy-propyl)-4-methyl-1,2,3,4,9,9a-hexahydro-2,4a,5-triaza-fluorene;
(4R,9aR)-4-Methyl-1,2,3,4,9,9a-hexahydro-2,4a,5-triaza-fluorene-6-carbonitrile;
(4R,9aR)-6-Cyclopropylmethoxymethyl-4-methyl-1,2,3,4,9,9a-hexahydro-2,4a,5-triaza-fluorene;
(4R,9aR)-6-(2-Methoxy-ethoxymethyl)-4-methyl-1,2,3,4,9,9a-hexahydro-2,4a,5-triaza-fluorene;
(4R,9aR)-6-Methoxymethyl-4-methyl-1,2,3,4,9,9a-hexahydro-2,4a,5-triaza-fluorene;
(R)-4-Methyl-1,2,3,4,9,9a-hexahydro-2,4a,5-triaza-fluorene;
(4R,9aR)-4-Methyl-1,2,3,4,9,9a-hexahydro-2,4a,5-triaza-fluoren-6-ylamine;
(R)-6-Chloro-4,9-dimethyl-1,2,3,4-tetrahydro-2,4a,5-triaza-fluorene; and
(4R,9aR)-6-Benzyloxy-4-methyl-1,2,3,4,9,9a-hexahydro-2,4a,5-triaza-fluorene.

14. A compound selected from the group
(4R,9aR)-6-Methoxy-4-methyl-1,2,3,4,9,9a-hexahydro-2,4a,5-triaza-fluorene;
(4R,9aR)-6-Ethoxy-4-methyl-1,2,3,4,9,9a-hexahydro-2,4a,5-triaza-fluorene;
(4R,9aR)-2-(4-Methyl-1,2,3,4,9,9a-hexahydro-2,4a,5-triaza-fluoren-6-yloxy)-ethanol;
(4R,9aR)-6-(2-Methoxy-ethoxy)-4-methyl-1,2,3,4,9,9a-hexahydro-2,4a,5-triaza-fluorene;
(4R,9aR)-6-Cyclobutylmethoxymethyl-4-methyl-1,2,3,4,9,9a-hexahydro-2,4a,5-triaza-fluorene;
(4R,9aR)-6-Ethoxymethyl-4-methyl-1,2,3,4,9,9a-hexahydro-2,4a,5-triaza-fluorene;
(4R,9aR)-6-Cyclohexylmethoxymethyl-4-methyl-1,2,3,4,9,9a-hexahydro-2,4a,5-triaza-fluorene;
(4R,9aR)-2-(4-Methyl-1,2,3,4,9,9a-hexahydro-2,4a,5-triaza-fluoren-6-ylmethoxy)-ethanol;
(4R,9aR)-(4-Methyl-1,2,3,4,9,9a-hexahydro-2,4a,5-triaza-fluoren-6-yl)-methanol;
(4R,9aR)-6-Isobutyl-4-methyl-1,2,3,4,9,9a-hexahydro-2,4a,5-triaza-fluorene; and
(4R,9aR)-6-Difluoromethyl-4-methyl-1,2,3,4,9,9a-hexahydro-2,4a,5-triaza-fluorene.

15. A compound selected from the group
(4R,9aR)-6-Fluoromethyl-4-methyl-1,2,3,4,9,9a-hexahydro-2,4a,5-triaza-fluorene;
(4R,9aR)-1-(4-Methyl-1,2,3,4,9,9a-hexahydro-2,4a,5-triaza-fluoren-6-yl)-ethanone;
(4R,9aR)-1-(4-Methyl-1,2,3,4,9,9a-hexahydro-2,4a,5-triaza-fluoren-6-yl)-propan-1-one;
(4R,9aR)-1-(4-Methyl-1,2,3,4,9,9a-hexahydro-2,4a,5-triaza-fluoren-6-yl)-butan-1-one;
(4R,9aR)-2,2,2-Trifluoro-1-(4-methyl-1,2,3,4,9,9a-hexahydro-2,4a,5-triaza-fluoren-6-yl)-ethanone;
(4R,9aR)-1-(RS)-(4-Methyl-1,2,3,4,9,9a-hexahydro-2,4a,5-triaza-fluoren-6-yl)-ethanol;
(4R,9aR)-6-(1-(R)-Hydroxy-ethyl)-4-methyl-3,4,9,9a-tetrahydro-1H-2,4a,5-triaza-fluorene;
(4R,9aR)-6-(1-(S)-Hydroxy-ethyl)-4-methyl-3,4,9,9a-tetrahydro-1H-2,4a,5-triaza-fluorene; and
(4R,9aR)-6-(1-(R)-Methoxy-ethyl)-4-methyl-1,2,3,4,9,9a-hexahydro-2,4a,5-triaza-fluorene.

16. A compound selected from the group
(4R,9aR)-6-(1-(S)-Methoxy-ethyl)-4-methyl-1,2,3,4,9,9a-hexahydro-2,4a,5-triaza-fluorene;
(4R,9aR)-6-(1-(R)-Ethoxy-ethyl)-4-methyl-1,2,3,4,9,9a-hexahydro-2,4a,5-triaza-fluorene;
(4R,9aR)-6-(1-(R)-Cyclopropylmethoxy-ethyl)-4-methyl-1,2,3,4,9,9a-hexahydro-2,4a,5-triaza-fluorene;
(4R,9aR)-6-(1-(S)-Ethoxy-ethyl)-4-methyl-1,2,3,4,9,9a-hexahydro-2,4a,5-triaza-fluorene;
(4R,9aR)-6-(1-(S)-Cyclopropylmethoxy-ethyl)-4-methyl-1,2,3,4,9,9a-hexahydro-2,4a,5-triaza-fluorene;
(4R,9aR)-3,3,3-Trifluoro-1-(4-methyl-1,2,3,4,9,9a-hexahydro-2,4a,5-triaza-fluoren-6-yl)-(R)-propan-1-ol;
(4R,9aR)-3,3,3-Trifluoro-1-(4-methyl-1,2,3,4,9,9a-hexahydro-2,4a,5-triaza-fluoren-6-yl)-(S)-propan-1-ol;
(4R,9aR)-(R)-(4-Methyl-1,2,3,4,9,9a-hexahydro-2,4a,5-triaza-fluoren-6-yl)-thiazol-2-yl-methanol;
(4R,9aR)-(S)-(4-Methyl-1,2,3,4,9,9a-hexahydro-2,4a,5-triaza-fluoren-6-yl)-thiazol-2-yl-methanol; and
(4R,9aR)-2-(4-Methyl-1,2,3,4,9,9a-hexahydro-2,4a,5-triaza-fluoren-6-yl)-propan-2-ol.

17. A compound selected from the group
(4R,9aR)-3-Methyl-2-(RS)-(4-methyl-1,2,3,4,9,9a-hexahydro-2,4a,5-triaza-fluoren-6-yl)-butan-2-ol;
(4R,9aR)-1-Methoxy-2-(RS)-(4-methyl-1,2,3,4,9,9a-hexahydro-2,4a,5-triaza-fluoren-6-yl)-propan-2-ol;
(4R,9aR)-5-Chloro-2-(RS)-(4-methyl-1,2,3,4,9,9a-hexahydro-2,4a,5-triaza-fluoren-6-yl)-pentan-2-ol;
(4R,9aR)4-Methyl-6-(2-(RS)-methyl-tetrahydro-furan-2-yl)-1,2,3,4,9,9a-hexahydro-2,4a,5-triaza-fluorene;

(4R,9aR)-6-((RS)-1-Fluoro-ethyl)-4-methyl-1,2,3,4,9,9a-hexahydro-2,4a,5-triaza-fluorene;
(4R,9aR)-6-((RS)-1-Fluoro-propyl)-4-methyl-1,2,3,4,9,9a-hexahydro-2,4a,5-triaza-fluorene;
(4R,9aR)-6-((RS)-1-Fluoro-butyl)-4-methyl-1,2,3,4,9,9a-hexahydro-2,4a,5-triaza-fluorene;
(4R,9aR)-6-Ethylsulfanyl-4-methyl-1,2,3,4,9,9a-hexahydro-2-4a,5-triaza-fluorene;
(4R,9aR)-6-Allylsulfanyl-4-methyl-1,2,3,4,9,9a-hexahydro-2-4a,5-triaza-fluorene;
(4R,9aR)-6-Propylsulfanyl-4-methyl-1,2,3,4,9,9a-hexahydro-2-4a,5-triaza-fluorene; and
(4R,9aR)-6-Isopropylsulfanyl-4-methyl-1,2,3,4,9,9a-hexahydro-2-4a,5-triaza-fluorene.

18. A compound selected from the group
(4R,9aR)-6-(1-(RS)-Methoxy-propyl)-4-methyl-1,2,3,4,9,9a-hexahydro-2,4a,5-triaza-fluorene;
(4R,9aR)-6-(1-(RS)-Cyclopropylmethoxy-propyl)-4-methyl-1,2,3,4,9,9a-hexahydro-2,4a,5-triaza-fluorene;
(4R,9aR)-6-(1-(RS)-Methoxy-butyl)-4-methyl-1,2,3,4,9,9a-hexahydro-2,4a,5-triaza-fluorene;
(4R,9aR)-6-(1-(RS)-Ethoxy-butyl)-4-methyl-1,2,3,4,9,9a-hexahydro-2,4a,5-triaza-fluorene;
(4R,9aR)-6-(1-(RS)-Cyclopropylmethoxy-butyl)-4-methyl-1,2,3,4,9,9a-hexahydro-2,4a,5-triaza-fluorene;
(4R,9aR)-Isopropyl-carbamic acid 4-methyl-1,2,3,4,9,9a-hexahydro-2-4a,5-triaza-fluorene-6-ylmethylester;
(4R,9aR)-tert-Butyl-carbamic acid 4-methyl-1,2,3,4,9,9a-hexahydro-2,4a,5-triaza-fluoren-6-ylmethyl ester;
Cyclohexyl-carbamic acid 4-methyl-1,2,3,4,9,9a-hexahydro-2,4a,5-triaza-fluoren-6-ylmethyl ester;
(4R,9aR)-Ethyl-carbamic acid 4-methyl-1,2,3,4,9,9a-hexahydro-2,4a,5-triaza-fluoren-6-ylmethyl ester;
(4R,9aR)-Phenyl-carbamic acid 4-methyl-1,2,3,4,9,9a-hexahydro-2,4a,5-triaza-fluoren-6-ylmethyl ester; and
(4R,9aR)-Benzyl-carbamic acid 4-methyl-1,2,3,4,9,9a-hexahydro-2,4a,5-triaza-fluoren-6-ylmethyl ester.

19. A compound selected from the group
(4R,9aR)-Allyl-carbamic acid 4-methyl-1,2,3,4,9,9a-hexahydro-2,4a,5-triaza-fluoren-6-ylmethyl ester;
(4R,9aR)-Ethyl-carbamic acid 1-(RS)-(4-methyl-1,2,3,4,9,9a-hexahydro-2,4a,5-triaza-fluoren-6-yl)-propyl ester;
(4R,9aR)-Ethyl-carbamic acid 1-(RS)-(4-methyl-1,2,3,4,9,9a-hexahydro-2,4a,5-triaza-fluoren-6-yl)-butyl ester;
(4R,9aR)-Ethyl-carbamic acid 1-(S)-(4-methyl-1,2,3,4,9,9a-hexahydro-2,4a,5-triaza-fluoren-6-yl)-ethyl ester;
(4R,9aR)-Propyl-carbamic acid 1-(S)-(4-methyl-1,2,3,4,9,9a-hexahydro-2,4a,5-triaza-fluoren-6-yl)-ethyl ester;
(4R,9aR)-Isopropyl-carbamic acid 1-(S)-(4-methyl-1,2,3,4,9,9a-hexahydro-2,4a,5-triaza-fluoren-6-yl)-ethyl ester;
(4R,9aR)-Pyrrolidine-1-carboxylic acid 4-methyl-1,2,3,4,9,9a-hexahydro-2,4a,5-triaza-fluoren-6-ylmethyl ester; and
(4R,9aR)-Piperazine-1,4-dicarboxylic acid benzyl ester 4-methyl-1,2,3,4,9,9a-hexahydro-2,4a,5-triaza-fluoren-6-ylmethyl ester.

20. A compound selected from the group:
(4R,9aR)-6-chloro-4-methyl-1,2,3,4,9,9a-hexahydro-2,4a,5-triaza-fluorene;
(4R,9aR)-6-bromo-4-methyl-1,2,3,4,9,9a-hexahydro-2,4a,5-triaza-fluorene;
(R)-4,6-dimethyl-1,2,3,4-tetrahydro-2,4a,5-triaza-fluorene;
(4R,9aR)-4,6-dimethyl-1,2,3,4,9,9a-hexahydro-2,4a,5-triaza-fluorene;
(4R,9aR)-6-ethyl-4-methyl-1,2,3,4,9,9a-hexahydro-2,4a,5-triaza-fluorene;
(4R,9aR)-4-methyl-6-trifluoromethyl-1,2,3,4,9,9a-hexahydro-2,4a,5-triaza-fluorene;
(4R,9aR)-6-cyclopropyl-4-methyl-1,2,3,4,9,9a-hexahydro-2,4a,5-triaza-fluorene; and
(4R,9aR)-6-cyclopropylmethoxymethyl-4-methyl-1,2,3,4,9,9a-hexahydro-2,4a,5-triaza-fluorene.

21. A compound selected from the group:
(4R,9aR)-6-methoxymethyl-4-methyl-1,2,3,4,9,9a-hexahydro-2,4a,5-triaza-fluorene;
(R)-6-chloro-4,9-dimethyl-1,2,3,4-tetrahydro-2,4a,5-triaza-fluorene;
(4R,9aR)-6-difluoromethyl-4-methyl-1,2,3,4,9,9a-hexahydro-2,4a,5-triaza-fluorene;
(4R,9aR)-6-fluoromethyl-4-methyl-1,2,3,4,9,9a-hexahydro-2,4a,5-triaza-fluorene;
(4R,9aR)-6-(1-(S)-hydroxy-ethyl)-4-methyl-3,4,9,9a-tetrahydro-1H-2,4a,5-triaza-fluorene;
(4R,9aR)-6-(1-(S)-methoxy-ethyl)-4-methyl-1,2,3,4,9,9a-hexahydro-2,4a,5-triaza-fluorene;
(4R,9aR)-6-(1-(S)-ethoxy-ethyl)-4-methyl-1,2,3,4,9,9a-hexahydro-2,4a,5-triaza-fluorene;
(4R,9aR)-6-(1-(S)-cyclopropylmethoxy-ethyl)-4-methyl-1,2,3,4,9,9a-hexahydro-2,4a,5-triaza-fluorene; and
(4R,9aR)-6-allylsulfanyl-4-methyl-1,2,3,4,9,9a-hexahydro-2-4a,5-triaza-fluorene.

22. A compound selected from the group consisting of:
(4R,10aR)-6-Bromo-4-methyl-3,4,9,9a-tetrahydro-1H-2,4a,5-triaza-fluorene-2-carboxylic acid tert-butyl ester;
7-Oxy-pyrrolo[2,3-b]pyridine-1,2-dicarboxylic acid 1-tert-butyl ester 2-ethyl ester;
6-Bromo-pyrrolo[2,3-b]pyridine-1,2-dicarboxylic acid 1-tert-butyl ester 2-ethyl ester;
6-Bromo-1H-pyrrolo[2,3-b]pyridine-2-carboxylic acid ethyl ester;
6-Hydroxy-1H-pyrrolo[2,3-b]pyridine-2-carboxylic acid ethyl ester; and
6-Hydroxy-pyrrolo[2,3-b]pyridine-1,2-dicarboxylic acid 1-tert-butyl ester 2-ethyl ester.

23. A pharmaceutical composition comprising a therapeutically effective amount of a compound of formula I, claim 1, and a therapeutically inert carrier.

24. The pharmaceutical composition of claim 23 further comprising a therapeutically effective amount of a lipase inhibitor.

25. The pharmaceutical composition of claim 24, wherein the lipase inhibitor is orlistat.

26. A method of treating obesity comprising administering to a patient in need of such therapy a therapeutically effective amount of a compound of formula I, claim 1.

27. A method of treatment of obesity in a human in need of such treatment comprising administration to the human a therapeutically effective amount of a compound of claim 1 and a therapeutically effective amount of a lipase inhibitor.

28. The method of claim 27, wherein the lipase inhibitor is orlistat.

29. The method of claim 28 wherein the compound of formula I and the lipase inhibitor are administered simultaneously, separately or sequentially.

30. A process for preparing a compound of formula I, claim 1, comprising:
a) reducing a compound of formula B to obtain a compound of formula Ib

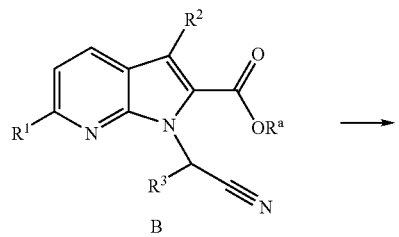

B

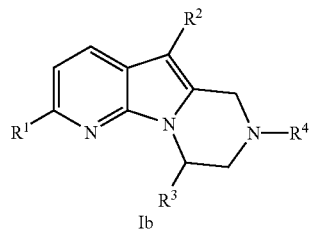

Ib wherein R¹ to are defined as in claim 1, R⁴ is hydrogen and R$^a$ is alkyl.

31. A process for preparing a compound of formula I, claim 1, comprising reducing a compound of formula D to obtain a compound of formula Ib

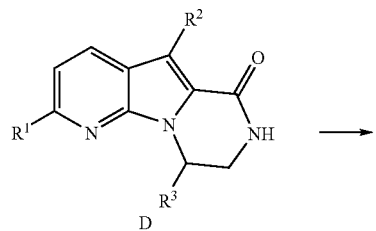

D

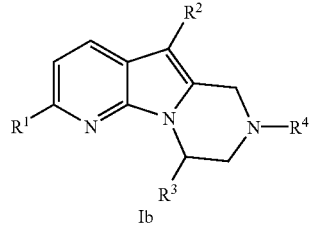

Ib wherein R¹ to R³ are defined as in claim 1 and R⁴ is hydrogen.

32. A process for preparing a compound of formula I, claim 1, comprising reducing a compound of formula Ib to obtain a compound of formula Ia

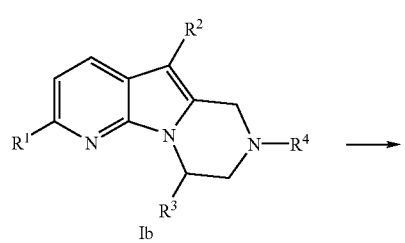

Ib

-continued

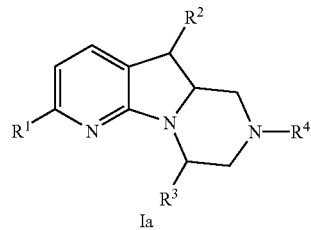

Ia wherein R¹ to R⁴ are defined as in claim 1.

33. A process for preparing a compound of formula I, claim 1, comprising reducing a compound of formula K to obtain a compound of formula Ia

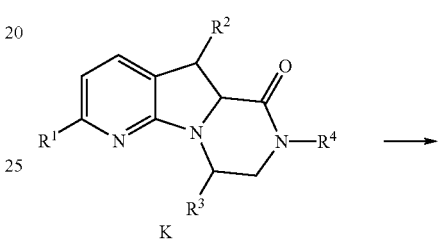

K

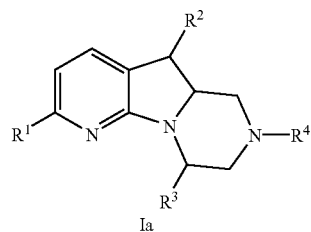

Ia wherein R¹ to R⁴ are defined as in claim 1.

34. A process for preparing a compound of formula I, claim 1, comprising cleaving the protective group (PG) of a compound of formula Ic to obtain a compound of formula Id

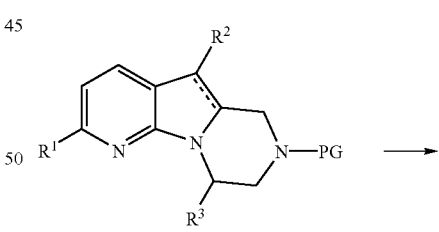

Ic

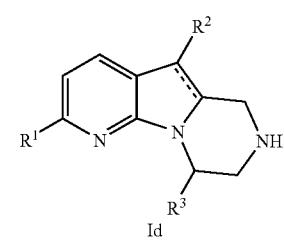

Id wherein R¹ to R³ are defined as in claim 1.

* * * * *

UNITED STATES PATENT AND TRADEMARK OFFICE
CERTIFICATE OF CORRECTION

| | | |
|---|---|---|
| PATENT NO. | : 7,098,337 B2 | Page 1 of 1 |
| APPLICATION NO. | : 10/350616 | |
| DATED | : August 29, 2006 | |
| INVENTOR(S) | : Adams et al. | |

It is certified that error appears in the above-identified patent and that said Letters Patent is hereby corrected as shown below:

In column 85, line 23 after the words "wherein R1 to" insert the word -- R3 --

Signed and Sealed this

Thirtieth Day of October, 2007

JON W. DUDAS
*Director of the United States Patent and Trademark Office*